US012319928B2

(12) United States Patent
Song et al.

(10) Patent No.: US 12,319,928 B2
(45) Date of Patent: Jun. 3, 2025

(54) METHODS OF TREATING DANON DISEASE

(71) Applicant: THE REGENTS OF THE UNIVERSITY OF COLORADO, A BODY CORPORATE, Denver, CO (US)

(72) Inventors: Kunhua Song, Centennial, CO (US); Congwu Chi, Broomfield, CO (US); Yingqiong Cao, Denver, CO (US)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 1038 days.

(21) Appl. No.: 16/827,454

(22) Filed: Mar. 23, 2020

(65) Prior Publication Data
US 2020/0299727 A1 Sep. 24, 2020

Related U.S. Application Data

(60) Provisional application No. 62/822,744, filed on Mar. 22, 2019, provisional application No. 62/821,950, filed on Mar. 21, 2019.

(51) Int. Cl.
*C07H 21/04* (2006.01)
*C12N 9/22* (2006.01)
*C12N 15/86* (2006.01)
*C12N 15/90* (2006.01)

(52) U.S. Cl.
CPC .............. *C12N 15/86* (2013.01); *C12N 9/22* (2013.01); *C12N 15/902* (2013.01); *C12N 2310/20* (2017.05); *C12N 2510/00* (2013.01); *C12N 2800/80* (2013.01)

(58) Field of Classification Search
None
See application file for complete search history.

(56) References Cited

FOREIGN PATENT DOCUMENTS

WO WO 2018170239 * 9/2018

OTHER PUBLICATIONS

Xu et al. (Optimized guide RNA structure for genome editing via Cas9. Oncotarget. Oct. 7, 2017;8(55):94166-94171).*
Endo et al. ("Danon disease: a phenotypic expression of LAMP-2 deficiency." Acta neuropathologica 129.3 (2015): 391-398).*
Lau CH, Suh Y. (In vivo genome editing in animals using AAV-CRISPR system: applications to translational research of human disease. F1000Res. Dec. 20, 2017;6:2153).*
Xu et al. (Optimized guide RNA structure for genome editing via Cas9. Oncotarget. Oct. 7, 2017;8(55):94166-94171). supplemental.*
Chi, Congwu et al., "LAMP-2B regulates human cardiomyocyte function by mediating autophagosome—lysosome fusion", PNAS; vol. 116, No. 2, Jan. 8, 2019, pp. 556-565.

* cited by examiner

*Primary Examiner* — Kimberly Chong
(74) *Attorney, Agent, or Firm* — Dorsey & Whitney LLP

(57) ABSTRACT

The disclosed technology includes methods of treating Danon disease, for example correcting genetic mutations in the LAMP-2 gene and ameliorating at least one Danon disease phenotype, for example defective LAMP-2B-mediated autophagy. In some implementations, the disclosed methods include editing a mutated form of the LAMP-2 gene in a patient in need thereof. In some implementations, editing the mutated form of the LAMP-2 gene may include use of a CRISPR editing technique targeted to the mutated form of the LAMP-2 gene. As a result, mutated LAMP-2 proteins in mammalian subjects may be restored in at least some of the affected cells, for example cardiomyocytes.

20 Claims, 55 Drawing Sheets
(50 of 55 Drawing Sheet(s) Filed in Color)
Specification includes a Sequence Listing.

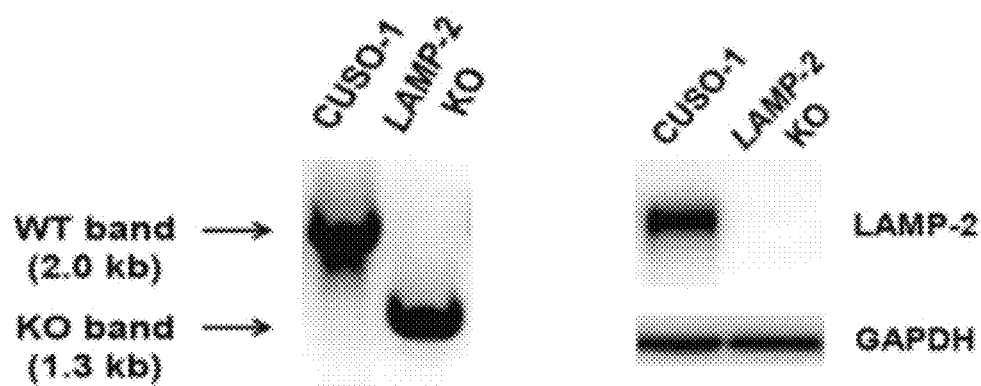
Fig. 11B
Fig. 11C
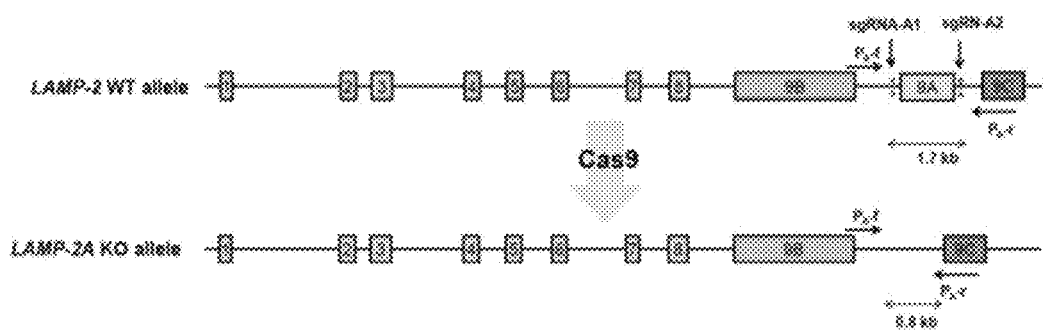
Fig. 11D
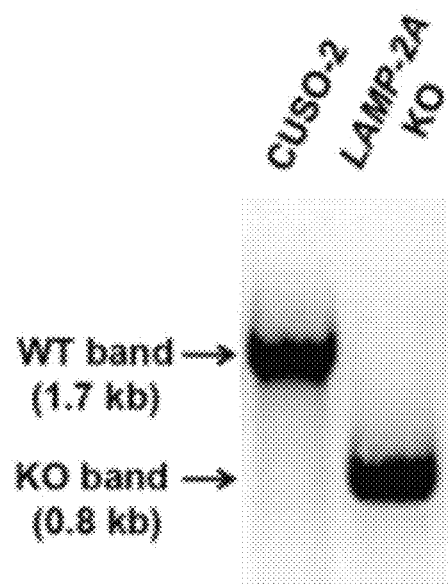
Fig. 11E

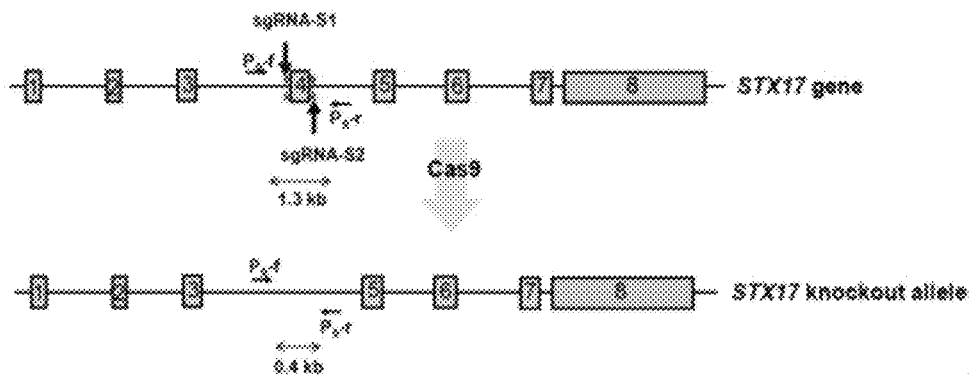
Fig. 14C
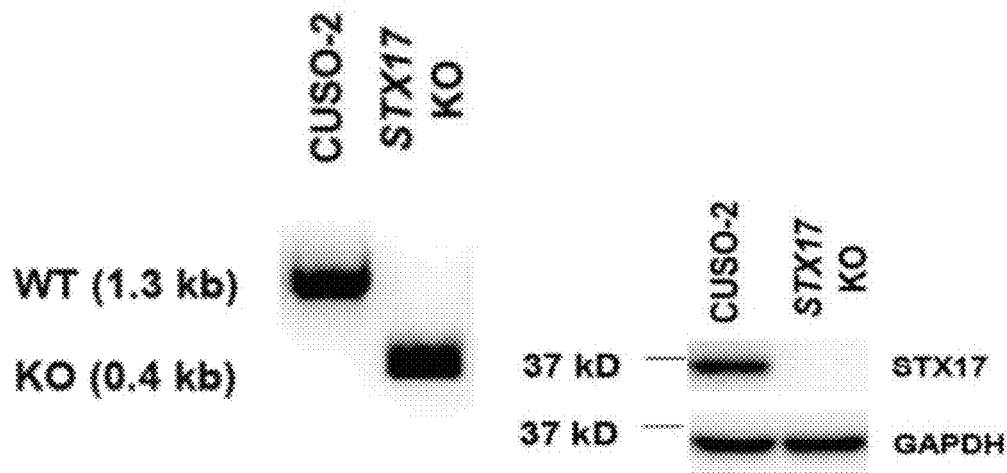
Fig. 14D     Fig. 14E

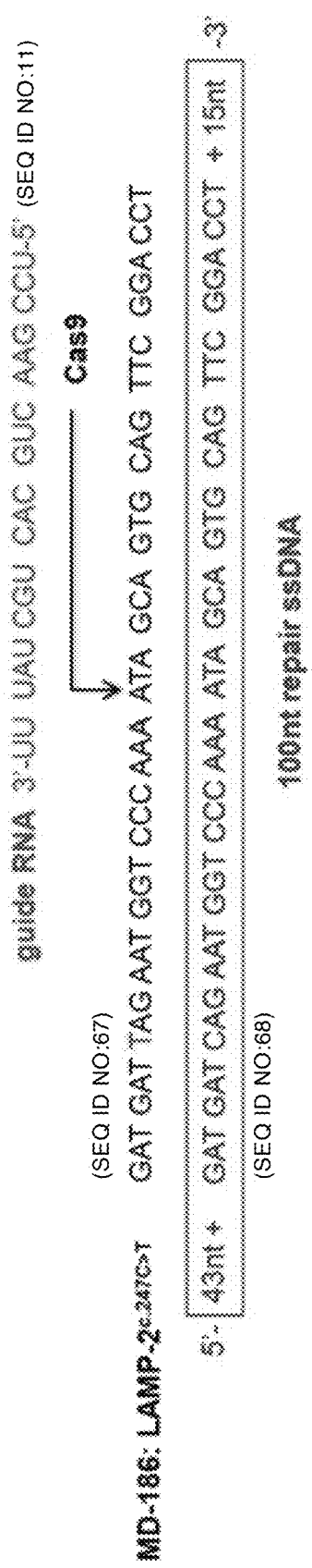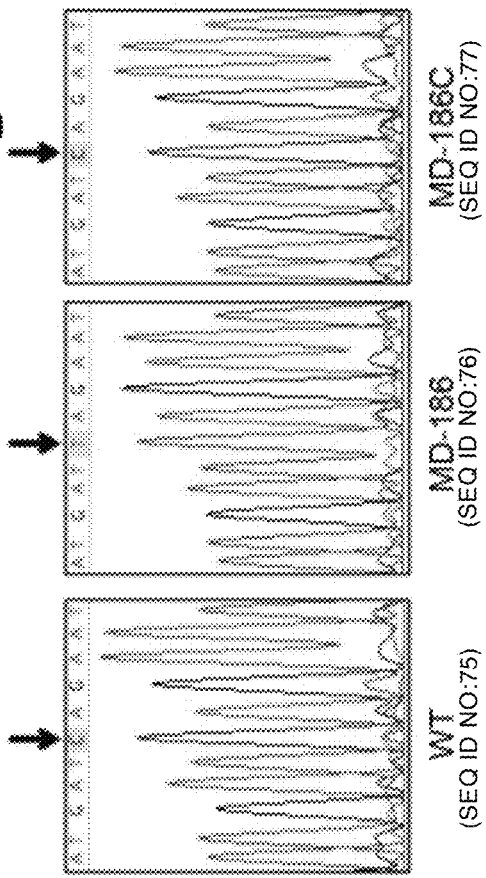
Fig. 18A  Fig. 18B  Fig. 18C

1) MD-506 (c.64+1 G>A, point mutation, splicing) correction:
Guide RNA: GGCGGACAGACTAATCGGGA (SEQ ID NO:50)
Repair ssDNA:
CTCTTCCCGGTTCCGGGCTCAGGGCTCGTTCTGGTCTGCCTAGTCCTGGGTGAGTTGTCGGGCCCTCCCGATT
AGTCTGTCCGCCTGGGCCCGGGGCACC (SEQ ID NO:51)
Reference: (PMID: 30584088; Chi C, Leonard A, Knight WE, et al. LAMP-2B regulates human cardiomyocyte function by mediating autophagosome-lysosome fusion. *Proc Natl Acad Sci U S A*. 2019;116(2):556–565. doi:10.1073/pnas.1808618116)

2) MD-111 (c.1082 delA, 1-nt deletion, frame shift) correction:
Guide RNA: CAGCCTTTCAATGTGACACA (SEQ ID NO:52)
Repair ssDNA:
AAGAACATAAATTATTAATGAAGTTTGCTTGATTCTTACCTGTAGAATACTTTCCTTGTGTCACATTGAAAGGCTG
AACCCTTAGATCAAAGGTATTTAT (SEQ ID NO:53)
Reference: (PMID: 30584088 ; Chi et al.)

3) c.184-190delAAAACTG (7-nt deletion, frame shift) correction:
Guide RNA: CACAGTGCCATGGTCTGAAA (SEQ ID NO:54)
Repair ssDNA:
GATGAATTTCACAGTACGCTATGAAACTACAAATAAAACTTATAAAACTGTAACCATTTCAGACCATGGCACTGTG
ACATATAATGGAAGCATTTGTGGG (SEQ ID NO:55)
Reference: (PMID: 25228319; D'souza et al.)

4) c.320_321 insCATC (4-nt insertion, frame shift) correction:
Guide RNA: CTGGATTGCGAATTTTACCA (SEQ ID NO:56)
Repair
ssDNA: TGTTATCACCAGTGTTGTAGGAAAATGAGACGCTGTCAATTGAATAAGTAGATGCTGCCTTGGTAAAATT
CGCAATCCAGGAAAAGCCAGGTCCGAACTG (SEQ ID NO:57)
Reference: (PMID: 22108829, Cheng Z, Cui Q, Tian Z, et al. Danon disease as a cause of concentric left ventricular hypertrophy in patients who underwent endomyocardial biopsy. *Eur Heart J*. 2012;33(5):649–656. doi:10.1093/eurheartj/ehr420)

5) c.737 A>G (point mutation, missense D246G) correction:
Guide RNA: GCTGCAGCTGAACATCACTC (SEQ ID NO:58)
Repair ssDNA:
AAATGAAATGCAAAAAGGATGTATTGATAAAGATAGACACCTATACCTTATCCTGAGTGATGTTCAGCTGCAGCC
CCATGGTAGCCAGCAGACAAGTATC (SEQ ID NO:59)
Reference: (PMID: 25228319; D'souza et al.)

6) c.961 T>C (point mutation, missense W321R) correction:
Guide RNA: GCACATATAAGAACTTCCCA (SEQ ID NO:60)
Repair ssDNA:
GTTTCTTTTCTTTGAAGTTTTCAGCATTGCAAATAACAATCTCAGCTACTGGGATGCCCCCCTGGGAAGTTCTTAT
ATGTGCAACAAAGAGCAGACTGTT (SEQ ID NO:61)
Reference: (PMID: 15907287; Musumeci O, Rodolico C, Nishino I, et al. Asymptomatic hyperCKemia in a case of Danon disease due to a missense mutation in Lamp-2 gene. *Neuromuscul Disord*. 2005;15(6):409–411. doi:10.1016/j.nmd.2005.02.008)

7) c.1204 A>T (point mutation in Exon 9B, introduced a stop codon) correction:
Guide RNA: ATAGTGATTGCTTACGTAAT (SEQ ID NO:62)
Repair ssDNA:
GAGATCACGTATTGATTAGTGTTACAGAGTCTGATATCCAGCATAACTTTTCTTCTGCCAATTACGTAAGCAATC
ACTATAACGATAATCAAGCCTGAA (SEQ ID NO:63)
Reference: (PMID: 22541782; Hong D, Shi Z, Wang Z, Yuan Y. Danon disease caused by two novel mutations of the LAMP2 gene: implications for two ends of the clinical spectrum. *Clin Neuropathol*. 2012;31(4):224–231. doi:10.5414/NP300465)

*Fig. 21*

METHODS OF TREATING DANON DISEASE

CROSS REFERENCE TO RELATED APPLICATIONS

The present application claims the benefit of priority to U.S. Provisional Patent Application No. 62/822,744, entitled "Methods of Treating Danon Disease," filed Mar. 22, 2019, and U.S. Provisional Patent Application No. 62/821,950, entitled "Methods of Treating Danon Disease," filed Mar. 21, 2019, the entireties of both of which are hereby incorporated by reference herein for all purposes.

STATEMENT REGARDING FEDERALLY SPONSORED RESEARCH OR DEVELOPMENT

This invention was made with government support under grant number HL133230 awarded by National Institutes of Health. The government has certain rights in this invention.

SEQUENCE LISTING

The instant application contains a Sequence Listing which has been submitted electronically in ASCII format and is hereby incorporated by reference in its entirety. Said ASCII copy, created on 22 Nov. 2023, is named P284827.US.03_ST25 and is 17,025 bytes in size.

BACKGROUND

Symptoms of Danon disease include hypertrophic/dilated cardiomyopathy, heart failure, cardiac, arrythmia, muscle weakness, retinopathy, and mental retardation. Most affected individuals have a thickening of the heart muscle that can make pumping blood more difficult. These symptoms can lead to heart failure and premature death. No specific or effective therapeutics have been identified for Danon disease.

SUMMARY

The disclosed technology includes methods of treating Danon disease, which include genetic corrections of LAMP-2 mutations. In many embodiments, the disclosed methods may result in correcting defective LAMP-2B-mediated autophagy. In some implementations, the disclosed methods include editing a mutated form of the LAMP-2 gene, wherein the mutated form of the LAMP-2 gene comprises one or more of an insertion, deletion, or substitution. In some implementations, editing the mutated form of the LAMP-2 gene may include a Clustered Regularly Interspaced Short Palindromic Repeat (CRISPR), Zinc-finger nuclease, or TALEN editing technique targeted to the mutated form of the LAMP-2 gene. In some implementations, the CRISPR technique may include using a single guide RNA (SgRNA). In some implementations, a composition for use in editing a mutated form of a LAMP-2 gene may include an isolated nucleic acid sequence encoding a CRISPR-associated endonuclease and at least one guide RNA (gRNA), the gRNA being complementary to a target sequence in the mutated form of the LAMP-2 gene.

In some implementations, the SgRNA may include AGAAGUUUUACACCCCUACC (SEQ. NO:1). In some implementations, the SgRNA may include AUGAUCUGAAGACGACUAUA (SEQ. NO:2). In some implementations, the SgRNA may include ACUUCCUAACACGCAUAUUU (SEQ. NO:3). In some implementations, the SgRNA may include UUGGGUCUGUAUCAUCCCUA (SEQ. NO:4). In some implementations, the SgRNA may include CAACUUCAAGUAACUAAGAC (SEQ. NO:5). The SgRNA may include GGCCUCGAUUGAUGCUAGGC (SEQ. NO:6). The SgRNA may include GCAAGCGCAAUUCUCUAUUU (SEQ. NO:7). The SgRNA may include UGGAACACCUGUAUGGGUUA (SEQ. NO:8). The SgRNA may include AUAUAGUGUAACCAUUGAGC (SEQ. NO:9). The SgRNA may include GUCCAAGGAUUCAGCAUAUU (SEQ. NO:10). The SgRNA may include UCCGAACUGCACUGCUAUUU (SEQ. NO:11). In some implementations, editing the mutated form of the LAMP-2 gene may include administering a LAMP-2 editing protein to at least one cell with a mutated form of the LAMP-2 gene. The LAMP-2 editing gene may be a CRISPR protein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A depicts an expression of the three LAMP-2 isoforms in different types of cells examined by RNA-seq or qPCR. RNAs from three human hearts were used for qPCR. FPKM, fragments per kilobase of exon per million reads. FIG. 1B depicts an immunoblotting analysis of LAMP-2 expression in indicated hiPSC-CMs.

FIG. 2A depicts that autophagic flux in control and LAMP-2 isoform-specific knockout hiPSC-CMs under regular and starvation conditions was assayed. Cells were cultured in either regular or starvation medium with or without 400 nM bafilomycin A1 for 4 hours followed by immunoblotting analysis of indicated proteins. Quantification of LC3-II/GAPDH from three independent experiments is shown in FIG. 12G. FIG. 2B depicts autophagic flux in indicated hiPSC-CMs was assayed. Quantification of LC3-II/GAPDH from three independent experiments is shown in FIG. 12H. FIG. 2C depicts that LAMP-2B KO hiPSCCMs were infected with adenovirus carrying either LAMP-2A (Ad-LAMP-2A) or LAMP-2B (Ad-LAMP-2B). Three days later, autophagic flux was assayed. Quantification of LC3 II/GAPDH from three independent experiments is shown in FIG. 13B. FIGS. 2D and 2E depict monitoring autophagic flux as indicated hiPSC-CMs by using mRFP-EGFP-LC3. Indicated hiPSC-CMs were infected with adenovirus carrying mRFP-EGFP-LC3. hiPSC-CMs were cultured in regular or starvation medium for 4 hours followed by imaging. Representative confocal images and statistical analysis of GFP+, RFP+, and GFP−, RFP+ puncta are shown in FIGS. 2D and 2E, respectively. Fifteen to 20 cells for each cell line per condition were analyzed. Data are presented as mean+SD. *P<0.05 as assessed by Student's t test. (Scale bars, 10 µM.) FIGS. 2F and 2G depict representative confocal images of indicated hiPSC-CMs stained for LC3 (green), LysoTracker (red), and nuclei (blue). hiPSC-CMs were starved for 4 hours, followed by immunostaining and confocal imaging sequentially. Statistical analysis of colocalization of LC3 puncta and LysoTracker in hiPSC-CMs (20 cells for each group) in FIG. 2G. Data are presented as mean+SD for LC3 puncta/lysosomes or mean–SD for LC3 puncta alone. (Scale bars, 5 µM.)

FIG. 3A depicts that HEK293 cells were transfected with HA-ATG14 plus empty vector, LAMP-2B shown in red box, or LAMP-2A with or without FLAG-STX17, FLAG-SNAP29, and FLAG-VAMP8. Two days later, cells were lysed and immunoprecipitated with anti-HA antibody. Immunoblotting was performed with anti-HA, anti-LAMP-2, and anti-FLAG antibodies. FIG. 3B depicts that HEK293 cells were transfected with HA-ATG14 and FLAG-VAMP8 with empty vector, LAMP-2B, or LAMP-2BΔCCD. Two days later, cells were lysed and immunoprecipitated with anti-HA antibody, followed by immunoblotting with anti-LAMP-2, anti-FLAG, or anti-HA antibodies. FIGS. 3C and 3D depicts that Control, LAMP-2 KO (FIG. 3C), or Danon (FIG. 3D) hiPSCCMs were infected with adenovirus carrying HA-ATG14 (Ad-HA-ATG14) with or without coinfection with adenovirus carrying LAMP-2B (Ad-LAMP-2B). Three days later, cardiomyocytes were lysed and immunoprecipitated with anti-HA antibody, followed by immunoblotting analysis for indicated proteins. FIGS. 3E and 3F depict representative confocal images of indicated hiPSC-CMs stained for HA-ATG14 (red) and FLAG-VAMP8 (green) in FIG. 3E. hiPSCCMs were infected with adenovirus carrying HA-ATG14 or FLAG-VAMP8. Three days later, hiPSC-CMs were starved for 2 hours followed by immunostaining for HAATG14 and FLAG-VAMP8. White boxes are enlarged in Insets. Quantification of colocalization of ATG14 and VAMP8 is shown in FIG. 3F. n=17-24 cardiomyocytes, Student's t test, *P<0.0001. Data are presented as mean±SD. (Scale bars, 5 µM.)

FIGS. 4A-4D depict immunoblotting analysis of indicated proteins in HEK293 cells. HEK293 cells transfected with empty vector, LAMP-2A, LAMP-2B, or LAMP-2BΔCCD were treated with siRNAs against luciferase (siControl) or STX17. Three days later, cells were cultured in regular or starvation medium for 4 hours with or without 400 nM of bafilomycin A1 (Baf. A1). Western blotting was performed with indicated antibodies. Densitometry quantification of LC3-II/GAPDH from three independent experiments in FIG. 4A is shown in FIG. 14A; FIG. 4B is shown in FIG. 4C; and FIG. 4D is shown in FIG. 14B, with data being normalized to siControl-treated cells under starved conditions in each experiment. Data are presented as mean±SD. *P<0.05 as assessed by Student's t test. ns, not significant. FIGS. 4E and 4F depict an immunoblotting analysis of indicated proteins in indicated hiPSC-CMs. hiPSC-CMs infected with adenovirus carrying LacZ (Ad-LacZ) or LAMP-2B (Ad-LAMP-2B). Autophagic flux was assayed as described in FIGS. 4A-4D. Densitometry quantification of LC3-II/GAPDH is shown in FIG. 4F, with data being normalized to control hiPSC-CMs under starved conditions in each experiment. Data are presented as mean±SD. *P<0.05 as assessed by Student's t test. n=4. ns, not significant.

FIGS. 6A and 6B depict that autophagic flux measured by LC3-II in control, MD-186, and corrected MD-186C hiPSC-CMs was assayed. Quantification of LC3-II/GAPDH from three independent experiments is shown in FIG. 6B. Data are presented as mean±SD. *P<0.05 as assessed by Student's t test. ns, not significant. FIGS. 6C and 6D depict monitoring autophagic flux in indicated hiPSC-CMs by using mRFP-EGFP-LC3. hiPSC-CMs were infected with adenovirus carrying mRFP-EGFP-LC3. hiPSC-CMs were cultured in regular or starvation medium for 4 hours followed by imaging. Representative fluorescent images and statistical analysis of GFP+/RFP+ and GFP−/RFP+ puncta are shown in FIGS. 6C and 6D, respectively. Twenty cells for each condition were analyzed. Data are presented as mean±SD. *P<0.05 as assessed by Student's t test. ns, not significant. FIG. 6E depicts cellular ATP content in control, MD-186, and MD-186C hiPSC-CMs was measured. Student's t test, *P<0.005, n=3. Data are presented as mean±SD. ns, not significant. FIG. 6F depicts OCR of control, MD-186, and MD-186C hiPSC-CMs to indicate mitochondrial function was measured using the Seahorse XF Cell Mito Stress Test Kit. Representative time course data for indicated hiPSC-CMs are shown at Left. Data are presented as mean±SD. Statistical analysis of OCR are shown at Right. Student's t test, *P<0.05, n=3. Data are presented as mean±SD. ns, not significant.

FIG. 7A shows ATP levels in indicated hiPSC-CMs is shown. n=3, Student's t test, *P<0.01. Data are presented as mean+SD. FIGS. 7B and 7C depict mitochondrial function indicated by OCR of hiPSC-CMs, measured using the Seahorse XF Cell Mito Stress Test Kit. Representative time course data for indicated hiPSCCMs are shown. Data are expressed as mean±SD. Quantification of OCR is shown in FIG. 7C. n=3. Data are presented as mean+SD, Student's t test, *P<0.05 versus control. ns, not significant. FIG. 7D depicts maximal tension generated by myofibrils isolated from hearts of control and patients with Danon disease. Nine to 16 myofibrils were isolated from cardiac tissue from each patient. Three donors and three Danon disease hearts were analyzed, respectively. Each point represents the maximal tension of a single myofibril of an individual patient. Data are presented as mean±SD. P values were obtained from a one-way ANOVA with a Tukey's multiple comparison test, *P<0.05. FIGS. 7E-7G depict a twitch force produced by single hiPSC-CMs on day 60. Force of control and LAMP-2 KO hiPSC-CMs measured from the six to seven independent experiments (with ~25 cells each) are plotted together in FIG. 7E. Force of control and Danon hiPSC-CMs measured from the three independent experiments (with ~25 cells each) are plotted together in FIG. 7F. FIG. 7G depicts a twitch force of Danon (MD-186) and genetics-corrected (MD-186C) hiPSC-CMs measured from the four to five independent experiments (with ~25 cells each). Each data point represents the average force per post of an individual cell. Lines represent average force per post for each group. The reported P value was obtained from a one-way ANOVA with a Bonferroni post hoc test, *P<0.05

FIG. 8A depicts mutations in the LAMP-2 gene in patients with Danon disease confirmed by NA sequencing. Arrows indicate mutation sites relative to control genomic sequence. FIG. 8B depicts a representative hiPSC-colony morphology and expression of pluripotency markers NANOG, SSEA-3, SSEA-4, TRA-1-81 and TRA-2-49 in hiPSCs. FIG. 8C depicts a representative karyotype image. hiPSCs used in this study had normal 46, XY karyotype. FIG. 8D depicts hiPSCs used in this study were differentiated into derivatives of three germ layers: endoderm, mesoderm and ectoderm. FIG. 8E depicts a schematic indicating the protocol and timeline for cardiac differentiation of hiPSCs and enrichment of cardiomyocytes. FIG. 8E depicts an enrichment of cardiomyocytes derived from hiPSCs (hiPSC-CMs) for this study by lactate selection. Flow cytometry analysis of cTnT+ cardiomyocytes in culture was performed 30 days postinduction shown in FIG. 8F. FIG. 8G depicts an immunoblotting analysis of LAMP-2 and LAMP-1 expression in control and Danon hiPSC-CMs. Control and Danon hiPSC-CMs expressed comparable levels of LAMP-1, a lysosomal marker. FIG. 8H depicts a differentiation of control and Danon hiPSCs into cardiomyocytes. Before lactate selection, flow cytometry analysis of cTnT+ cardiomyocytes in culture was performed 10 days post-induction shown in FIG. 8E. FIGS. 8I-K depict a representative immunofluorescence images of hiPSC-CMs stained for cTnT (green; FIG. 8I), cTnI (green; FIG. 8J), α-actinin (green; FIG. 8K) and MYL2 (red; FIG. 8K). FIG. 8L depicts an expression of MYH6 and MYH7 in mouse hearts, human hearts and hiPSC-CMs. FIG. 8M depicts a representative confocal images of control and Danon hiPSC-CMs stained for α-actinin.

FIG. 9A depicts a detection of glycogen in hiPSC-CMs by Periodic Acid-Schiff (PAS) staining. FIGS. 9B-C depict representative transmission electron microscopy images of hiPSC-CMs. Red arrows point to vacuoles. A double-membrane autophagic vacuole containing mitochondria (Mito) from a Danon hiPSC-CM is shown in FIG. 9C. FIG. 9D depicts representative fluorescence images of hiPSC-CMs immunostained for cTnT (green), TUNEL (red) and DNA (blue) on day 50 and day 100 post-induction. Percentages of TUNEL+ cardiomyocytes and total numbers of examined cells from three independent experiments for each line are shown below the image. hiPSC-CMs were treated with DNase I or 10 μM of H2O2 for 24 hours as positive controls. FIG. 9E depicts cellular ROS were assessed by MitoSOX intensity. Live hiPSC-CMs were incubated with MitoSOX followed by flow cytometry analysis. Three independent repeats were performed. Data are presented as mean fluorescence intensity (MFI)±s.d.

FIG. 10A depicts that the LAMP-2 gene encodes its three isoforms, LAMP-2A, LAMP-2B, and LAMP-2C, through alternative splicing. The three isoforms have identical lysosomal luminal domains, but distinct amino acid sequences for transmembrane (TM) domain and cytosolic CCD. FIG. 10B depicts an expression of the three LAMP-2 isoforms in mouse cardiomyocytes. In adult mouse cardiomyocytes, read densities (red) were plotted along Lamp2 using the Integrative Genomics Viewer (IGV) and quantified as counts. RNA-seq data have been deposited in the Gene Expression Omnibus (GEO). Accession numbers are GSE71405 for NMCMs, and GSE102792 for adult mouse cardiomyocytes. FPKM, fragments per kilobase of exon per million reads. NMCMs, neonatal mouse ventricular cardiomyocytes. FIG. 10C depicts a quantification of LAMP-2 protein in indicated hiPSC-CMs from three independent experiments, e.g., as shown in FIG. 1B. Data are presented as mean±s.d.

FIGS. 11A-I depict generation of hiPSCs to delete LAMP-2, LAMP-2A, LAMP-2B and LAMP-2C, respectively, using CRISPR/Cas9 technology. Genome editing and PCR genotyping strategy for deletion of LAMP-2 is depicted in FIGS. 11A and 11B, LAMP-2A is depicted in FIGS. 11D and 11E, LAMP-2B is depicted in FIGS. 11F and 11G, and LAMP-2C is depicted in FIGS. 11H and 11I. FIG. 11C depicts an immunoblotting analysis of LAMP-2 protein in LAMP-2 KO and isogenic control hiPSC-CMs.

FIGS. 12A-H depict an accumulation of LC3-II levels in LAMP-2 deficient hiPSC-CMs. FIG. 12A depicts cells that were cultured in regular medium with or without 400 nM of bafilomycin A1 (Baf) for 2 hours followed by immunoblotting analysis for LC3-I, LC3-II and GAPDH as a loading control. Fold-change of LC3-II/GAPDH caused by bafilomycin A1 treatment for each type of cells was quantified. FIGS. 12B-C depict autophagic flux in control and Danon hiPSC-CMs, and human skin fibroblasts under regular and starvation conditions, as assayed. Cells were cultured in either regular or starvation medium with or without 400 nM of bafilomycin A1 (Baf) for 4 hours followed by immunoblotting analysis. Densitometry quantification of LC3-II/GAPDH for hiPSC-CMs from three independent experiments is shown in FIG. 12C, with data being normalized to CUSO-1 under regular conditions in each experiment, and combined into groups as indicated. Data from 3 independent experimental repeats are presented as mean±s.d. * P<0.05 as assessed by Student's t-test. FIGS. 12D-E depict autophagic flux in control and LAMP-2 KO hiPSC-CMs, as assayed, as in FIG. 12B. Data in FIG. 12E were normalized to CUSO-1 under regular conditions in each experiment, and are presented as mean±s.d. * P<0.05 as assessed by Student's t-test. Three independent experimental repeats were conducted. FIG. 12F depicts representative immunofluorescence images of hiPSC-CMs stained for cTnT (green) and LC3 (red). hiPSC-CMs were cultured under starvation conditions for 4 hours before they were fixed for immunostaining. LC3 puncta in each cardiomyocyte were counted. Twenty to thirty cells for each group were analyzed. n=3. Student's t-test. *P<0.001. Data are presented as mean+s.d. FIG. 12G depicts a densitometry quantification of LC3 II/GAPDH from three independent experiments shown in FIG. 2A. Data are presented as mean±s.d. * P<0.05 as assessed by Student's t-test. ns, not significant. FIG. 12H depicts a densitometry quantification of LC3-II/GAPDH from three independent experiments shown in FIG. 2B. Data are presented as mean±s.d. * P<0.05 as assessed by Student's t-test.

FIG. 13A depicts that hiPSC-CMs were infected with adenovirus carrying green fluorescent protein (GFP) at a MOI (multiplicity of infection) of 5. Cells were imaged 3 days post-infection. FIG. 13B depicts a densitometry quantification of LC3-II/GAPDH from three independent experiments shown in FIG. 2C. Data are presented as mean±s.d. * P<0.05 as assessed by Student's t-test. ns, not significant.

FIGS. 14A-H depict that the CCD is involved for LAMP-2B to promote autophagosome-lysosome fusion, independently of STX17. FIG. 14A depicts a quantification of LC3-II/GAPDH from three independent experiments shown in FIG. 4A with data being normalized to siControl-treated cells under starved conditions in each experiment. Data are presented as mean±s.d. * P<0.05 as assessed by Student's t-test. ns, not significant. FIG. 14B depicts a quantification of LC3-II/GAPDH from three independent experiments shown in FIG. 4D with data being normalized to siControl-treated cells under starved conditions in each experiment. Data are presented as mean±s.d. * P<0.05 as assessed by Student's t-test. ns, not significant. FIG. 14C depicts a genome editing strategy for knockout of STX17 in hiPSCs using the CRISPR/Cas9 technology. FIG. 14D depicts PCR genotyping for deletion of STX17. PCR primers are shown in FIG. 14C. FIG. 14E depicts an immunoblotting analysis of STX17 protein in STX17 KO and isogenic control hiPSCs. FIGS. 14F-G depict an immunoblotting analysis of indicated proteins in hiPSC-CMs. hiPSC-CMs infected with adenovirus carrying LacZ (Ad-LacZ) or LAMP-2B (Ad-LAMP-2B) were treated with siRNAs against luciferase or STX17. Quantification of LC3-II/GAPDH from three independent experiments shown in FIG. 14G with data being normalized to siControl-treated hiPSC-CMs under starved conditions in each experiment. Data are presented as mean±s.d. * P<0.05 as assessed by Student's t-test. ns, not significant. FIG. 14H depicts an immunoblotting analysis of indicated proteins in control, LAMP-2B KO, STX17 KO hiPSC-CMs. hiPSC-CMs infected with adenovirus carrying LacZ (Ad-LacZ) or LAMP-2B (Ad-LAMP-2B). Quantification of LC3-II/GAPDH is shown in (FIG. 4F).

FIGS. 15A-B depict an immunoblotting analysis of indicated proteins in HEK293. HEK293 cells were transfected with empty vector or LAMP-2B, then were treated with siRNAs against luciferase or VAMP8. Three days later, cells were cultured in regular or starvation medium for 4 hours with or without 400 nM of bafilomycin A1 (Baf. A1). Western blotting was performed with anti-LAMP-2, anti-LC3, anti-VAMP8, and anti-GAPDH antibodies. Quantification of LC3-II/GAPDH from three independent experiments is shown in FIG. 15B, with data being normalized to siControl-treated cells under starved conditions in each experiment. Data are presented as mean±s.d. * P<0.05 as assessed by Student's t-test. See, FIGS. 15C-D. Knockdown of VAMP8 in hiPSC-CMs did not affect lysosome abundance. hiPSCCMs were treated with siRNAs against luciferase as control and against VAMP8. Three days later, hiPSC-CMs were cultured in regular (FIG. 15C) or starvation (FIG. 15D) medium for 4 hours. Cells were incubated with LysoTracker followed by flow cytometry. FIGS. 15E-F depict an immunoblotting analysis of indicated proteins in HEK293 cells. HEK293 cells were transfected with empty vector or LAMP-2B, then were treated with siRNAs against luciferase or ATG14. Autophagic flux was assayed as described in FIG. 15A. Quantification of LC3-II/GAPDH from three independent experiments is shown in FIG. 15F, with data being normalized to siControl-treated cells under starved conditions in each experiment. Data are presented as mean±s.d. * P<0.05 as assessed by Student's t-test.

FIG. 16A depicts a Dendrogram cluster and heat map of 420 differentially expressed genes in control versus Danon hiPSC-CMs identified by RNA-seq. RNA-seq data have been deposited in the Gene Expression Omnibus (GEO) with an accession number of GSE108429. FIG. 16B depicts a correlation analysis of gene expression in three Danon hiPS-CCM lines and LAMP-2 KO hiPSC-CMs. FIG. 16C depicts a gene ontology (GO) analysis showing biological processes associated with genes with known functions differentially expressed in control and Danon hiPSC-CMs. FIG. 16D depicts an TMRM fluorescence intensity of live hiPSC-CMs was analyzed by flow cytometry. n=3. Student's t-test. *P<0.05. ns, not significant. Data are presented as mean+s.d. FIG. 16E depicts that a PINK1 protein was analyzed via immunoblotting on isolated mitochondria from hiPSCCMs. The outer mitochondrial membrane protein voltage dependent anion channel 1 (VDAC) was used as a loading control. Relative PINK1/VDAC levels to CUSO-1 are shown underneath the VDAC blot. Three independent experiments for CUSO-1 and LAMP-2 KO were conducted. FIG. 16F depicts that mitochondrial morphology was categorized in a blinded manner in hiPSC-CMs based on confocal images. Networked morphology in a cardiomyocyte is classified as a mixture of >60% fused and <40% fragmented mitochondria. Intermediate morphology is classified as a mixture of 30%-60% fused and 70%-40% fragmented mitochondria. Fragmented morphology is classified as a mixture of <30% fused and >70% fragmented mitochondria. More than 70 cardiomyocytes for each hiPSC-CM line were categorized per experiment. Three independent experiments were conducted. Data are presented as mean+s.d. Student's t-test. *P<0.05. FIG. 16G-H depicts an immunoblotting analysis of L-OPA1 and S-OPA1 in control, Danon and LAMP-2 KO hiPSC-CMs. Densitometry quantification of S-OPA1/GAPDH from three independent experiments is shown in FIG. 16H with data being normalized to CUSO-1 in each experiment. Data from 3 independent experimental repeats are presented as mean±s.d. * P<0.05 as assessed by Student's t-test.

FIG. 17A depicts ATP levels in two control lines (CUSO-1 and CUSO-2), three Danon lines (MD-111, MD-186, and MD-506) and the LAMP-2 KO line were summarized. n=3, Student's t-test, *P<0.001. Data are presented as mean+s.d. FIGS. 17B-C depict an OCR of control, Danon and LAMP-2 KO hiPSC-CMs in glucose, galactose, or lactate was measured using the Seahorse XF Cell Mito Stress Test Kit. Activity of specific mitochondrial components was measured by OCR after sequentially adding oligomycin (Oligo) to inhibit mitochondrial FIFO ATP synthase, an uncoupling agent (FCCP) to disrupt the mitochondrial membrane potential, and antimycin A plus rotenone (A/R) to inhibit mitochondrial complex I and complex III. Representative time course data for control, Danon and LAMP-2 KO hiPSC-CMs are shown in FIG. 17B. Data are expressed as mean±s.d. Statistical analysis of OCR is shown in FIG. 17C. n=4. Data are presented as mean+s.d. Student's t-test, *P<0.01.

FIGS. 18A-C depict a targeted correction of the LAMP-2 mutation c.247C>T in MD-186. FIG. 18A depicts a schematic of gene correction using the CRISPR/Cas9 approach. The LAMP-2 genomic locus contains the mutation c.247C>T in red. The guide RNA and the repair oligonucleotide are shown. FIG. 18B depicts a point mutation and corrected sequence were determined via Sanger sequencing. FIG. 18C depicts an immunoblotting analysis of LAMP-2 expression in control, Danon MD-186 and corrected MD-186C hiPSCs.

FIG. 21 presents a diagram of the LAMP-2 genomic locus, showing coding (blue rectangles) and non-coding regions (grey rectangle and black lines), and various mutations (red marks) found therein. Note that Exons 9a and 9c are not shown. Below the diagram is a list of LAMP-2 mutations and sequences for use in various embodiments of the disclosed methods for correcting mutations in the LAMP-2. Sequences of guide RNAs are presented using deoxyribonucleotides, therefore U's are represented as T's.

DETAILED DESCRIPTION

Figure 1A:
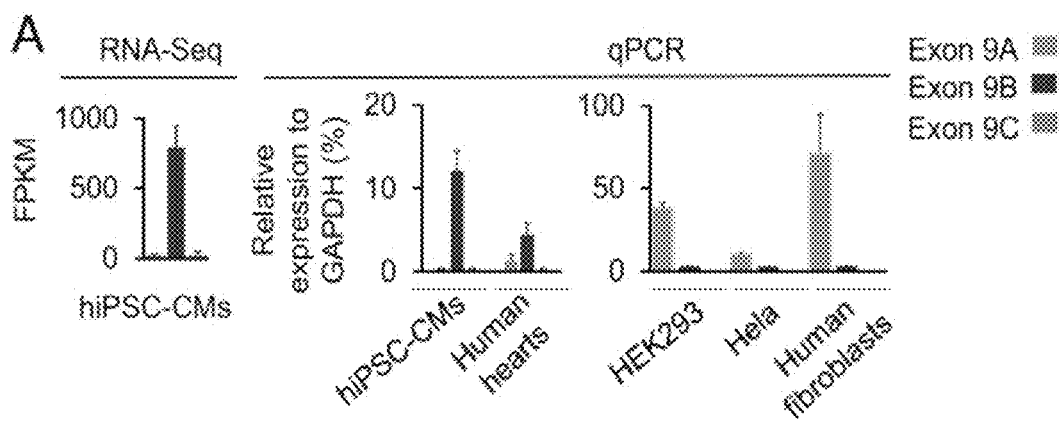
FIGS. 1A-B are schematic representations and images of example results depicting the LAMP-2B as a predominant LAMP-2 isoform expressed in human cardiomyocytes.

Disclosed herein are compositions and methods for genetic modification to treat Danon disease. In some embodiments, compositions and methods include genetic correction of one or more mutations in the LAMP-2 (lysosomal associated membrane protein 2) gene, for example, mutations that may result in defective LAMP-2B-mediated autophagy. In many embodiments, the mutated LAMP-2 gene comprises one or more insertions, deletions, or substitutions in the gene sequence. The disclosed compositions and methods are effective at correcting the insertion, deletion, or substitution to allow expression of a non-mutant LAMP-2 protein, for example non-mutant LAMP-2B.

Autophagy may play a crucial role in cell homeostasis and function. Two types of autophagy have been well studied. Chaperone-mediated autophagy (CMA) is a process of chaperone-dependent selection of cytosolic proteins that are translocated into the lysosome for degradation. Macroautophagy (referred to as autophagy hereafter) is mediated by double-membrane autophagosomes that enclose cytosolic cargoes, followed by fusion with late endosomes/lysosomes for degradation. STX17 localized to autophagosomes may be essential for autophagosome-lysosome fusion as it interacts with SNAP29 and VAMP8 localized to late endosomes/lysosomes. ATG14 localized to autophagosomes may enhance autophagic fusion by interacting with the STX17-SNAP29 complex.

Danon Disease

Mutations in the X-linked LAMP-2 gene are associated with Danon disease, a skeletal and cardiac muscle disorder. Symptoms of Danon disease include hypertrophic/dilated cardiomyopathy, cardiac conduction abnormalities, heart failure, skeletal myopathy, muscle weakness, retinopathy, and mental retardation. Danon disease is often associated with an accumulation of glycogen and vacuoles in a patient's cardiomyocytes. The mean ages in years of diagnosis of cardiomyopathy and death are 13 and 19 in men and 30 and 35 in women.

No specific or effective therapeutics have yet been identified for Danon disease, which might be due to a lack of defined molecular mechanisms of disease pathogenesis. Autophagic dysregulation has been described in muscle tissues and human induced pluripotent stem cell-derived cardiomyocytes (hiPSC-CMs) derived from patients with Danon disease.

LAMP-2 Gene

The LAMP-2 gene provides instructions for making a protein called lysosomal associated membrane protein-2 (LAMP-2), which is found in the membrane of lysosomes. Alternative splicing of pre-LAMP-2 mRNA produces at least three versions (isoforms): LAMP-2A, LAMP-2B, and LAMP-2C. These LAMP-2 isoforms share an identical N-terminal domain but have distinct transmembrane and cytosolic domains at the C terminus. For example, LAMP-2B includes a C-terminal coiled coil domain (CCD) that promotes autophagic fusion.

LAMP-2 deficiency can result in mitochondrial and contractile impairment/abnormalities, lower ATP levels, and defects in autophagosome-lysosome fusion. As one example, LAMP-2B deficiency causes mitochondrial and contractile abnormalities in human cardiomyocytes.

LAMP-2 Mediated Autophagy

Autophagy may play a crucial role in cell homeostasis and function. Two types of autophagy have been well studied. Chaperone-mediated autophagy (CMA) is a process of chaperone-dependent selection of cytosolic proteins that are translocated into the lysosome for degradation. Macroautophagy (referred to as autophagy hereafter) is mediated by double-membrane autophagosomes that enclose cytosolic cargoes, followed by fusion with late endosomes/lysosomes for degradation. STX17, a protein coding gene localized to autophagosomes, may be essential for autophagosome-lysosome fusion as it interacts with SNAP29 and VAMP8 localized to late endosomes/lysosomes. SNAP29 and VAMP8 are both SNAREs involved in autophagy through the direct control of autophagosome membrane fusion with the lysosome membrane. ATG14, another protein coding gene localized to autophagosomes, may enhance autophagic fusion by interacting with the STX17-SNAP29 complex.

The LAMP-2 gene plays a role in mediating autophagy. Alternative splicing of pre-LAMP-2 mRNA produces at least three isoforms: LAMP-2A, LAMP-2B, and LAMP-2C. These LAMP-2 isoforms share an identical N-terminal domain but have distinct transmembrane and cytosolic domains at the C terminus. The role of the LAMP-2 gene in autophagy was demonstrated in a study with mice in which deletion of the three LAMP-2 isoforms (LAMP-2A, LAMP-2B, and LAMP-2C) caused defects in autophagy.

LAMP-2A is a receptor in CMA. Studies have demonstrated that LAMP-2A is involved in autophagy by playing a role in localization of STX17 to autophagosomes in mouse embryonic fibroblasts (MEFs). Using hiPSC-CMs and genome editing-based approaches, LAMP-2B has been identified as a major LAMP-2 isoform expressed in cardiomyocytes involved in autophagic fusion in human cardiomyocytes. Both ATG14 and VAMP8 are believed to be involved for LAMP-2B to promote autophagy-specific fusion in cardiomyocytes. The cytosolic CCD of LAMP-2B may be used to promote formation of the ATG14-VAMP8 complex, as well as to mediate STX17-independent autophagic fusion. LAMP-2B may suppress accumulation of autophagosomes caused by knockdown of STX17 in non-CMs. Knockout of STX17 in hiPSC-CMs caused neither accumulation of autophagosomes nor affected the ability of LAMP-2B to promote autophagy. Knockout of LAMP-2 or LAMP-2B in hiPSCCMs may decrease colocalization of ATG14 with VAMP8, autophagosomal fusion with late endosomes/lysosomes, mitochondrial and contractile function, and reduced adenosine triphosphate (ATP) content. hiPSC-CMs derived from patients with Danon disease recapitulated this phenotype.

Autophagosome number may be determined by levels of microtubule-associated protein light chain 3-II (LC3-II), the membrane form of LC3 and an autophagosomal marker. The amount of LC3-II is correlated with autophagosome number. Therefore, a decrease in LAMP-2B (e.g., LAMP-2 KO hiPSC-CMs), which is associated with blocked autophagosome-lysosome fusion and/or lysosomal degradation, results in increased levels of LC3-II (e.g., an increase in autophagosome number). Alternatively, forced expression or overexpression of LAMP-2B suppresses the LC3-II accumulation caused by LAMP-2B deficiency.

LAMP-2 Gene Modification

Compositions and methods described herein include a targeted correction of a LAMP-2 mutation. For example, disclosed compositions and methods include genome editing to modify or correct a mutation in the LAMP-2 gene. For example, Danon patients can carry mutations that result in deficiency of one or more of the LAMP-2 isoforms. As one example, Danon patients can carry mutations resulting in deficiency of all three LAMP-2 isoforms. As another example, Danon patients can carry one or more mutations resulting in deficiency of the LAMP-2B isoform. For example, deficiency of LAMP-2B rather than LAMP-2A or LAMP-2C is believed to cause metabolic and autophagic abnormalities in human cardiomyocytes. As such, genome editing described herein can be used to modify or correct one or more mutations in one or more LAMP-2 isoform coding or non-coding sequences, for example frameshift, splice, early termination, deletions, insertions, missense, duplication, etc. LAMP-2 mutations that may be corrected by the disclosed method include genetic mutations known to be associated with Danon disease, such as, for example, mutations described in D'souza, et al., "Danon Disease Clinical Features, Evaluation, and Management," Circulation: Heart Failure. September 2014; Vol. 7, Issue 5, pp. 843-849 (available at doi.org/10.1161/CIRCHEARTFAIL-URE.114.001105) and at the Human Gene Mutation Database (www.hgmd.org), which are incorporated by reference herein in its entirety for all purposes.

Genome editing may include deletion, reversion, or correction of a mutated LAMP-2 gene sequence or portion thereof, such as, for example, a LAMP-2A, LAMP-2B, and/or LAMP-2C isoform. For example, one or more exons may be deleted at various locations to generate isogenic LAMP-2 knockout (LAMP-2 KO) cell lines (e.g., hiPSC lines). For example, exons can be selected for deletion to produce LAMP-2A KO, LAMP-2B KO, and/or LAMP-2C KO (e.g., by targeting exon 9A, exon 9B, and exon 9C, respectively).

The disclosed genome editing may include targeting a point mutation. Gene editing can introduce a frameshift mutation, e.g., such that the cell does not express LAMP-2 protein. In some implementations, deletion may be performed using CRISPR/Cas9 technology. Other methods for introducing deletions, well known in the art, are contemplated. In some embodiments, deletions may be performed using Transcription activator-like effector nucleases (TALENs) and Zinc finger nucleases (ZFNs). In TALEN editing, the TALENs are used to induce a double-stranded DNA break at a specific locus in the genome. This break can then be used to introduce a mutation (deletion or insertion), before repair of the break. Like CRISPR and TALENs, ZFNs can be directed to specific sequences to introduce double stranded breaks in the DNA.

In some embodiments, modification includes addition of a normal, non-mutated, LAMP-2 gene or portion thereof, such as, for example, a LAMP-2A, LAMP-2B, and/or LAMP-2C isoform. For example, various vectors or constructs may be used in the disclosed technology to introduce the normal LAMP-2 gene (that is a gene without C at position 247) or portion thereof or isoform into one or more target cells. For example, a viral vector or expression vector or plasmid may be used in the disclosed technology. As one example, an adenovirus carrying either LAMP-2A or LAMP-2B may be used in the disclosed technology.

In some embodiments, editing the mutated form of the LAMP-2 gene may include administering an enzyme, for example a nuclease to at least one cell with a mutated form of the LAMP-2 gene. In many embodiments, the nuclease may target a specific sequence or region in the LAMP-2 gene (coding or non-coding sequence). In most embodiments, the nuclease may be delivered with a target sequence comprising the non-mutated sequence of the LAMP-2 gene.

The nuclease may be a zinc finger, TALEN, or CRISPR-based nuclease. In many embodiments, the nuclease may be a CRISPR protein. For example, CRISPR/Cas9 genome editing technology may be used to target the mutated form of the LAMP-2 gene. For example, in some implementations, a guide RNA molecule (e.g., short guide RNA), a Cas9 protein, and a template nucleic acid are introduced into a cell with an adenovirus virus. In some implementations, the guide RNA molecule, the Cas9 protein, and the template nucleic acid are introduced into cell with an adeno-associated virus (AAV), for example AAV serotype 9 or AAVDJ.

Cells targeted for genome editing may vary. In several embodiments, targeted cells may include mammalian cells, such as human or mouse. In some embodiments, targeted cells may include cardiomyocytes. For example, the cells may be hiPSC-CMs. In some embodiments, targeted cells may include non-cardiomyocytes.

The portion of the LAMP-2 gene targeted may vary based on the cell type. For example, LAMP-2B is the predominant LAMP-2 isoform expressed in cardiomyocytes. As such, in one example of a mouse model, genetic correction may be targeted to one or more mutations of the LAMP-2B isoform.

Correction of the LAMP-2 mutation rescues functional abnormalities in cardiomyocytes, for example in human cardiomyocytes. For example, correction of the LAMP-2 mutation in Danon hiPSC-CMs restored normal autophagy and mitochondrial function, as well as improved contractility. As such, LAMP-2B deficiency may cause the phenotypes observed in Danon cardiomyocytes.

Definitions

The term "CRISPR/Cas" or "clustered regularly interspaced short palindromic repeats" or "CRISPR" refers to DNA loci containing short repetitions of base sequences followed by short segments of spacer DNA from previous exposures to a virus or plasmid. Bacteria and archaea have evolved adaptive immune defenses termed CRISPR/CRISPR-associated (Cas) systems that use short RNA to direct degradation of foreign nucleic acids. In bacteria, the CRISPR system provides acquired immunity against invading foreign DNA via RNA-guided DNA cleavage.

The "CRISPR/Cas9" system or "CRISPR/Cas9-mediated gene editing" refers to a type II CRISPR/Cas system that has been modified for genome editing/engineering. It is typically comprised of a "guide" RNA (gRNA) and a non-specific CRISPR-associated endonuclease (Cas9). "Guide RNA (gRNA)" is used interchangeably herein with "short guide RNA (sgRNA)" or "single guide RNA (sgRNA). The sgRNA is a short synthetic RNA composed of a "scaffold" sequence necessary for Cas9-binding and a user-defined ~20 nucleotide "spacer" or "targeting" sequence which defines the genomic target to be modified. The genomic target of Cas9 can be changed by changing the targeting sequence present in the sgRNA.

The term "Cas nuclease" refers to the CRISPR-associated protein, a non-specific endonuclease. It is directed to the specific DNA locus by a gRNA, where it makes a double-strand break. There are several versions of Cas nucleases isolated from different bacteria. The most commonly used one is the Cas9 nuclease from *Streptococcus pyogenes*.

The terms "nucleic acid" and "oligonucleotide" may be used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a nucleotide has the same base-pairing specificity; i.e., an analogue of A will base-pair with T.

The term "induced pluripotent stem cells" (iPSCs) refers to cells having properties like those of embryonic stem cells (ESCs) and encompasses undifferentiated cells artificially derived by reprogramming differentiated, non-pluripotent cells, typically adult somatic cells.

The term "human induced pluripotent stem cell-derived cardiomyocytes" or "hiPSC-CMs" refers to hiPSCs differentiated into cardiomyocytes. hiPSCs can be differentiated into various disease-relevant cell types.

As described in greater detail herein, the present invention provides methods for treating Danon disease in a subject. The terms "treat", "treating", "treatment", etc., as applied to a cell, include subjecting the cell to any kind of process or condition or performing any kind of manipulation or procedure on the cell. As applied to a subject, the terms refer to providing a cell in which a target sequence has been modified ex vivo according to the methods described herein to an individual. The subject is usually ill or injured, or at increased risk of becoming ill relative to an average member of the population and in need of such attention, care, or management. For example, the subject may be suffering from Danon disease, and in need of such attention, care, or management.

As used herein, the term "treating" and "treatment" refers to administering to a subject an effective number of cells with target sequences modified ex vivo according to the methods described herein so that the subject has a reduction in at least one symptom of the disease or an improvement in the disease (e.g., Danon disease), for example, beneficial or desired clinical results. For purposes of this invention, beneficial or desired clinical results include, but are not limited to, alleviation of one or more symptoms, diminishment of extent of disease, stabilized (i.e., not worsening) state of disease, delay or slowing of disease progression, amelioration or palliation of the disease state, and remission (whether partial or total), whether detectable or undetectable. Treating can refer to prolonging survival as compared to expected survival if not receiving treatment. Thus, one of skill in the art realizes that a treatment may improve the disease condition but may not be a complete cure for the disease. As used herein, the term "treatment" includes prophylaxis. Alternatively, treatment is "effective" if the progression of a disease is reduced or halted. "Treatment" can also mean prolonging survival as compared to expected survival if not receiving treatment. Those in need of treatment include those already diagnosed with a disorder associated with expression of a sequence, as well as those likely to develop such a disorder due to genetic susceptibility or other factors.

By "treatment," "prevention" or "amelioration" of a disease or disorder is meant delaying or preventing the onset of such a disease (e.g., Danon disease), reversing, alleviating, ameliorating, inhibiting, slowing down or stopping the progression, aggravation or deterioration the progression or severity of a condition associated with such a disease or disorder. In one embodiment, the symptoms of a disease or disorder are alleviated by at least 5%, at least 10%, at least 20%, at least 30%, at least 40%, or at least 50%.

An exemplary method for treating or preventing a disorder associated with expression of a nucleotide sequence in a subject comprises altering a target nucleotide sequence in a cell by contacting the nucleotide sequence with a nuclease (e.g., a clustered regularly interspaced short palindromic repeats-associated (Cas) protein) and from one to two ribonucleic acids, wherein the ribonucleic acids direct the nuclease to, and hybridize to, a target motif of the target polynucleotide sequence, wherein the target polynucleotide sequence is cleaved, and modified, and introducing the modified cell into the subject, thereby treating a disorder associated with expression of the nucleotide sequence.

EXAMPLES

Example 1—Human Model Cell Line

Figure 8A:
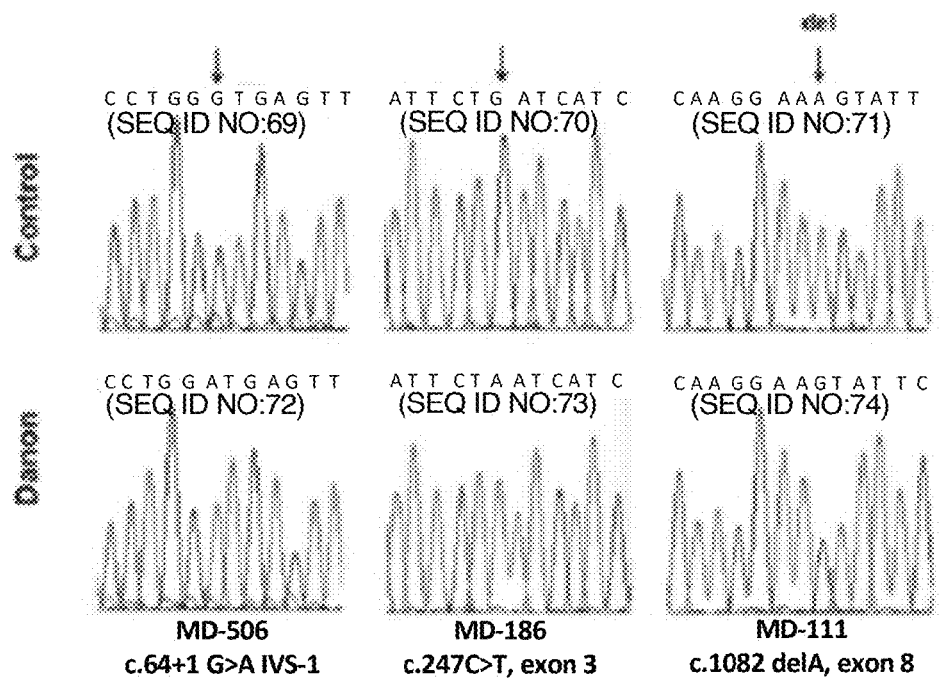
FIGS. 8A-M depict generation of hiPSCs and hiPSC-CMs.
Figure 8B:
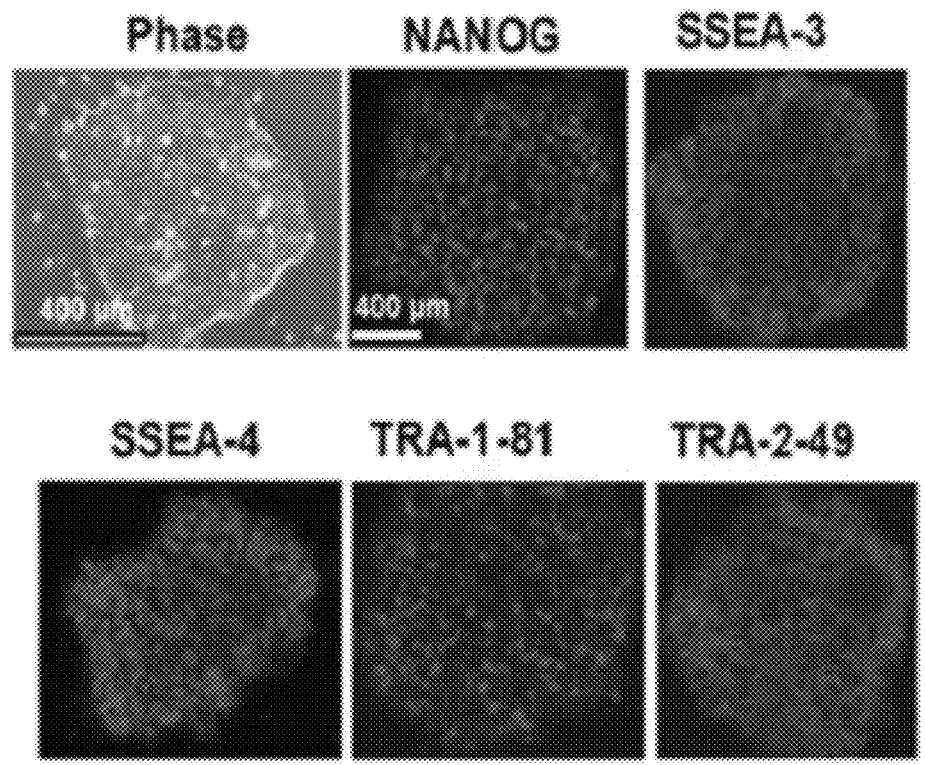
Figure 8C:
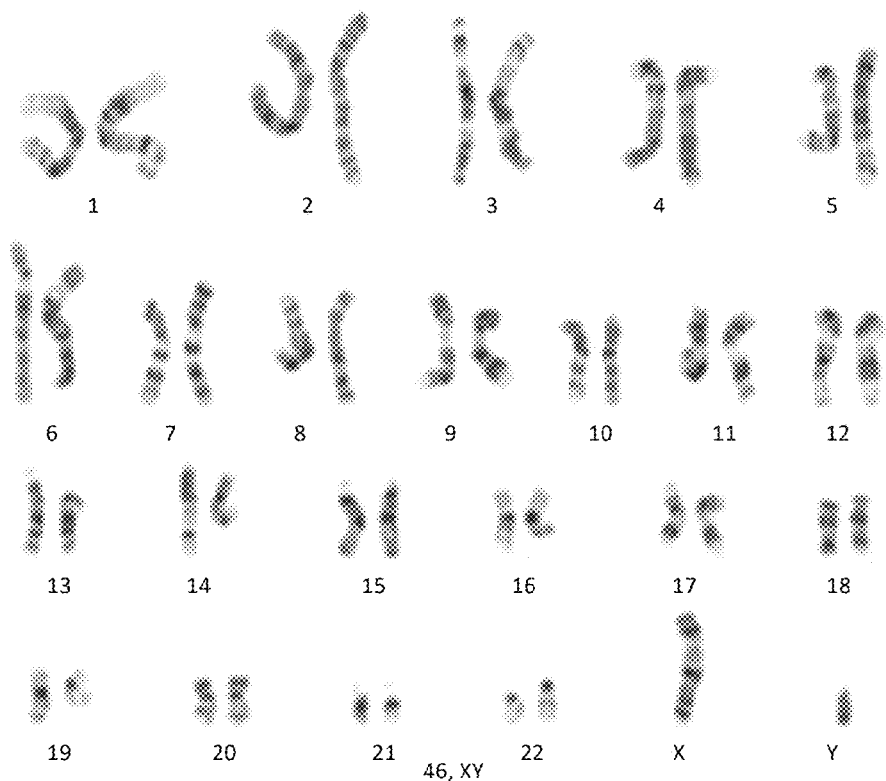
Figure 8D:
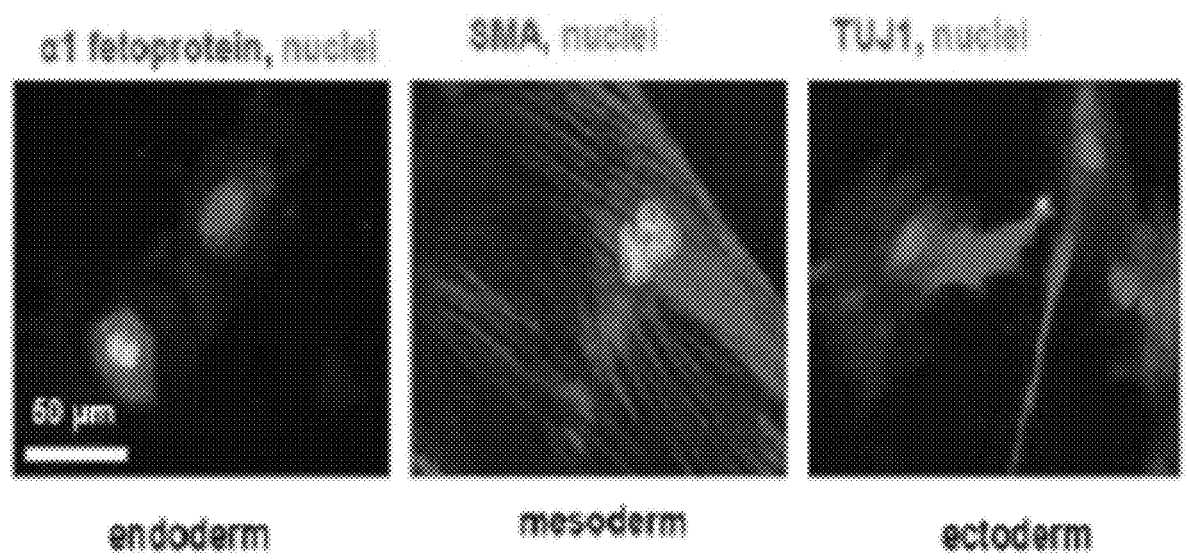
Figure 8E:
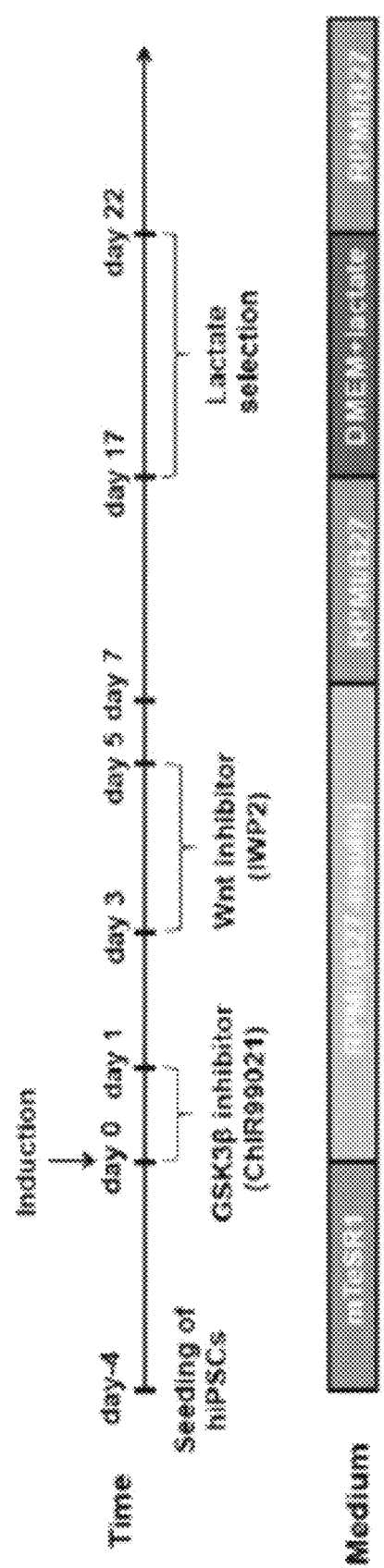
Figure 8F:
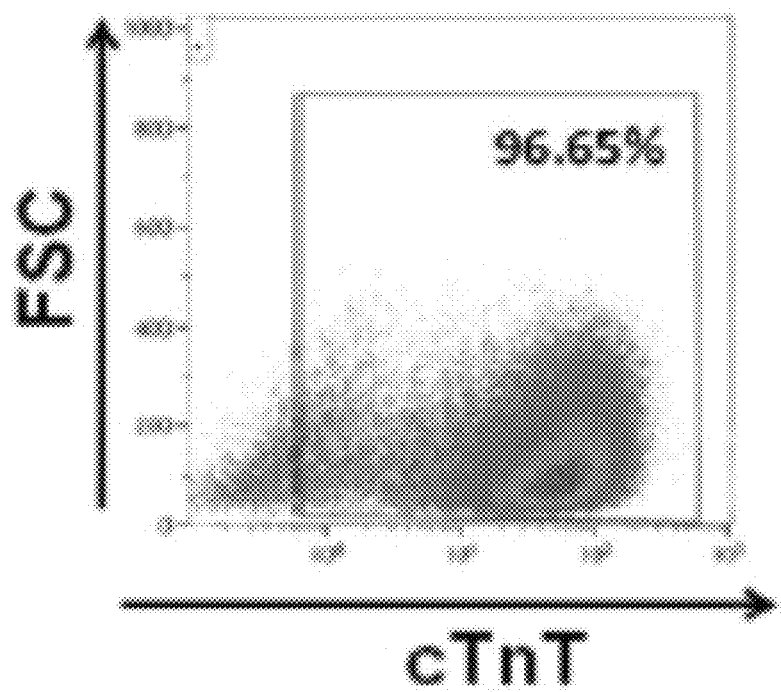
Figure 8G:
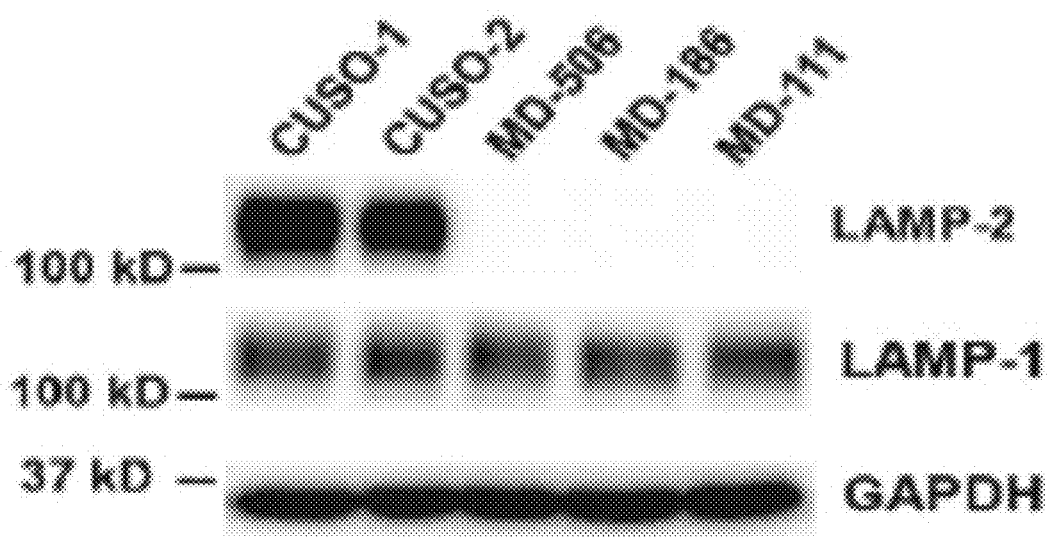
Figure 8H:
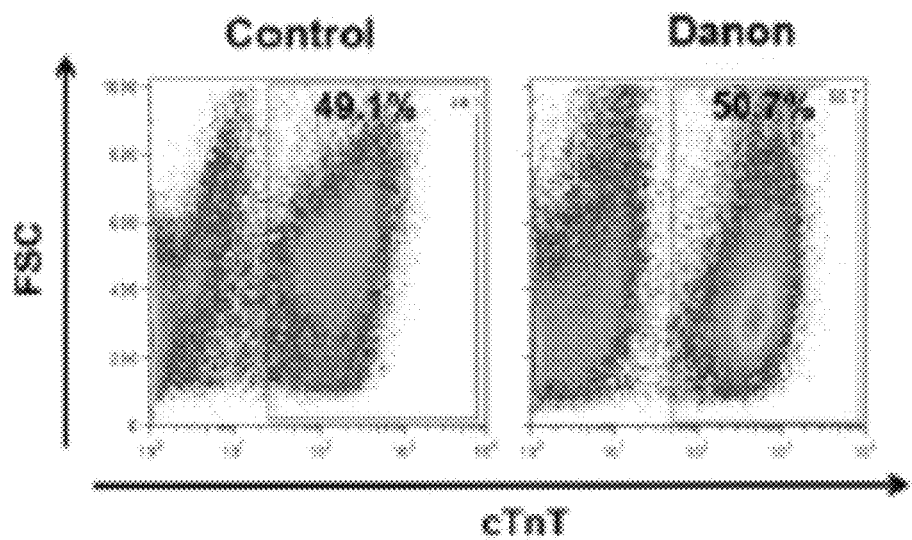
Figure 8I:
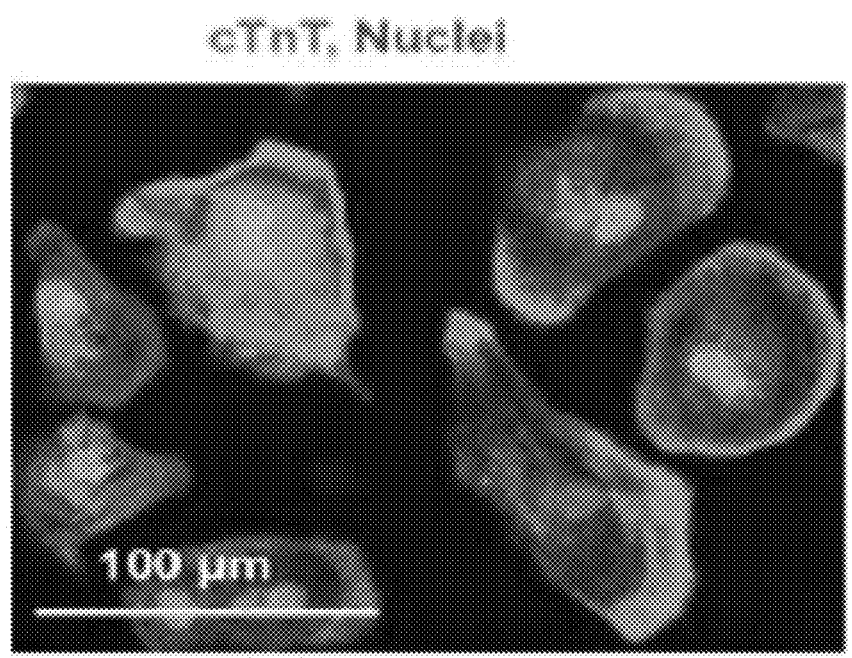
Figure 8J:
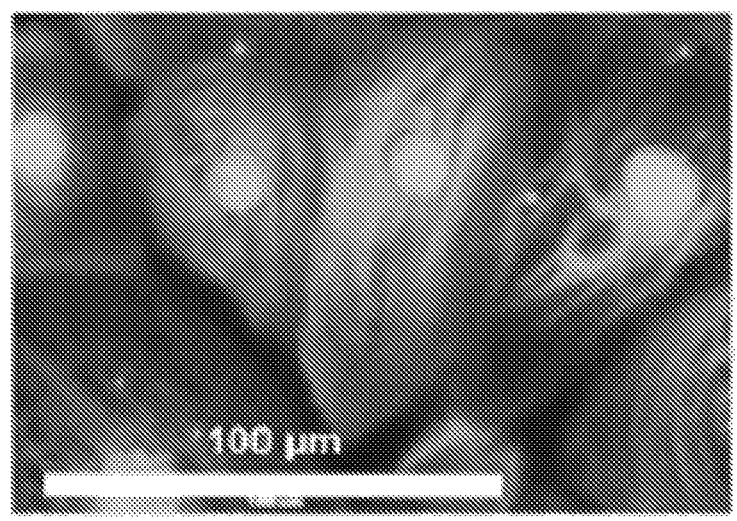
Figure 8K:
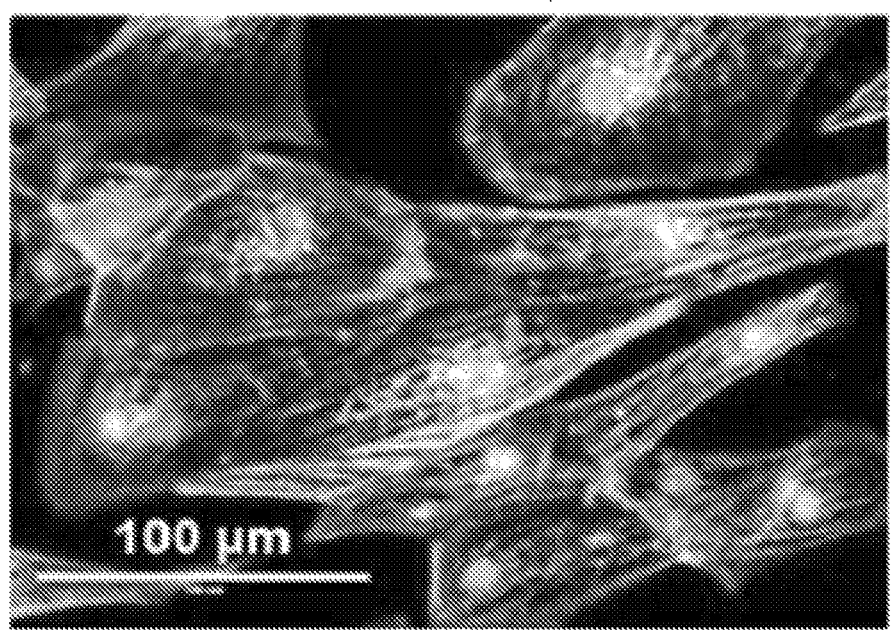
Figure 8L:
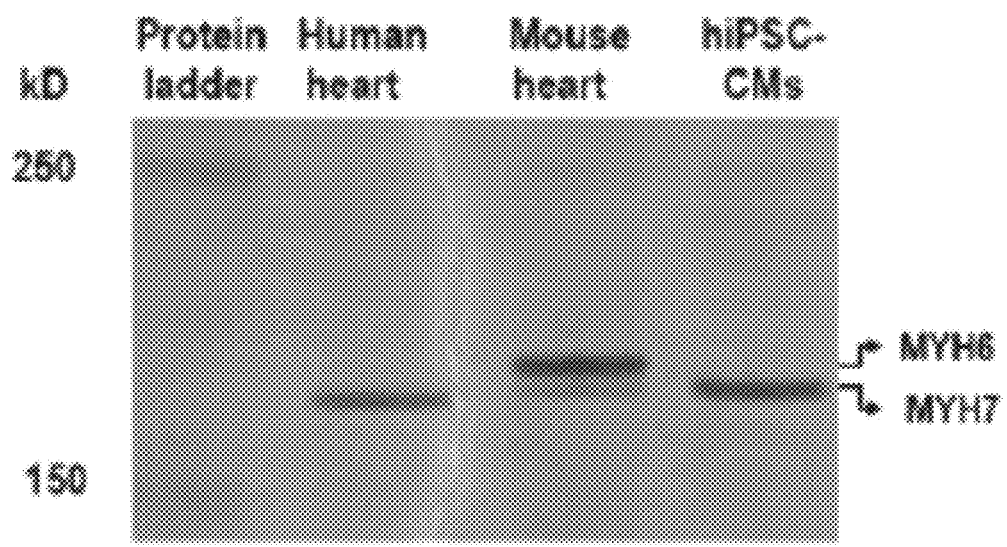
Figure 8M:
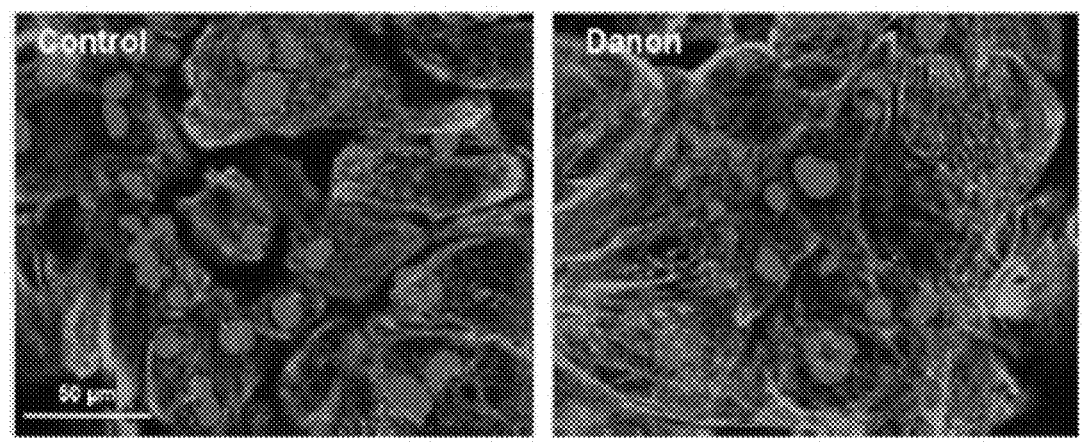

LAMP-2B may be the predominant LAMP-2 isoform expressed in human and mouse cardiomyocytes. While half of LAMP-2 knockout mice displayed an almost normal life span, patients with Danon disease are susceptible to cardiac death or need heart transplantation at a young age, suggesting species-specific effects on pathogenesis of Danon disease. To investigate these mechanisms in a human model, human-induced pluripotent stem cells ("hiPSCs") were generated from skin fibroblasts derived from two unrelated control males (hereafter referred to as CUSO-1 and CUSO-2) and three unrelated males with Danon disease (hereafter referred to as MD-111, MD-186, and MD-506). The three patients, MD-111, MD-186, and MD-506, carried LAMP-2 frameshift (c. 1082 delA, exon 8; deletion of A at position 1082 in exon 8), nonsense (c.247C>T, exon 3; mutation of C to Tat position 247 in exon 3), and splicing (c.64+1 G>A IVS-1; mutation of G to A mutation at position 64 in Intervening Sequence 1) mutations, respectively (See, FIG. 8A and Table 1). In many embodiments, a LAMP2 gene comprising one or more of these mutations may be referred to as mutant LAMP2 gene. The non-mutant human LAMP-2 sequences are available as at accession no. NM_002294.3 (human WT LAMP-2A) and NM_013995.2 (human WT LAMP-2B), available at www.ncbi.nlm.nih.gov. These hiPSC lines had normal karyotypes and demonstrated pluripotency by expressing pluripotency markers and capacity to differentiate into derivatives of three germ layers (See, FIGS. 8 B-D). Human induced pluripotent stem cell-derived cardiomyocytes (hiPSC-CMs) were generated with greater than 90% purity from each line for subsequent studies using established protocols (See, FIGS. 8 E and F). LAMP-2 protein was not detectable in Danon hiPSC-CMs (See, FIG. 8G), consistent with previous results that mutations in the LAMP-2 gene led to complete LAMP-2 deficiency in patients with Danon disease could be due to a nonsense mediated RNA decay (NMD) mechanism. Differentiation of Danon hiPSCs into hiPSC-CMs was not significantly different from control lines (See, FIG. 8H). Monolayer hiPSC-CMs expressed cardiomyocyte markers (See, FIGS. 8 I-K) and beat spontaneously. These hiPSC-CMs expressed a high ratio of MYH7 to MYH6, comparable to human heart tissues (See, FIG. 8L). α-Actinin-positive sarcomeric structures in Danon hiPSC-CMs were comparable to those in controls (See, FIG. 8M). hiPSC-CMs on day ~50 after induction were used in this study if the time point was otherwise not specified.

The disclosed compositions, methods, techniques, protocols, and systems may be useful in treating a variety of LAMP-2 genetic mutations in mammalian subjects. As described below, the compositions, methods, techniques, protocols, and systems can be used to treat coding and non-coding mutations, including frameshift, nonsense, splicing mutations etc. In some embodiments, the mutations may be one or more of a deletion of A at position 1082 in exon 8, a mutation of C to T at position 247 in exon 3, or a mutation of G to A mutation at position 64 in Intervening Sequence 1. In some embodiments, the mutation corrected by the disclosed compositions, methods, protocols, techniques, and systems may be one or more of the mutations described in FIG. 21, which also describes guide RNAs and corrective nucleic acid sequence.

Figure 9A:
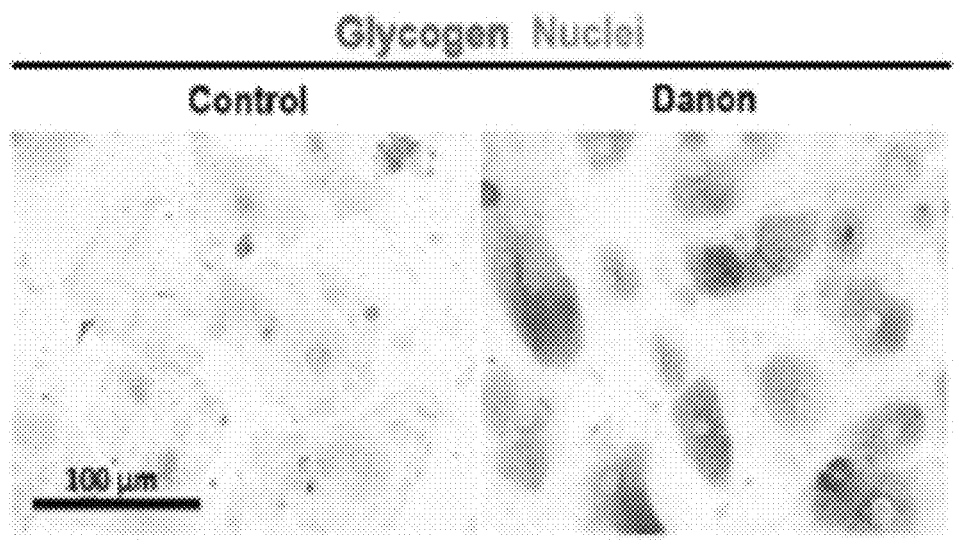
FIGS. 9A-E depict glycogen, vacuoles, and apoptosis in Danon hiPSC-CMs.
Figure 9B:
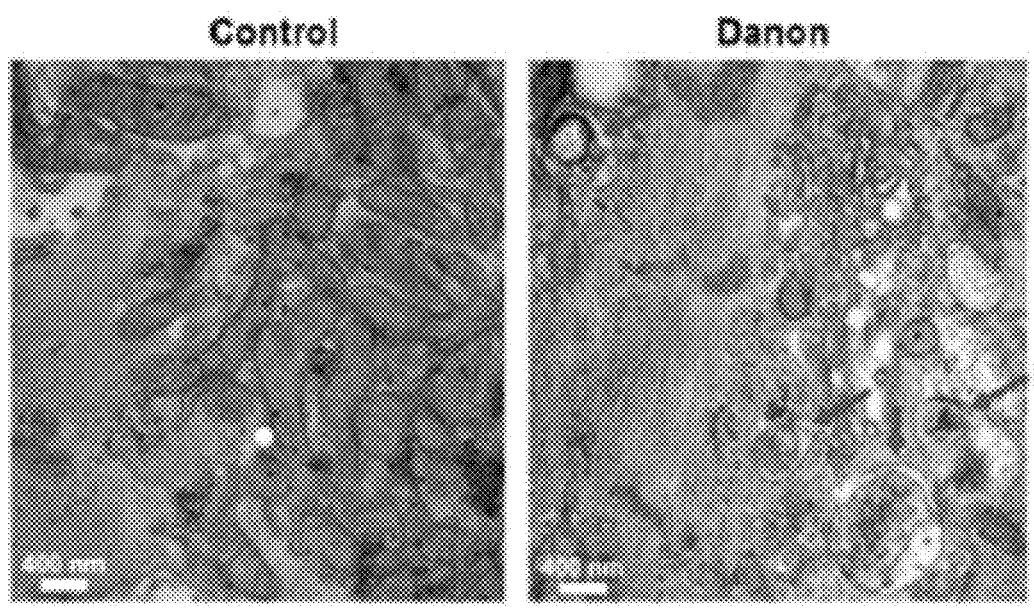
Figure 9C:
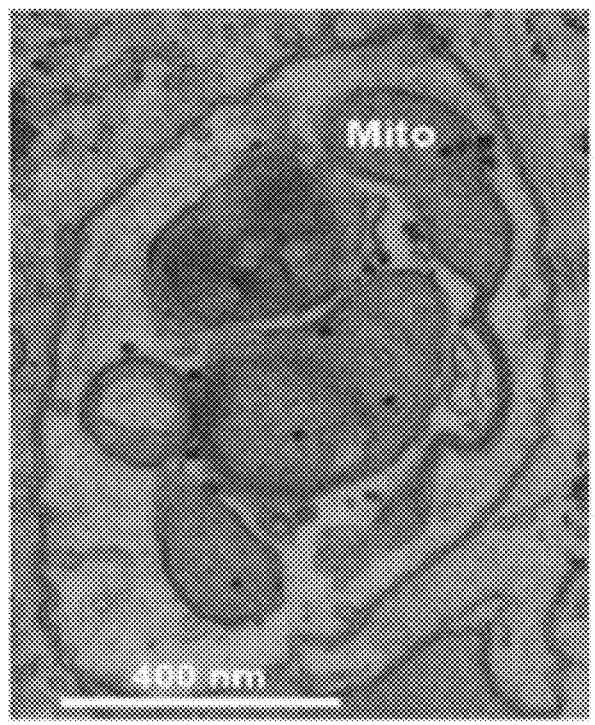
Figure 9E:
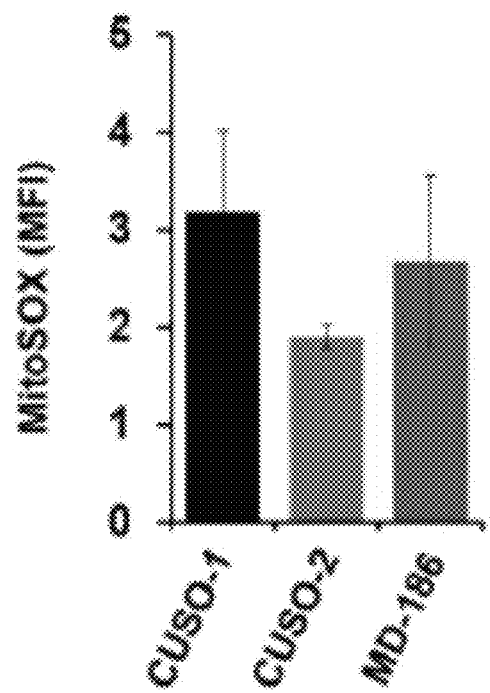
Figure 9D:
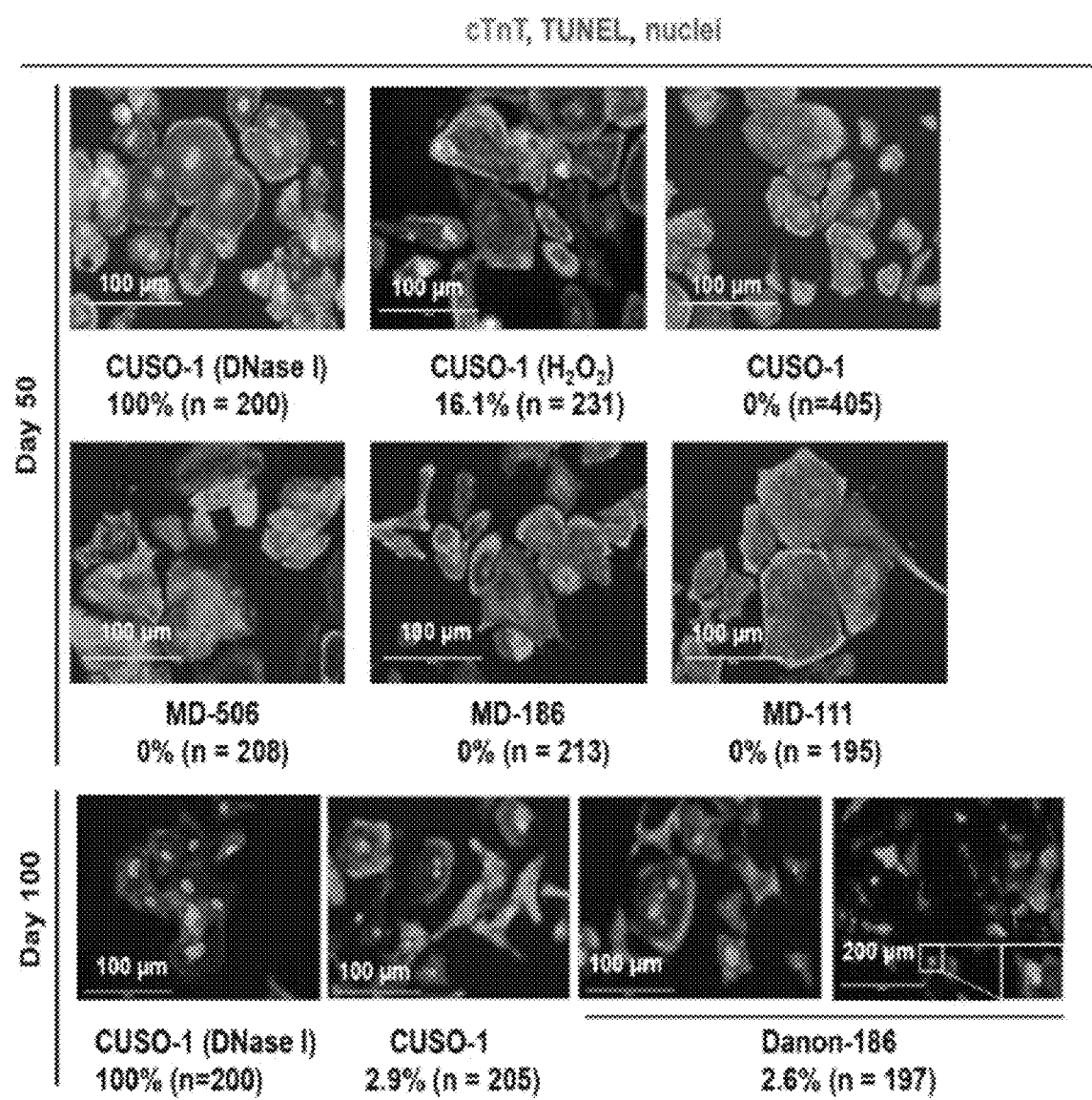

A pathological indicator of Danon disease is accumulation of glycogen and vacuoles in the patient's cardiomyocytes. Compared with control hiPSC-CMs, Danon hiPSC-CMs displayed increased Periodic Acid-Schiff stain (PAS)-positive glycogen storage and accumulation of vacuoles (See, FIGS. 9A-C), suggesting that this hiPSC-CM platform is appropriate to characterize the mechanisms. Consistent with a previous study, no significant increase in apoptosis, as assayed by TUNEL staining, was observed in any examined Danon hiPSC-CM line cultured for either 50 or 100 days, compared with controls (See, FIG. 9D). In addition, levels of reactive oxygen species (ROS) assayed by MitoSOX in Danon hiPSC-CMs were comparable to those in control hiPSC-CMs (See, FIG. 9E). LAMP-2 deficiency may not induce apoptosis in Danon hiPSC-CMs.

Example 2—Lamp-2 Expression and Deficiency

Figure 1B:
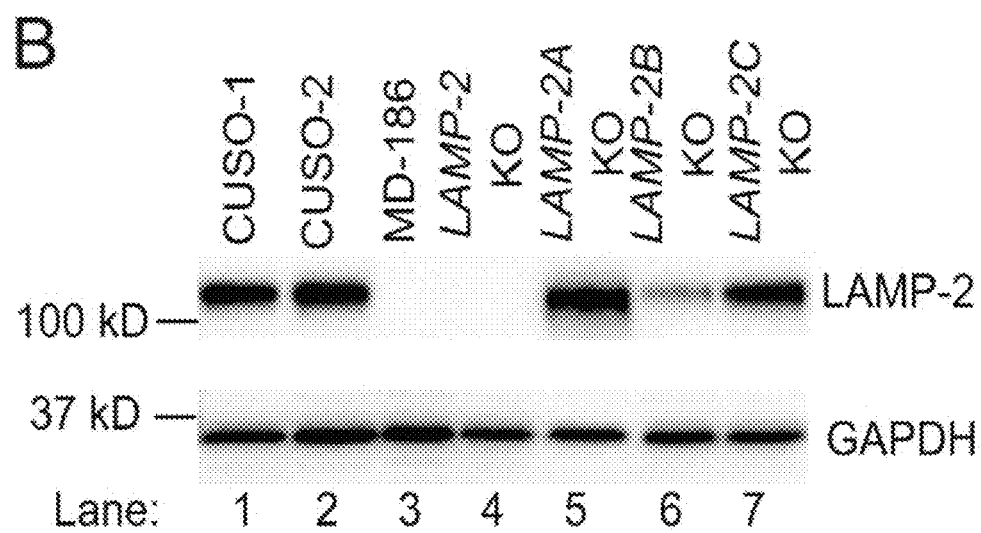
Figure 10A:
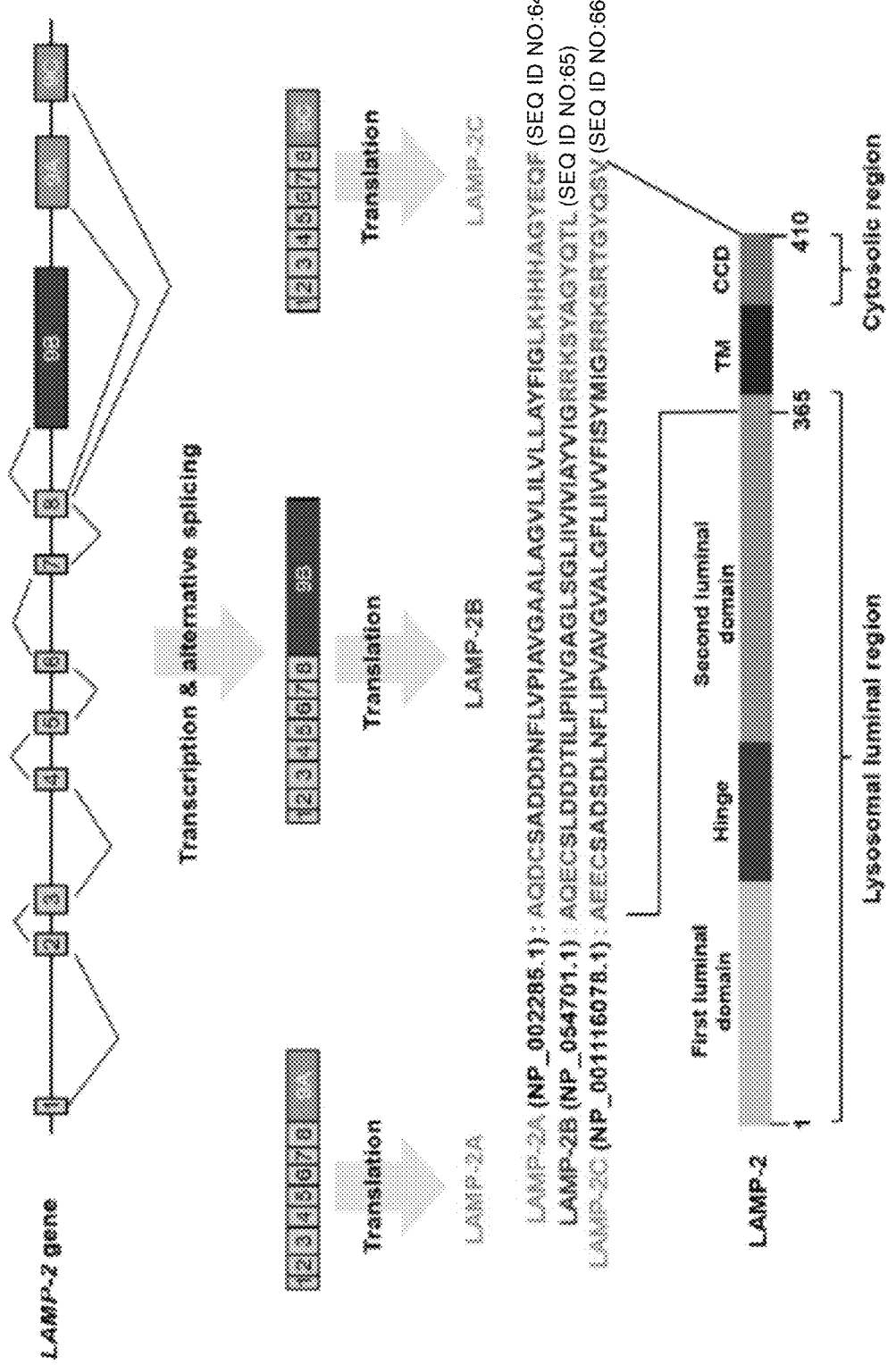
FIGS. 10A-C depict that LAMP-2B is the predominant LAMP-2 isoform expressed in mouse cardiomyocytes.
Figure 10B:
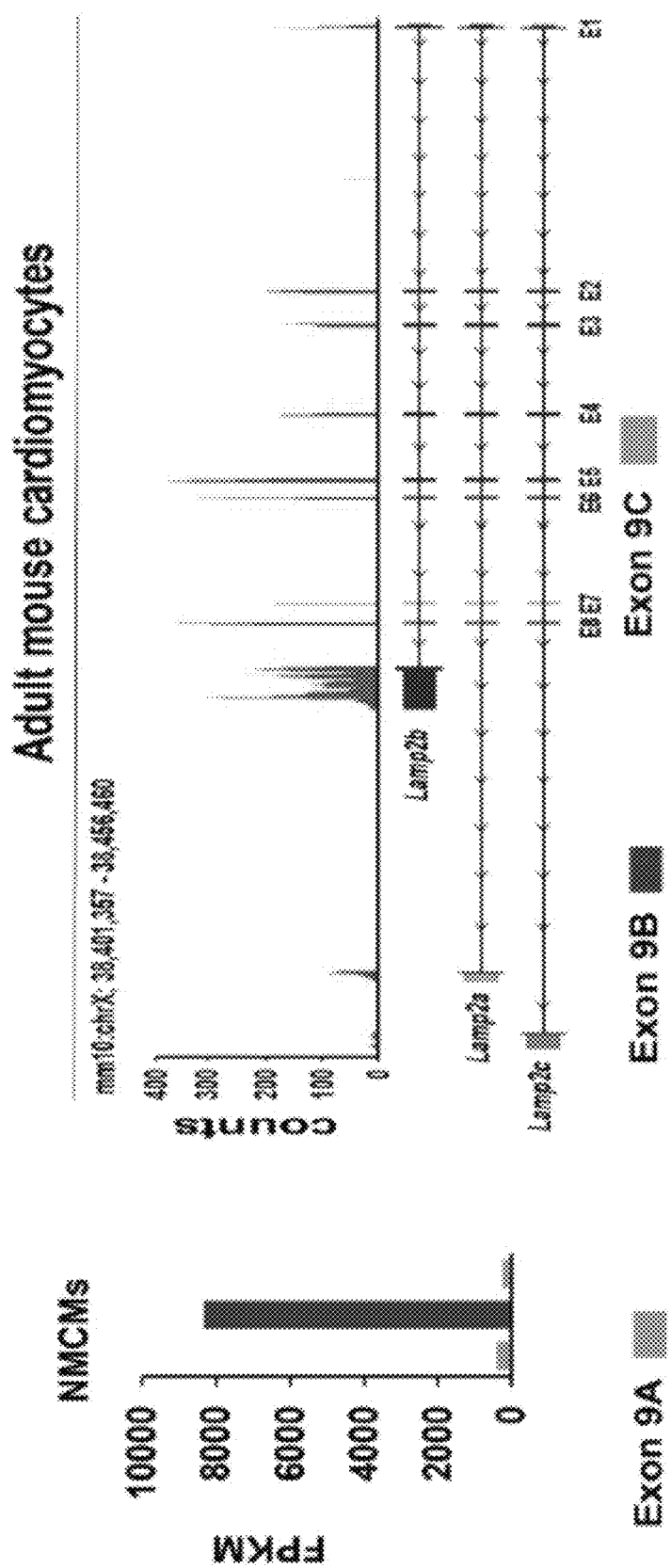

The three LAMP-2 isoforms, LAMP-2A, LAMP-2B, and LAMP-2C, share an identical lysosomal domain at their N terminus, but have distinct transmembrane and C-terminal cytosolic domains composed of 11 amino acids (See, FIG. 10A). RNA-seq and real-time PCR (qPCR) analysis demonstrated that LAMP-2B was expressed in both human and mouse cardiomyocytes (See, FIG. 1A and FIG. 10B). In contrast, LAMP-2A was enriched in non-CMs such as HEK293, HeLa, and human skin fibroblasts (FIG. 1A). To examine biological functions of LAMP-2 in human cardiomyocytes, CRISPR/Cas9 genome editing technology was used to generate isogenic LAMP-2 knockout (LAMP-2 KO) hiPSC lines by deleting exon 2 in the control CUSO-1 hiPSC line, as well as LAMP-2 isoform specific knockout lines, LAMP-2A KO, LAMP-2B KO, and LAMP-2C KO, in the control CUSO-2 hiPSC line by targeting exon 9A, exon 9B, and exon 9C, respectively (See, e.g., FIGS. 11A-I). The LAMP-2 KO hiPSC line contains a frameshift mutation and does not express LAMP-2 protein (FIG. 1B). Use of these isogenic hiPSC-CM lines can avoid the interference of

TABLE 1

Clinical features of patients in this study

Figure 10C:
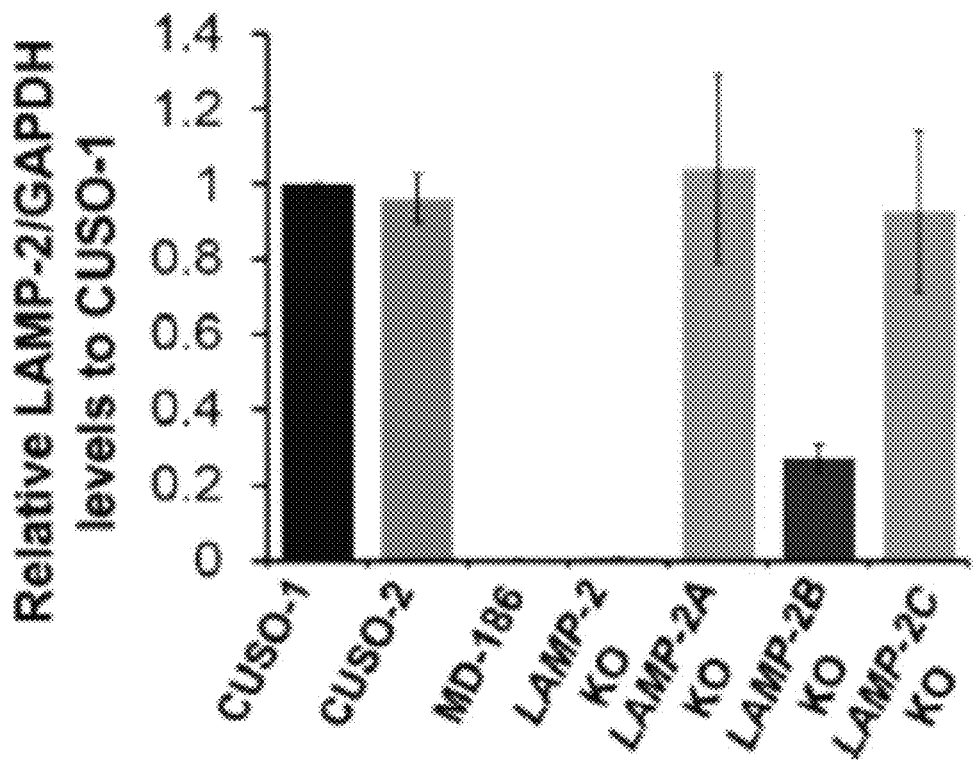
Figure 11A:
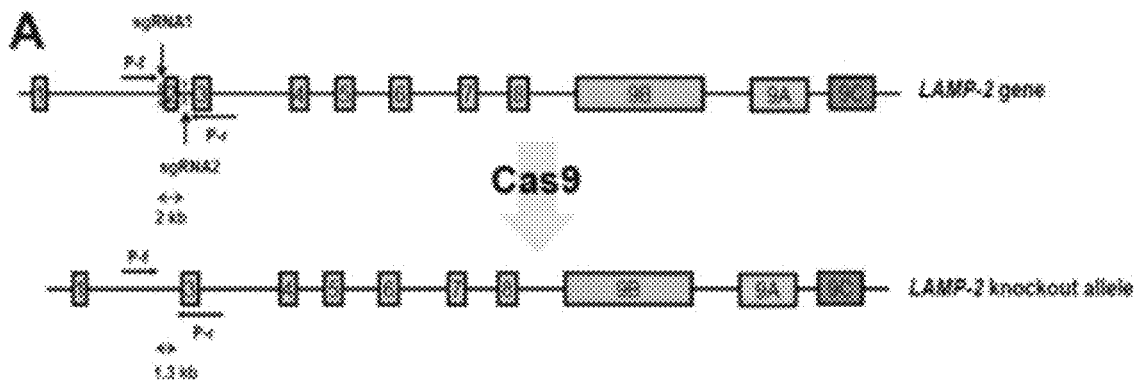
Figure 11F:
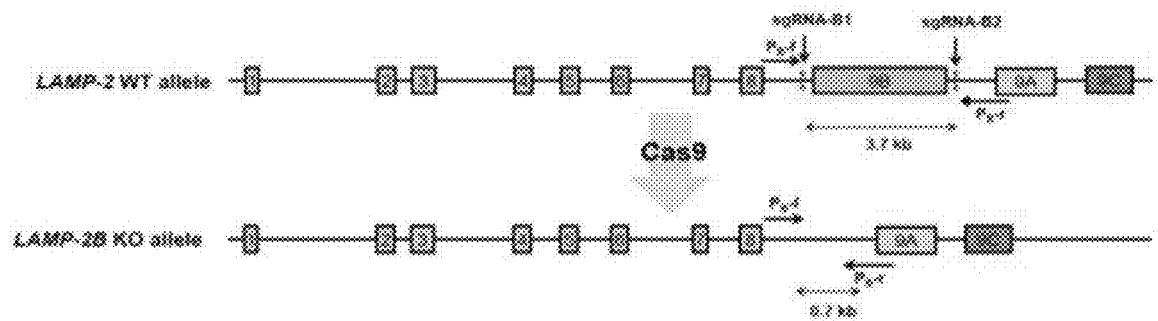
Figure 11G:
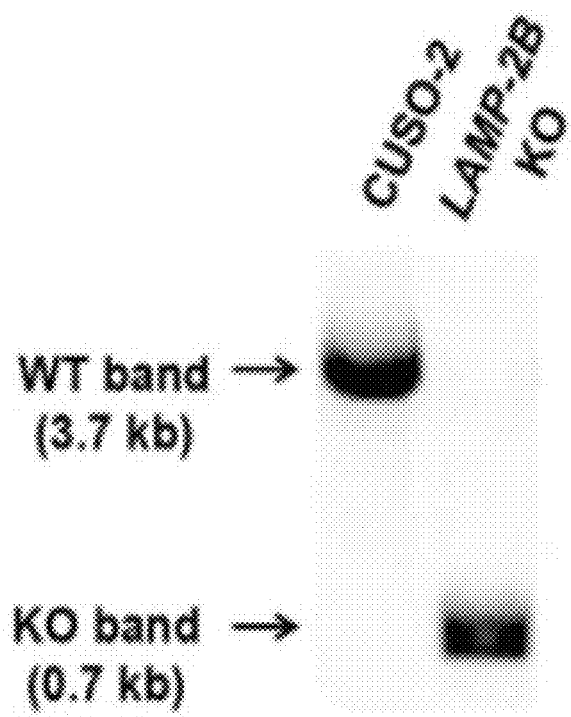
Figure 11H:
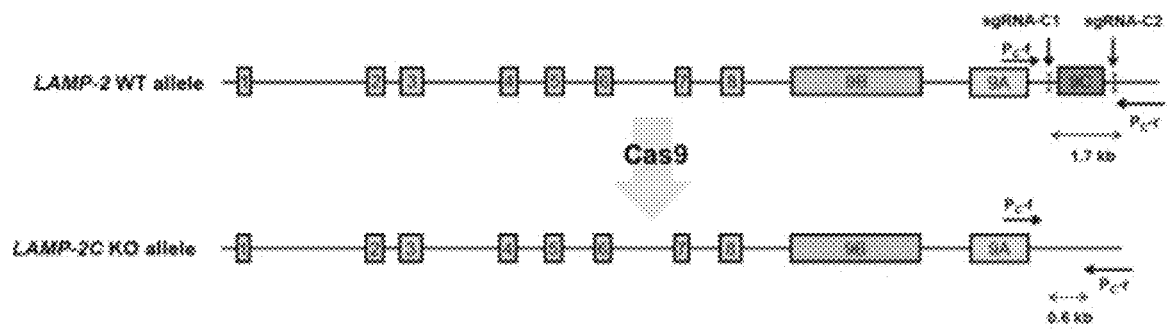
Figure 11I:
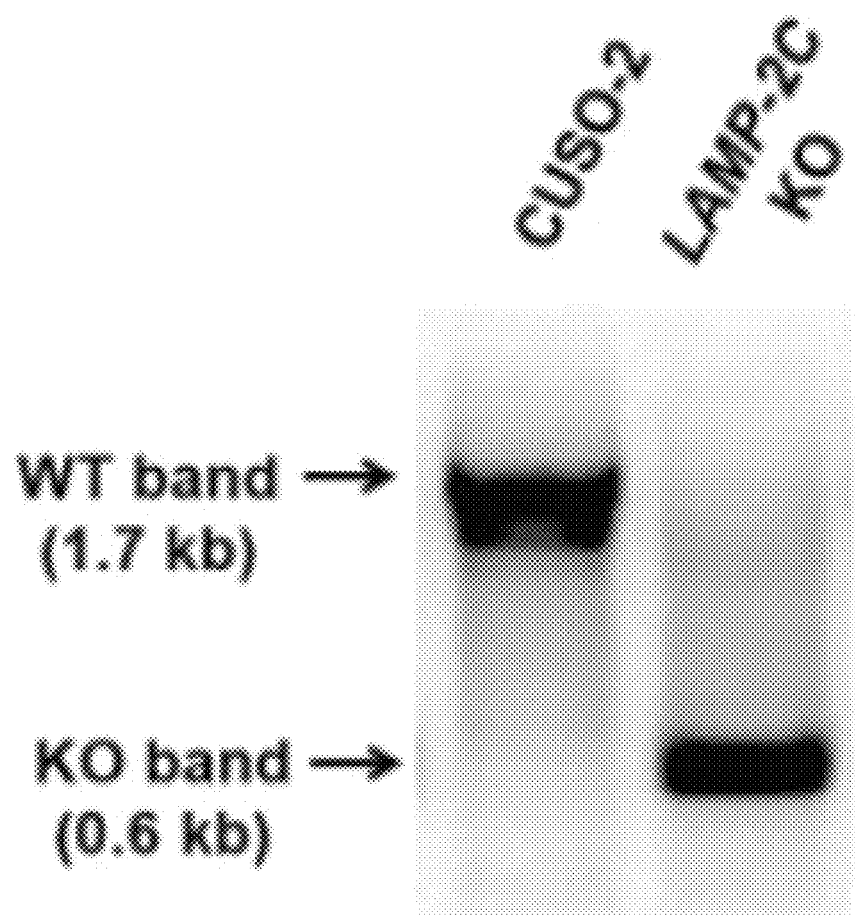

| | | Patient ID | | | |
|---|---|---|---|---|---|
| | | CUSO-1 | CUSO-2 | MD-111 | MD-186 | MD-506 |
| Symptom onset in years | | NA | NA | 14 | 15 | 7 |
| Heart | Heart disease | No | No | Yes | Yes | Yes |
| | ECHO AE | NA | NA | 18 | 25 | 11 |
| | Findings | NA | NA | Severe LV hypertrophy,; IVSd: 1.87 cm, LVPWd: 1.80 cm; LVIDd: 5.62-cm; EF 30% | Moderate LV hypertrophy; IVSd: 1.10 cm; LVPWd: 1.0 cm; LVIDd: 5.5 cm EF 30% | Mild LV hypertrophy; EF normal |
| | EKG AE | NA | NA | 18 | 25 | 11 |
| | Findings | NA | NA | WPW, LVH(v) | WPW | WPW, arrhythmias |
| | Heart transplant (age in years) | NA | NA | Yes (19) | Yes (27) | No (15) |
| Skeletal muscle | | Normal | Normal | Muscle weakness | Muscle weakness | Muscle weakness |
| Cognition | | Normal | Normal | Mild cognitive difficulties | Require special education | Require special education |
| Eye | | Normal | Normal | Blurry vision | Pigmentary retinopathy | Mild astigmastism | genetic background in elucidating the functions of LAMP-2 isoforms. In hiPSC-CMs, deletion of the LAMP-2B isoform decreased total LAMP-2 protein expression by more than 70%. The total LAMP-2 protein levels in LAMP-2A KO and LAMP-2C KO hiPSC-CMs were comparable to that in wild-type hiPSC-CMs (See, FIG. 1B and FIG. 10C).

Figure 12A:
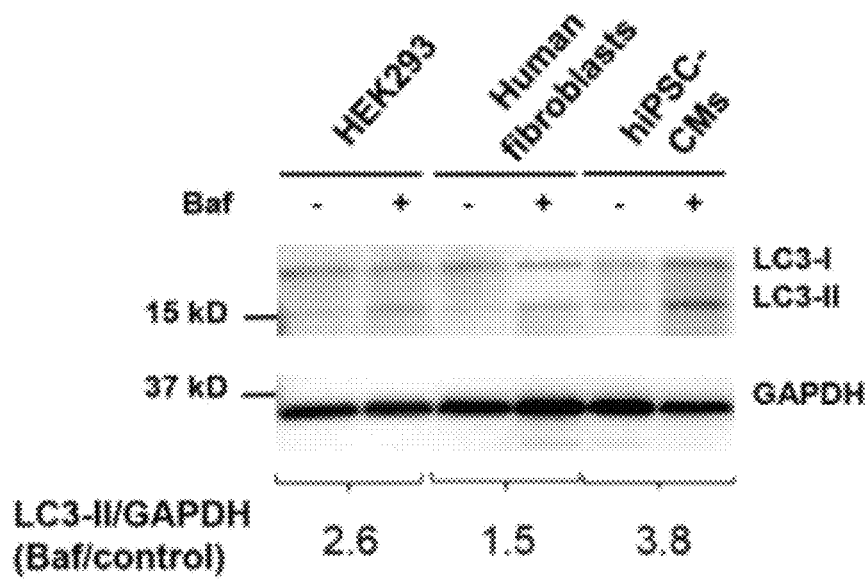
Figure 12B:
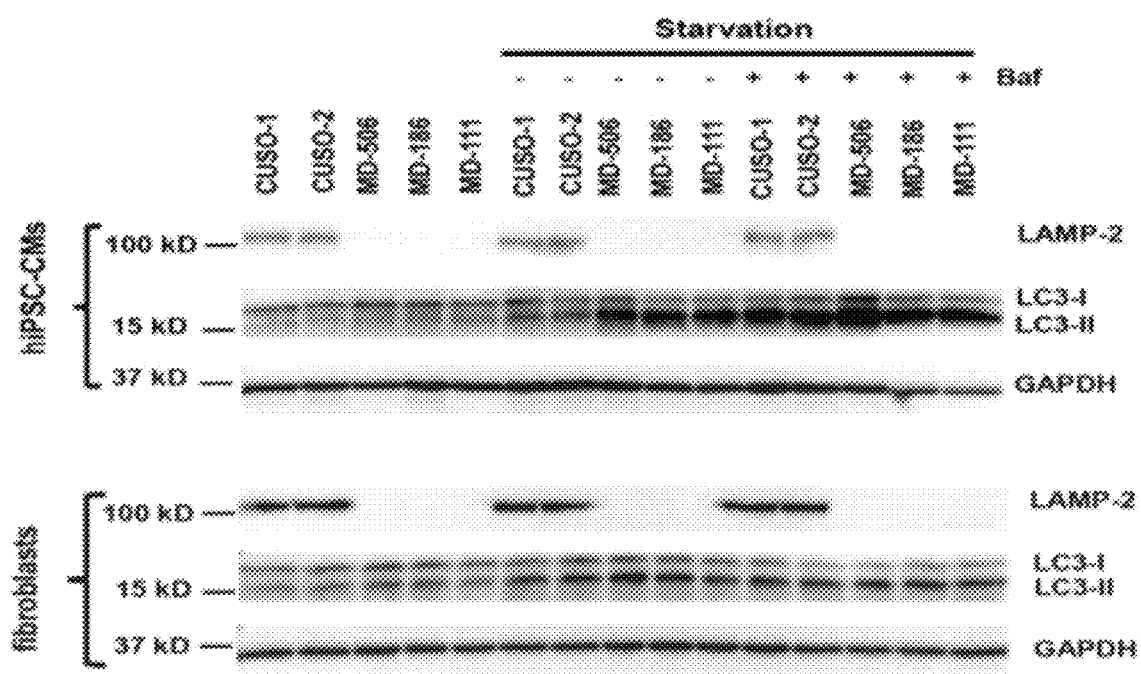

Deletion of all three LAMP-2 isoforms in mice caused accumulation of autophagosomes. Levels of microtubule-associated protein light chain 3 (LC3), and LC3-II, the membrane form of LC3 and an autophagosomal marker, were determined by immunoblotting. The amount of LC3-II is correlated with autophagosome number (1). Levels of LC3-II were similar in HEK293, human fibroblasts, and hiPSC-CMs under regular conditions, whereas addition of bafilomycin A1, a blocker of autophagosome-lysosome fusion and/or lysosomal degradation, increased LC3-II levels more in hiPSC-CMs than in HEK293 and human fibroblasts (See, FIG. 12A), suggesting that autophagic turnover occurs at a faster rate in human cardiomyocytes. Thus, the hiPSC-CM platform is a suitable model to study autophagy. Compared with control hiPSC-CMs, Danon and LAMP-2 KO hiPSC-CMs exhibited increased levels of LC3-II, especially under starvation conditions (See, FIGS. 12 B-E). LC3-II levels in skin fibroblasts derived from Danon patients were comparable to those in controls (See, FIG. 12B), indicating that autophagosomes in cardiomyocytes might be removed by mechanisms distinct from those in fibroblasts. Consistent with immunoblotting, greater numbers of LC3 puncta, which represent autophagosomes or related membrane structures, accumulated in Danon hiPSC-CMs under starvation conditions (See, FIG. 12F). LAMP-2 deficiency may cause accumulation of autophagosomes in human cardiomyocytes, as observed in LAMP-2 KO mice-LAMP-2B deficiency led to accumulation of LC3-II in hiPSC-CMs, whereas LAMP-2A or LAMP-2C deficiency did not (See, FIG. 2A and FIG. 12G). Levels of LC3-II in LAMP-2B KO hiPSC-CMs were comparable to those in Danon and LAMP-2 KO hiPSC-CMs (See, FIG. 2B and FIG. 12H, lanes 3, 4, 5, 8, 9, and 10).

Example 3—Rescue Experiments

Rescue experiments were performed using LAMP-2B KO hiPSC-CMs with adenovirus carrying either LAMP-2A or LAMP-2B. Different viral vectors may be used in the disclosed technology. For example, in some implementations, the guide RNA molecule, the Cas9 protein, and the template nucleic acid are introduced into cell with an adenovirus virus. In some implementations, the guide RNA molecule, the Cas9 protein, and the template nucleic acid are introduced into cell with an adeno-associated virus (AAV).

Figure 13A:
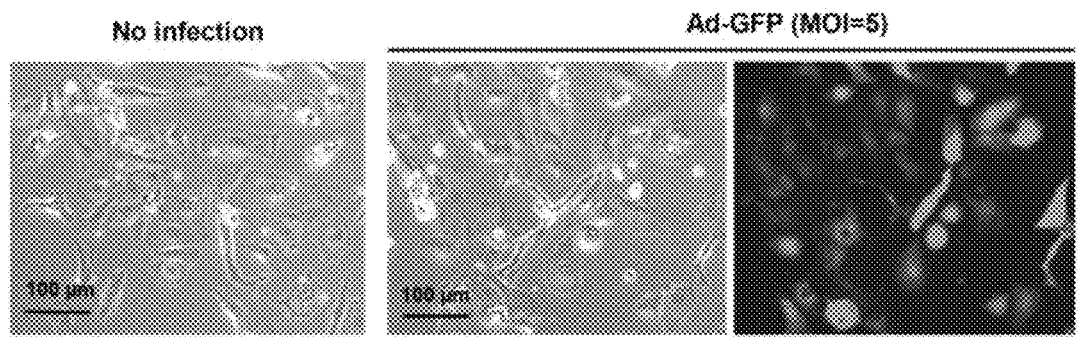
FIGS. 13A-B depict an overexpression of LAMP-2B in hiPSC-CMs using an adenoviral vector.
Figure 13B:
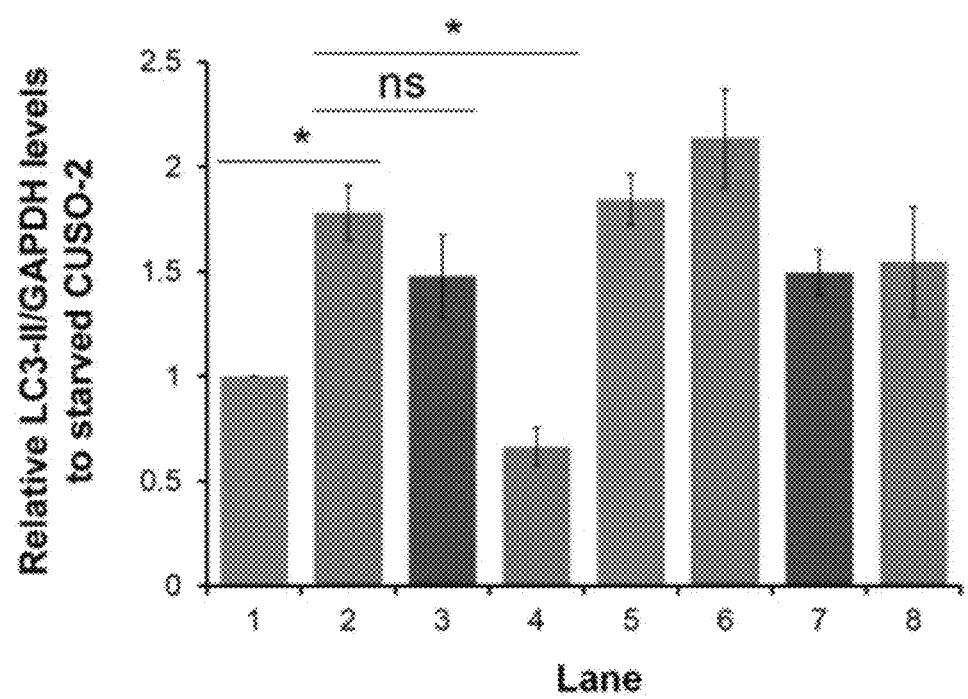

Adenoviral infection did not change hiPSC-CM morphology (See, FIG. 13A). Forced expression of LAMP-2B suppressed the LC3-II accumulation caused by LAMP-2B deficiency. In contrast, overexpression of LAMP-2A did not decrease LC3-II accumulation (See, FIG. 2C and FIG. 13B, lanes 2-4). LAMP-2B, but not LAMP-2A or LAMP-2C, may be involved for autophagy in human cardiomyocytes.

Example 4—Autophagosome Studies

This accumulation of autophagosomes may be due to increased induction of autophagy and/or blocked autophagosome-lysosome fusion. To distinguish between these possibilities, autophagic flux assays were performed by using a mRFP-GFP-LC3 tandem construct where the GFP signal can be quenched by the acidic lysosomal pH. Thus, autophagosomes are marked by both RFP and GFP signals (yellow). After fusion with lysosomes to become autolysosomes, only RFP signals (red) could be observed. If induction of autophagy increased, both yellow puncta and red puncta are increased. However, if fusion between autophagosomes and lysosomes was blocked, only yellow punctae increased. Danon and LAMP-2B KO hiPSC-CMs showed more yellow puncta, but fewer red puncta compared with control hiPSC-CMs under both regular and starved conditions (FIGS. 2 D and E), indicating that autophagosome fusion/maturation into autolysosome was blocked in Danon or LAMP-2B KO hiPSC-CMs. However, a similar fraction of autolysosomes was observed in Danon and LAMP-2B KO hiPSC-CMs (FIGS. 2 D and E), suggesting LAMP-2B-independent autophagic fusion mechanisms in cardiomyocytes. Second, autophagic flux was measured by immunoblotting analysis of LC3-II. When autophagic fusion was blocked by bafilomycin A1 in hiPSC-CMs under regular or starved conditions, levels of LC3-II in Danon or LAMP-2B KO hiPSC-CMs were similar to those in control hiPSC-CMs (FIG. 2 A-C), indicating normal induction of autophagic flux. Knockout of LAMP-2B in hiPSC-CMs caused a reduction in colocalization of LC3 puncta with LysoTracker-labled late endosomes/lysosomes assayed by confocal imaging, which was also observed in Danon hiPSC-CMs (FIGS. 2 F and G). LAMP-2B deficiency in cardiomyocytes may cause accumulation of autophagosomes by blocking autophagosome-lysosome fusion.

Figure 3A:
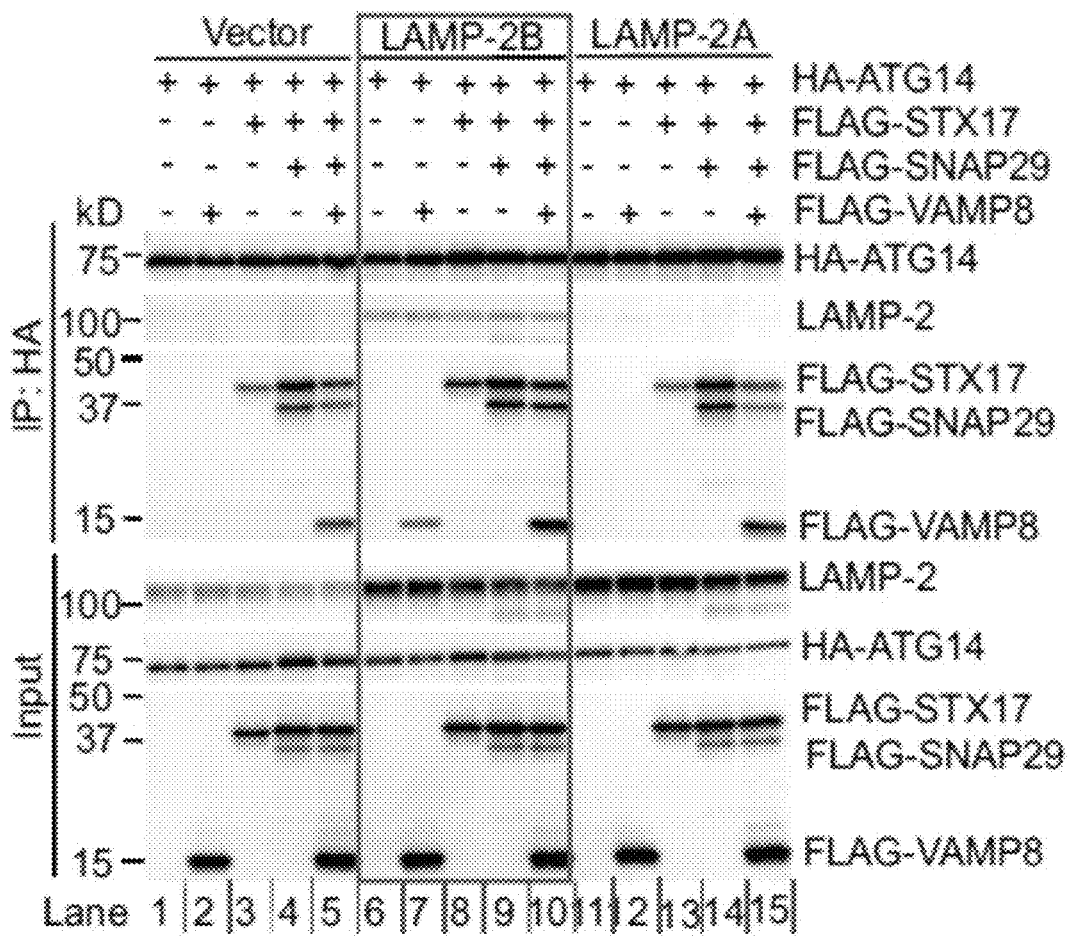
FIGS. 3A-F depicts that the CCD of LAMP-2B is involved to promote formation of the ATG14-VAMP8 complex.
Figure 3B:
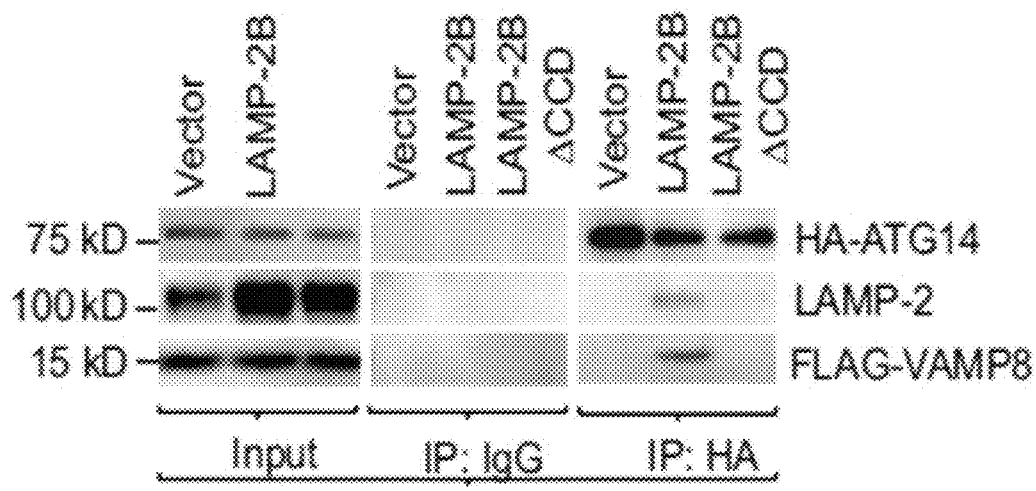
Figure 3C:
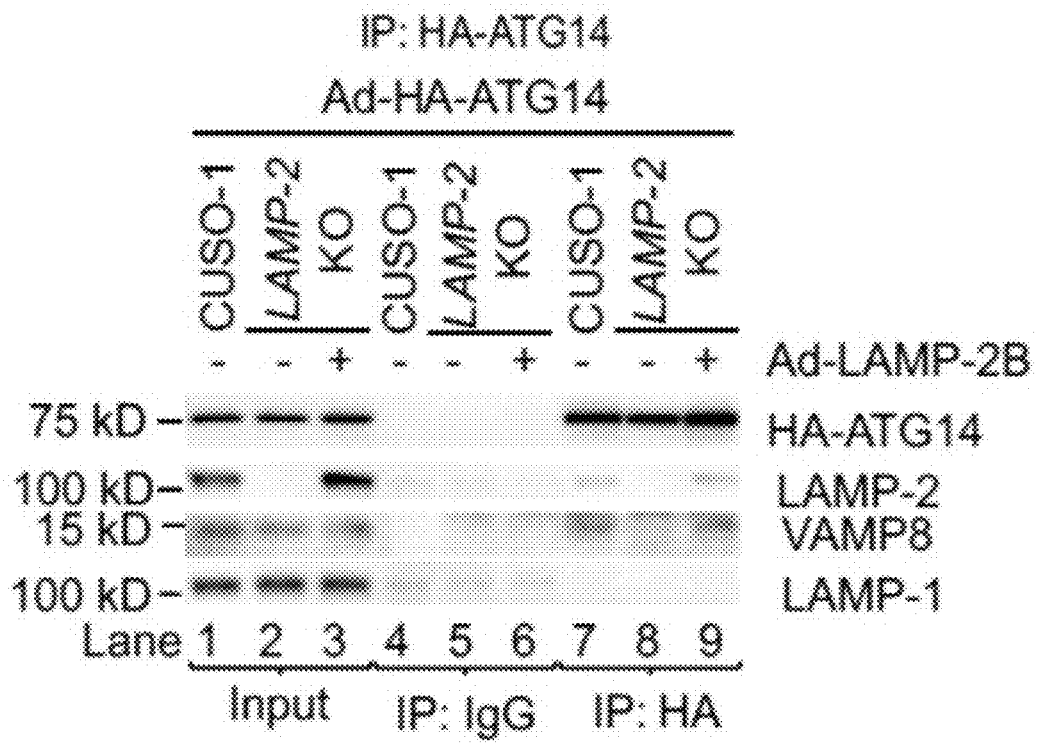
Figure 3D:
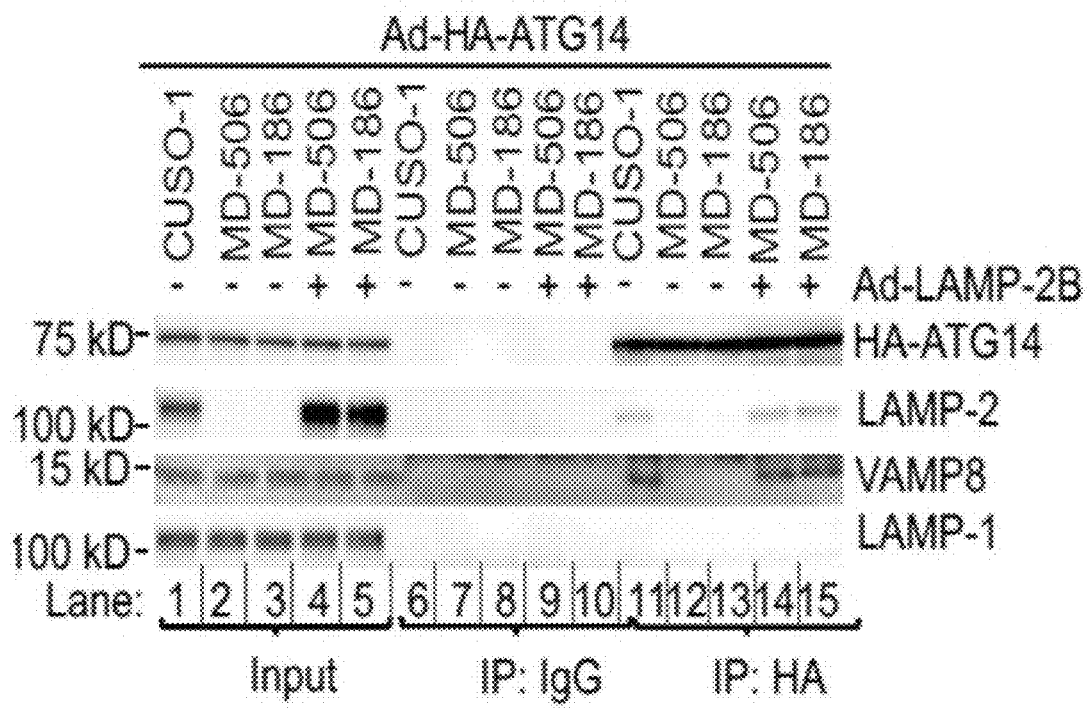
Figure 3E:
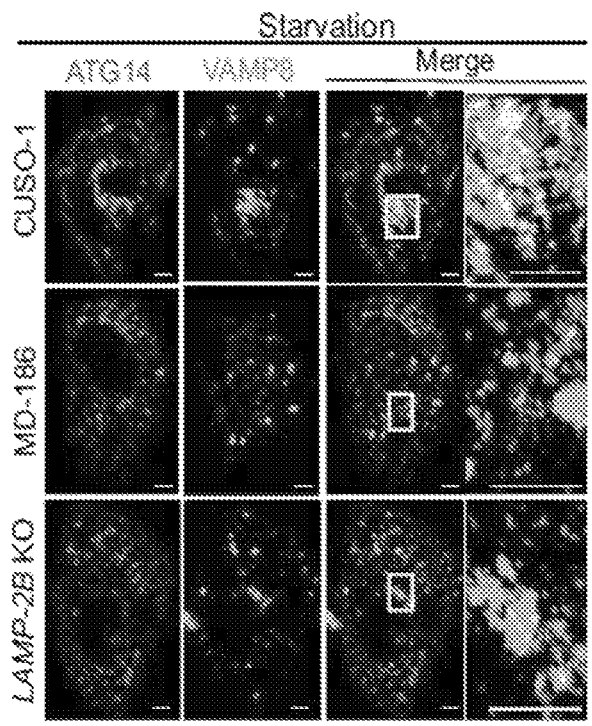
Figure 3F:
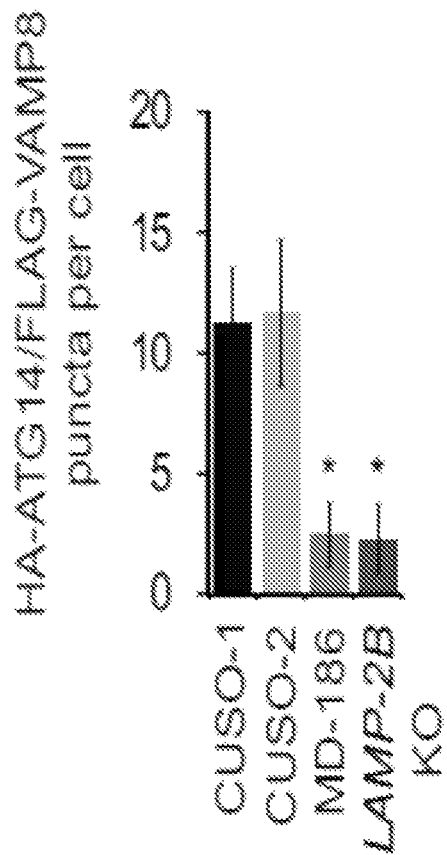

The cytosolic CCD of LAMP-2B may promote the formation of the ATG14-VAMP8 complex. In non-CMs, VAMP8 may be involved for autophagic fusion. STX17 may be a key player in fusion by interacting with SNAP-29 and VAMP8. ATG14 on autophagosomes may promote fusion by directly binding to the STX17-SNAP29 binary complex. Because LAMP-2B deficiency may lead to defects in autophagic fusion, LAMP-2B is believed to promote fusion by interacting with these proteins. Coimmunoprecipitation assays in HEK293 cells where basal and starvation induced autophagy has been well-characterized were used to test this theory. HA-ATG14 formed a complex with FLAG-STX17 and FLAG-SNAP29 (FIG. 3A, lanes 3-5), but not with FLAG-VAMP8 alone in HEK293 cells in which LAMP-2B is barely expressed (FIG. 3A, lane 2). HA-ATG14 was precipitated with VAMP8 when LAMP-2B was overexpressed, but overexpression of LAMP-2A did not lead to formation of the ATG14-VAMP8 complex (FIG. 3A, lanes 2, 7 and 12). Deletion of the C-terminal cytosolic CCD of LAMP-2B, composed of 11 amino acids (LAMP-2BACCD), completely abolished the interaction between ATG14 and VAMP8 (FIG. 3B). ATG14 and VAMP8 formed a complex in hiPSC-CMs, which natively express LAMP-2B (FIG. 3C, lane 7 and FIG. 3D, lane 11). The ATG14-VAMP8 complex was also disrupted in LAMP-2 KO hiPSCCMs and hiPSC-CMs derived from patients with Danon disease (FIG. 3C, lane 8 and FIG. 3D, lanes 12 and 13). Additionally, overexpression of LAMP-2B restored the ATG14-VAMP8 complex in LAMP-2 KO or Danon hiPSC-CMs (FIG. 3C, lane 9 and FIG. 3D, lanes 14 and 15). Also, colocalization of HA-ATG14 with FLAGVAMP8 was decreased in both LAMP-2B KO and Danon hiPSC-CMs (FIGS. 3 E and F). LAMP-2B may promote formation of the ATG14-VAMP8 complex.

Figure 14H:
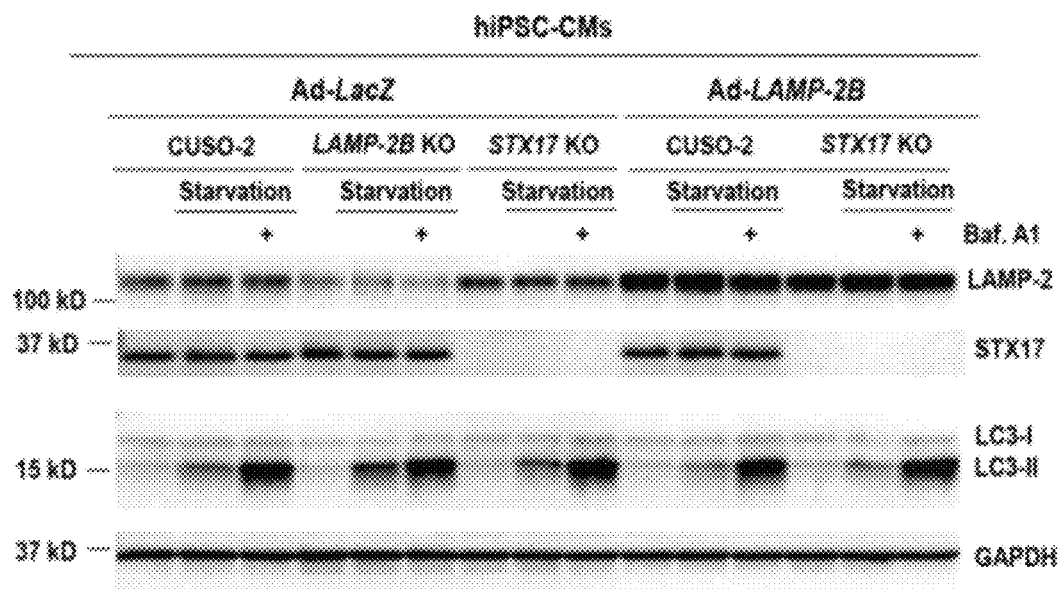
Figure 15A:
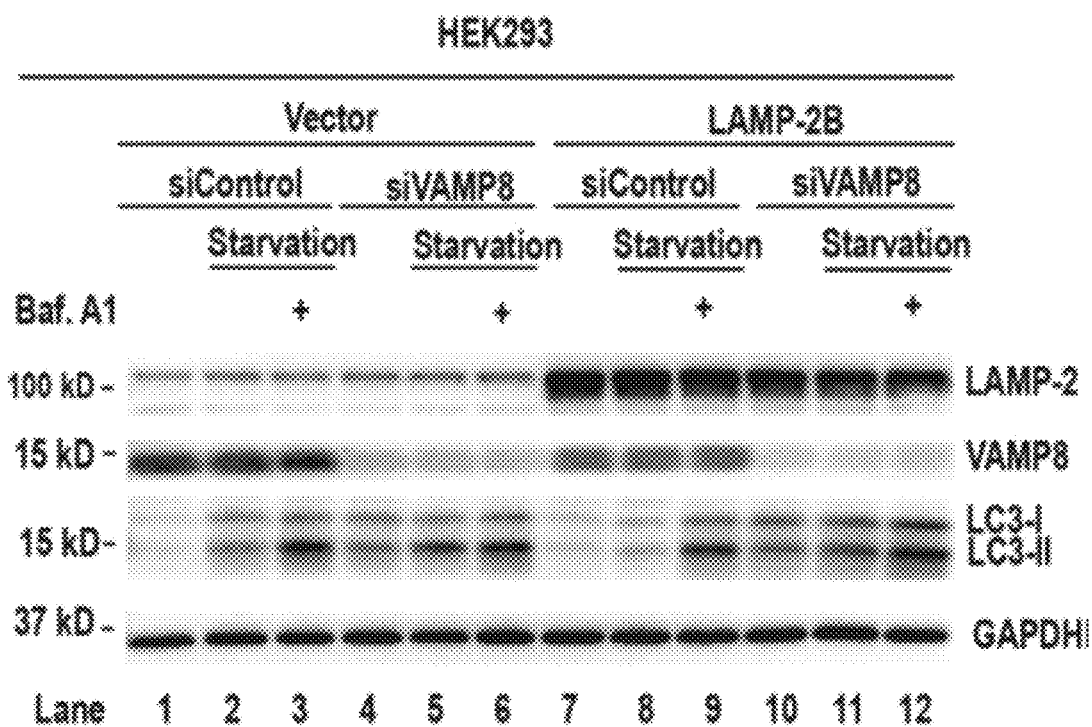
FIGS. 15A-F depict that VAMP8 and ATG14 are involved for LAMP-2B to promote fusion between autophagosomes and endosomes/lysosomes.
Figure 15B:
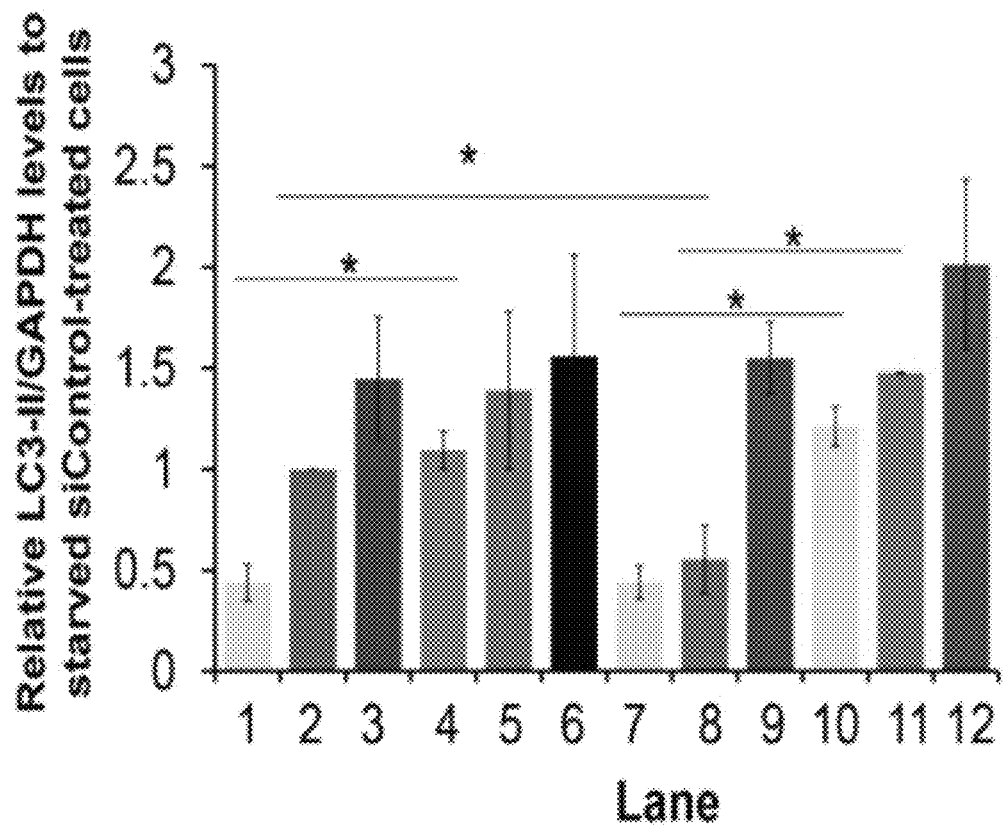
Figure 15C:
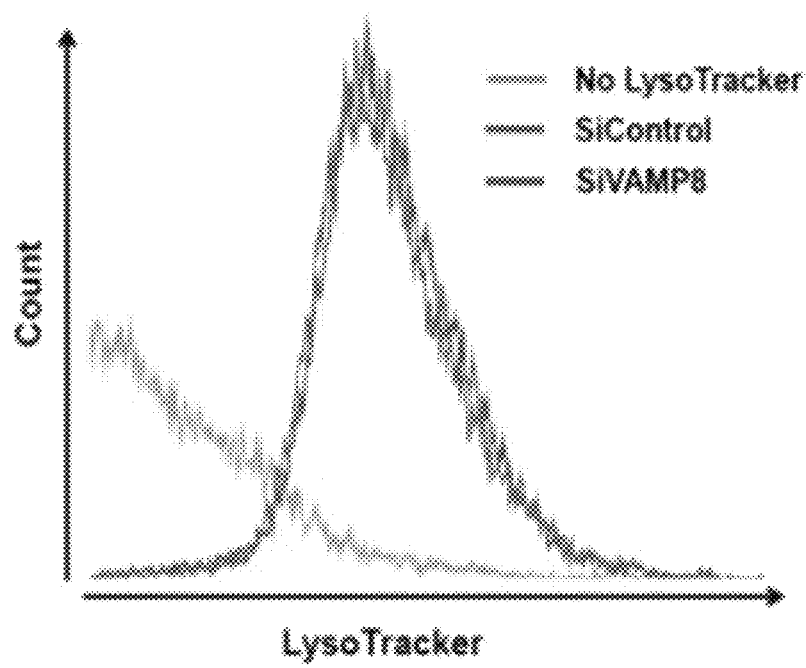
Figure 15D:
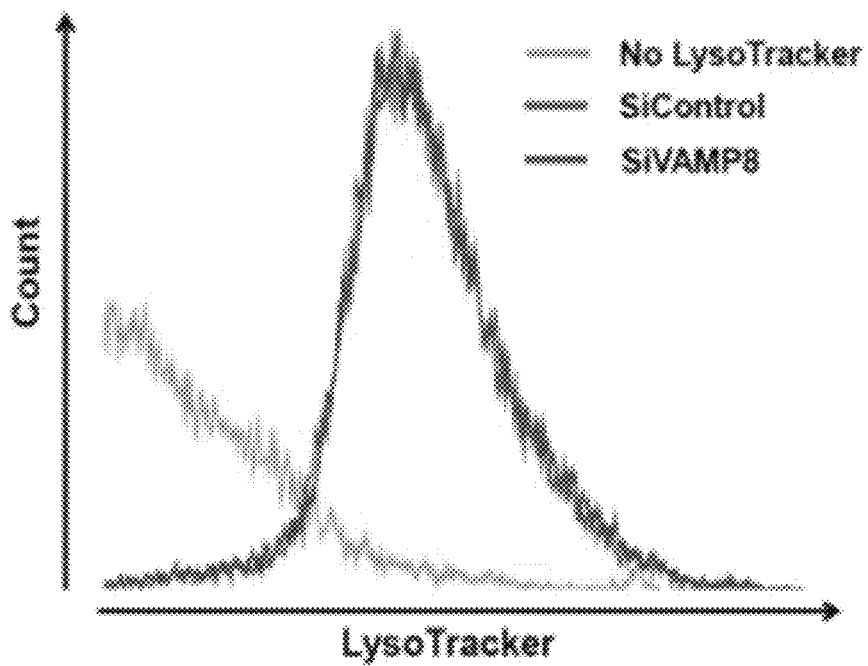
Figure 15E:
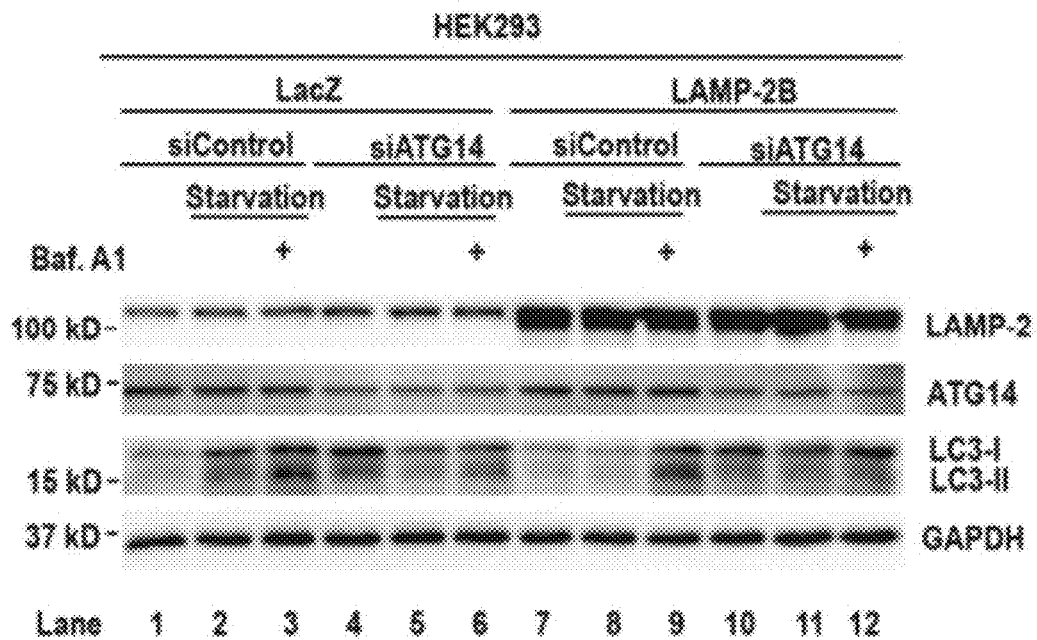
Figure 15F:
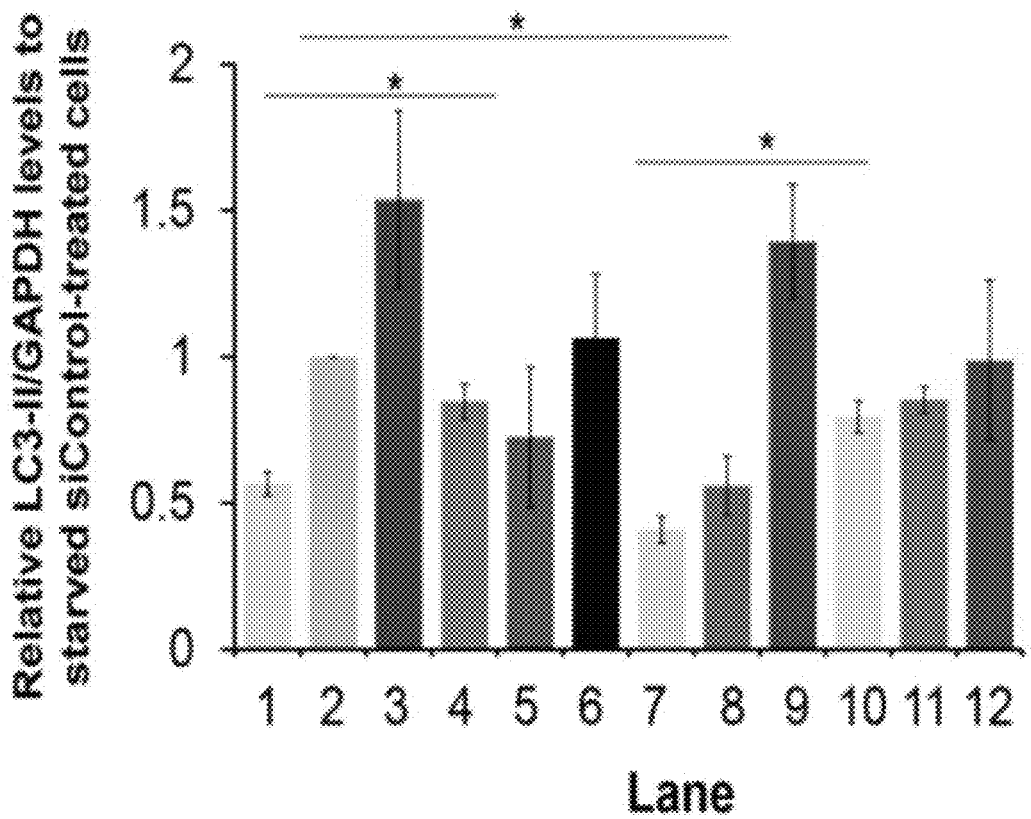

The CCD of LAMP-2B may be involved in promoting autophagosome-lysosome fusion in a STX17-independent manner. LAMP-2B may promote formation of the ATG14-VAMP8 complex. LAMP-2B is believed to promote autophagic fusion. In HEK293 cells, small interfering RNA (siRNA)-mediated knockdown of STX17 caused significant accumulation of LC3-II (FIG. 4 A-C, lanes 4 and 5 versus 1 and 2), confirming the essential role of STX17 in autophagic fusion. Expression of LAMP-2B, but not LAMP-2A, suppressed the accumulation of LC3-II caused by knockdown of STX17 (See, FIG. 4 A-C and FIG. 14A, lanes 4 and 5 versus 10 and 11). Expression of LAMP-2B led to similar LC3-II levels in control siRNA- and STX17 siRNA treated HEK293 cells (FIGS. 4 B and C, lanes 7 and 8 versus 10 and 11). Addition of bafilomycin A1 to block fusion led to similar LC3-II levels in both control siRNA- and STX17 siRNA-treated cells expressing either vector or LAMP-2B (FIGS. 4 B and C, lanes 3, 6, 9, and 12). LAMP-2B may promote autophagic fusion, rather than inhibiting the induction of autophagy. In contrast, expression of LAMP-2BACCD did not suppress the accumulation of LC3-II caused by STX17 knockdown (See, FIG. 4D and FIG. 14B, lanes 10 and 11 versus 4 and 5). CCD of LAMP-2B may be involved to decrease the accumulation of LC3-II caused by knockdown of STX17 in HEK293 cells.

To determine whether STX17 is essential for LAMP-2B to promote autophagic fusion in human cardiomyocytes, exon 4 of STX17 gene in hiPSCs (STX17 KO) was deleted using CRISPR/Cas9 technology. The excision of exon 4 resulted in a frame-shift mutation. Only the first 66 amino acids of STX17 are assumed to be produced, with no detectable expression (See, FIGS. 14 C-E). Surprisingly, neither knockdown or knockout of STX17 caused accumulation of LC3-II in hiPSC-CMs under either regular or starvation conditions (See, FIGS. 4 E and F and FIG. 14 F-H). The hiPSC-CMs, LAMP-2B deficiency caused a significant increase in LC3-II under starvation conditions (FIG. 4F), implying that LAMP-2B plays a more important role than STX17 in autophagic fusion in human cardiomyocytes. Overexpression of LAMP-2B reduced LC3-II levels similarly in both wild-type and STX17 KO hiPSC-CMs (FIGS. 4 E and F). STX17 may not be essential for autophagy in cardiomyocytes. LAMP-2B functions in autophagic fusion independently of STX17.

ATG14 and VAMP8 may be involved for LAMP-2B to promote autophagosome-lysosome fusion in human cardiomyocytes. The CCD of LAMP-2B may be involved not only to promote formation of the ATG14-VAMP8 complex, but also to complete the fusion step of autophagy. ATG14 and/or VAMP8 were tested to determine whether LAMP-2B promotes autophagic fusion. Knockdown of VAMP8 caused accumulation of LC3-II in HEK293 cells and hiPSC-CMs under regular and starvation conditions (See, FIGS. 5 A and B and FIGS. 15 A and B, lanes 4 and 5), confirming a role of VAMP8 in fusion. Overexpression of LAMP-2B decreased accumulation of LC3-II, especially under starvation conditions (See, FIGS. 5 A and B and FIGS. 15 A and B, lanes 2 and 8). However, knockdown of VAMP8 is believed to have totally abolished the ability of LAMP-2B to suppress accumulation of LC3-II (See, FIGS. 5 A and B and FIGS. 15 A and B, lanes 7 and 8 versus 10 and 11). Down-regulation of VAMP8 did not affect lysosomal biogenesis in hiPSC-CMs as assayed by flow cytometry analysis of LysoTracker intensity (See, FIGS. 15 C and D), consistent with previous findings that knockdown of VAMP8 did not affect lysosomal biogenesis and function. VAMP8 may be involved for LAMP-2B to promote autophagy-specific fusion in both non-cardiomyocytes and cardiomyocytes.

ATG14 may be involved not only in autophagic fusion by interacting with STX17-SNAP29 (7) but also in induction of autophagy. Knockdown of ATG14 in HEK293 or hiP-SCCMs increased LC3-II levels under regular conditions compared with cells treated with control siRNA (See, FIGS. 5C and 5D and FIGS. 15 E and 15F, lane 1 versus 4), suggesting that ATG14 is involved with in clearance of autophagosomes. However, knockdown of ATG14 also decreased LC3-II levels caused by bafilomycin A1 treatment under starvation conditions, suggesting that ATG14 also participated in induction of autophagy, especially under starvation conditions. Knockdown of ATG14 is believed to have completely abolished the effect of LAMP-2B overexpression on decreasing LC3-II levels (See, FIGS. 5 C and 5D and FIGS. 15 E and 15F, lanes 7 and 8 versus 10 and 11). ATG14 may be involved for LAMP-2B to promote autophagic fusion.

Example 5—LAMP-2 Mechanisms of Action

Figure 16A:
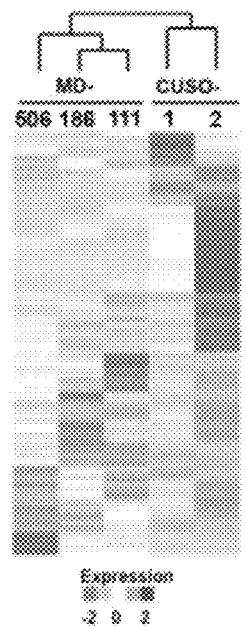
FIGS. 16A-H depict an accumulation of fragmented mitochondria in LAMP-2 deficient hiPSC-CMs.
Figure 16B:
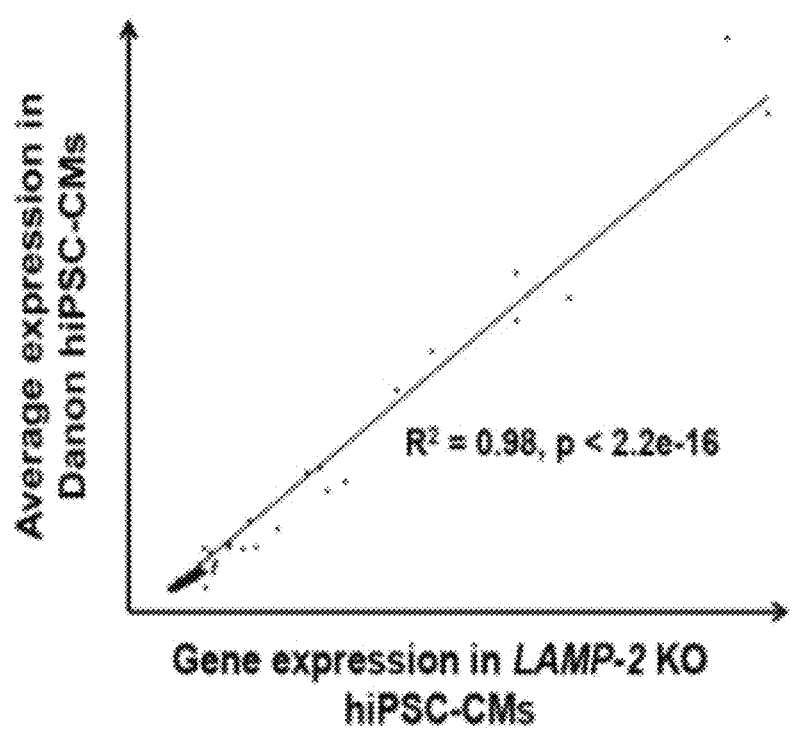
Figure 16C:
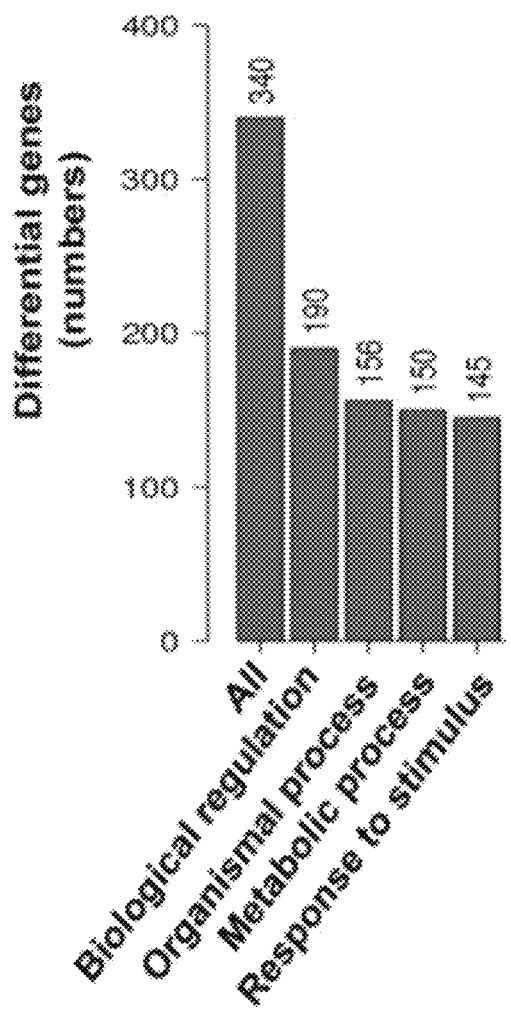
Figure 16D:
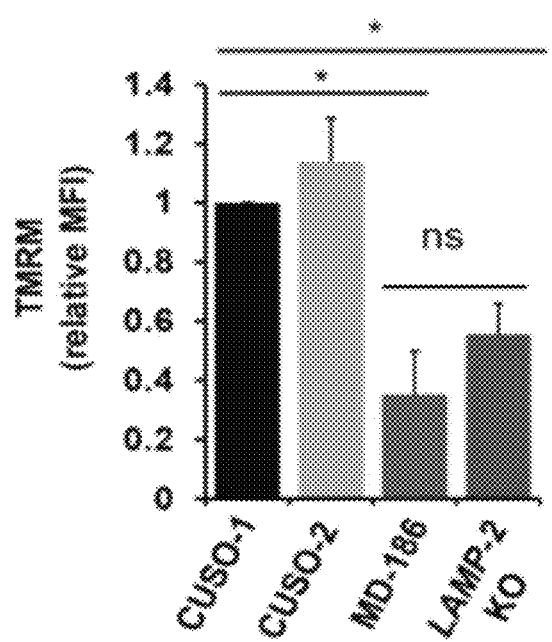
Figure 16E:
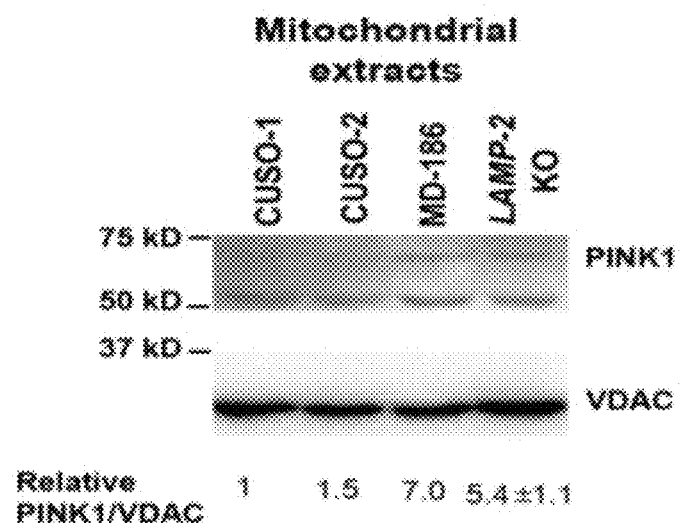

LAMP-2 mutation may be involved in causing the Danon Phenotype. The global gene expression in six hiPSC-CM lines were examined to understand mechanisms of action of LAMP-2. This RNA-seq analysis identified 420 differentially expressed genes, which demonstrated a greater than 1.5-fold change in expression between control and Danon hiPSC-CMs (See, FIG. 16A). Global gene expression in LAMP-2 KO hiPSC-CMs is believed to be similar to that in Danon hiPSC-CMs (See, FIG. 16B). Gene ontology analysis demonstrated that 150 differentially expressed genes with known functions were involved in metabolic processes (See, FIG. 16C), suggesting potential metabolic abnormalities in LAMP-2-deficient hiPSC-CMs. Mitochondria have a role in the regulation of cellular metabolism. In cardiomyocytes, autophagy is involved for mitochondrial homeostasis by removal of unhealthy mitochondria with decreased membrane potential. Removal of depolarized mitochondria by autophagy is initiated by accumulation of PTEN-induced putative kinase 1 (PINK1) on the outer membrane. As LAMP-2 KO and Danon hiPSC-CMs exhibit defects in autophagosome-lysosome fusion, it was believed that LAMP-2 deficiency could lead to mitochondrial and metabolic defects. Thus, mitochondrial membrane potential was tested using flow cytometry with tetramethylrhodamine methyl ester (TMRM). The mitochondrial membrane potential of Danon and LAMP-2 KO hiPSCCMs was lower than that of control hiPSC-CMs (See, FIG. 16D), indicating mitochondrial depolarization. Immunoblotting analysis revealed that PINK1 was accumulated in the mitochondria of Danon and LAMP-2 KO hiPSC-CMs (See, FIG. 16E). Electron microscopy analysis showed that some autophagosomes contained mitochondria (See, FIG. 9C), which is believed to suggest dysregulation of both general and mitochondrial autophagy in Danon hiPSC-CMs. Removal of depolarized mitochondria by autophagy may have been impaired in LAMP-2-deficient hiPSC-CMs.

Figure 16F:
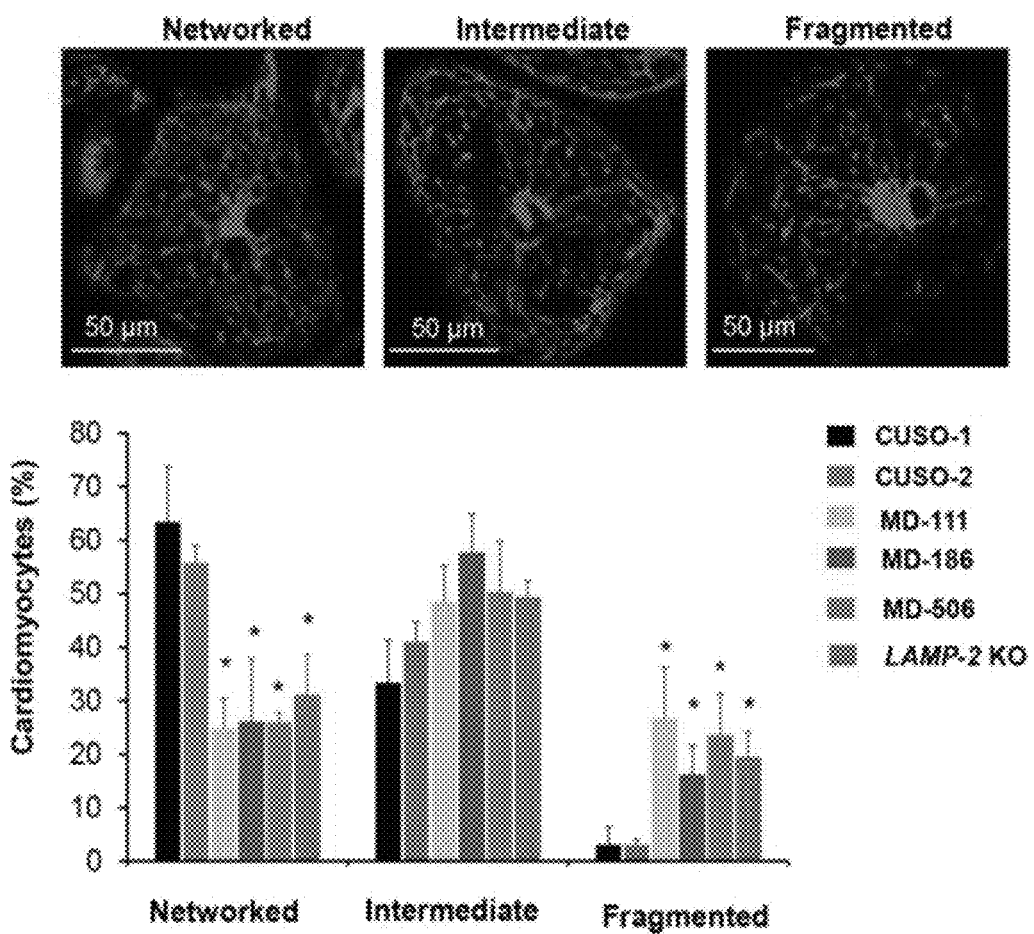
Figure 16G:
Figure 16H:
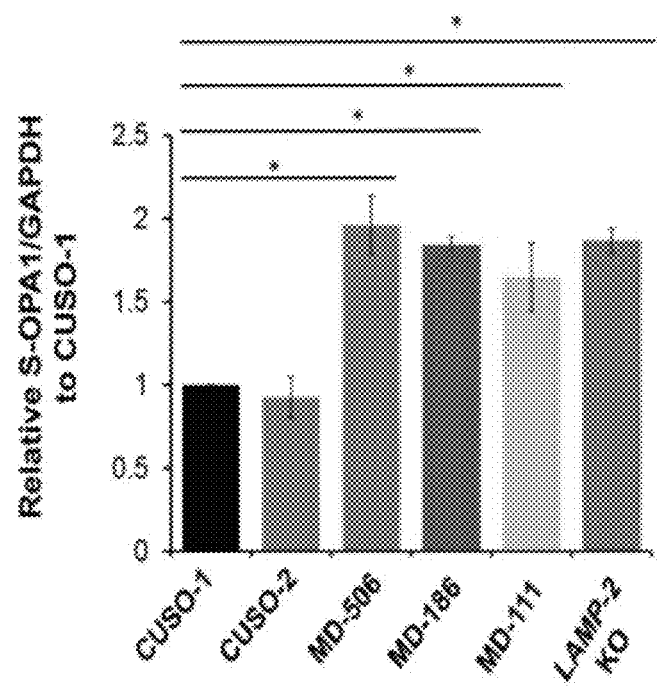
Figure 17A:
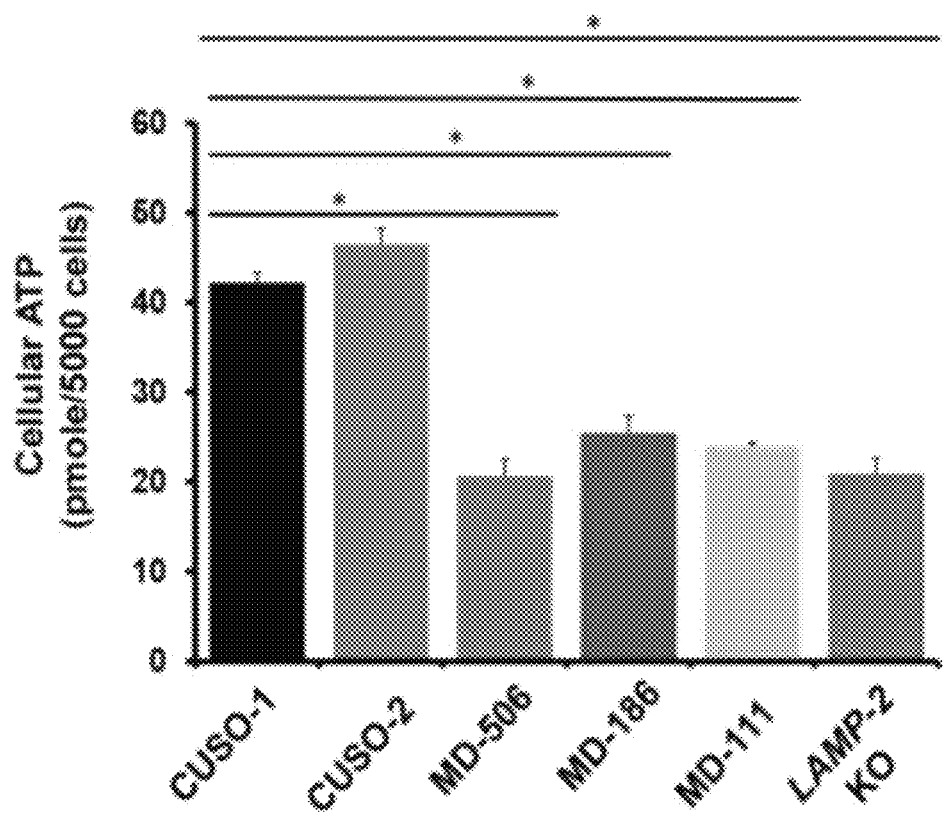
FIGS. 17A-C depict a LAMP-2 deficiency is sufficient to cause mitochondrial dysfunction in hiPSC-CMs.
Figure 17B:
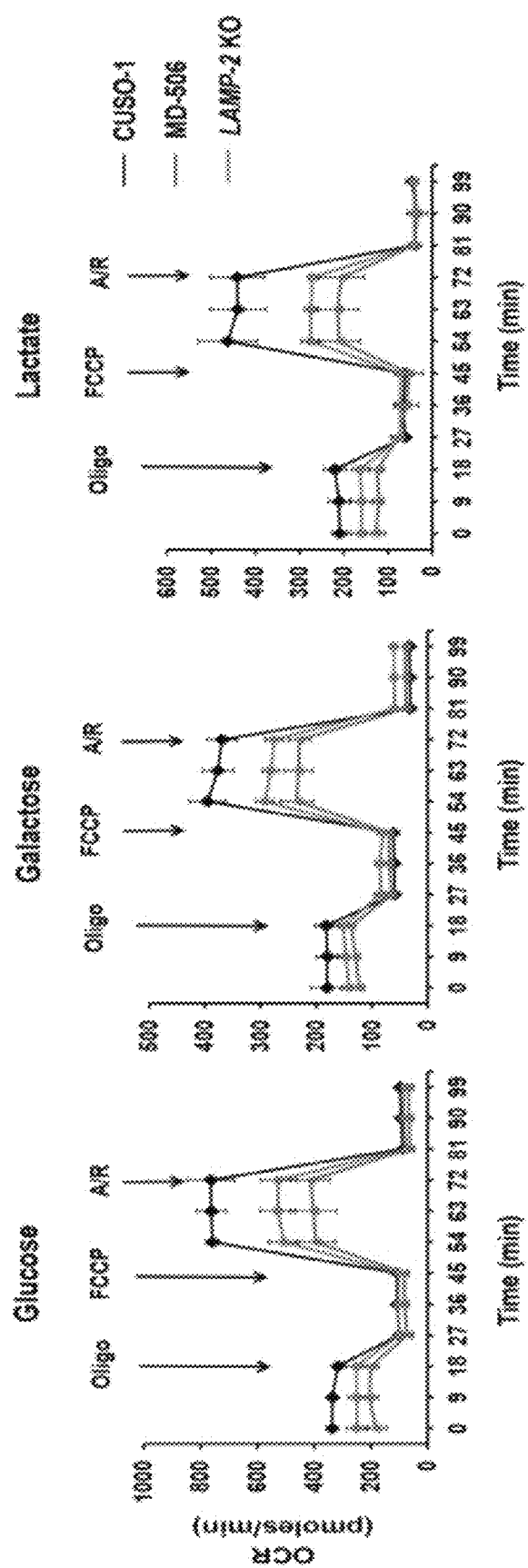

Mitochondrial morphology and function were assessed in control, Danon, and LAMP-2 KO hiPSC-CMs. Mitochondrial fragmentation was believed to be more evident in LAMP-2-deficient hiPSCCMs than control (See, FIG. 16F). Accumulation of the short isoform of optic atrophy 1 (S-OPA1) was associated with mitochondrial fission and fragmentation. Levels of SOPA1 were increased in LAMP-2-deficient hiPSC-CMs (See, FIGS. 16 G and 16H). LAMP-2-deficient hiPSC-CMs also produced lower levels of ATP than control hiPSC-CMs (See, FIG. 17A). Next, we analyzed mitochondrial function by measuring the oxygen consumption rate (OCR) of hiPSC-CMs cultured in one of three different energy sources: glucose, galactose, and lactate. OCR of basal respiration, ATP production, and maximal respiratory capacity (MRC) were decreased in Danon hiPSC-CMs cultured with each of these three energy sources (See, FIGS. 17B and 17C). LAMP-2 deficiency may impair mitochondrial function in cardiomyocytes.

Figure 6A:
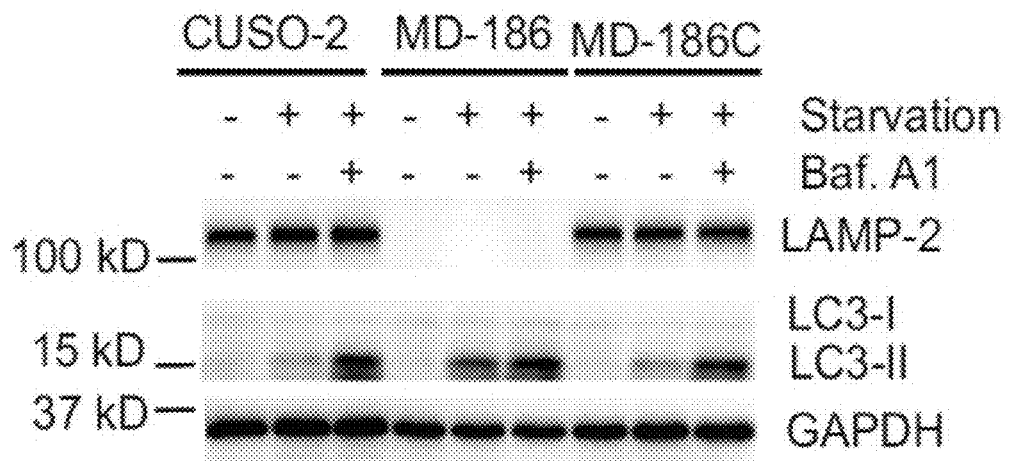
FIGS. 6A-F depict a correction of the LAMP-2 mutation rescues functional abnormalities in human cardiomyocytes.
Figure 6B:
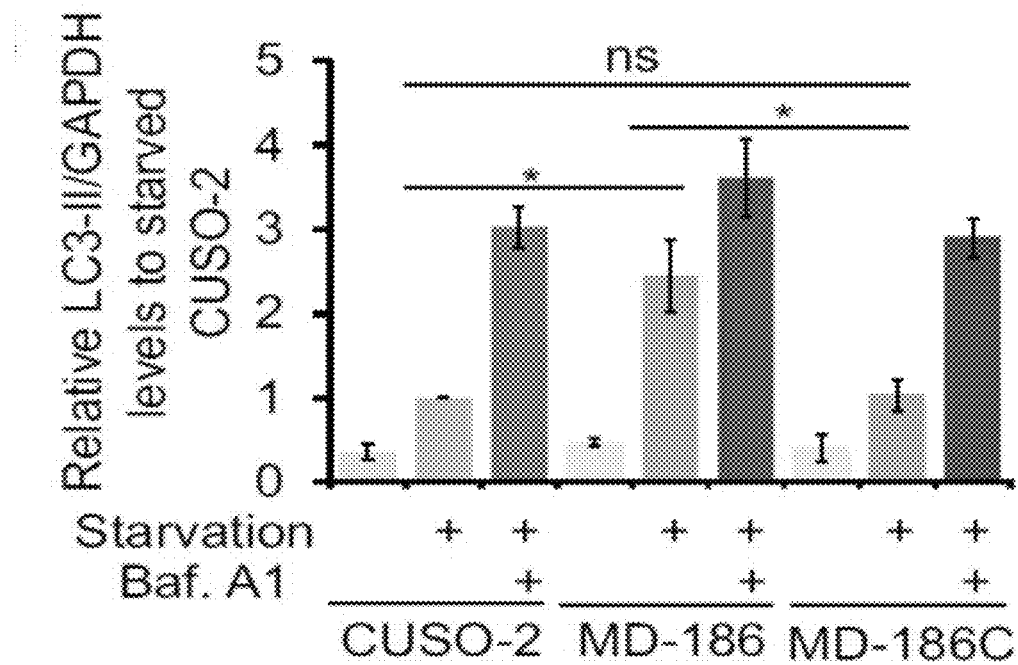
Figure 6C:
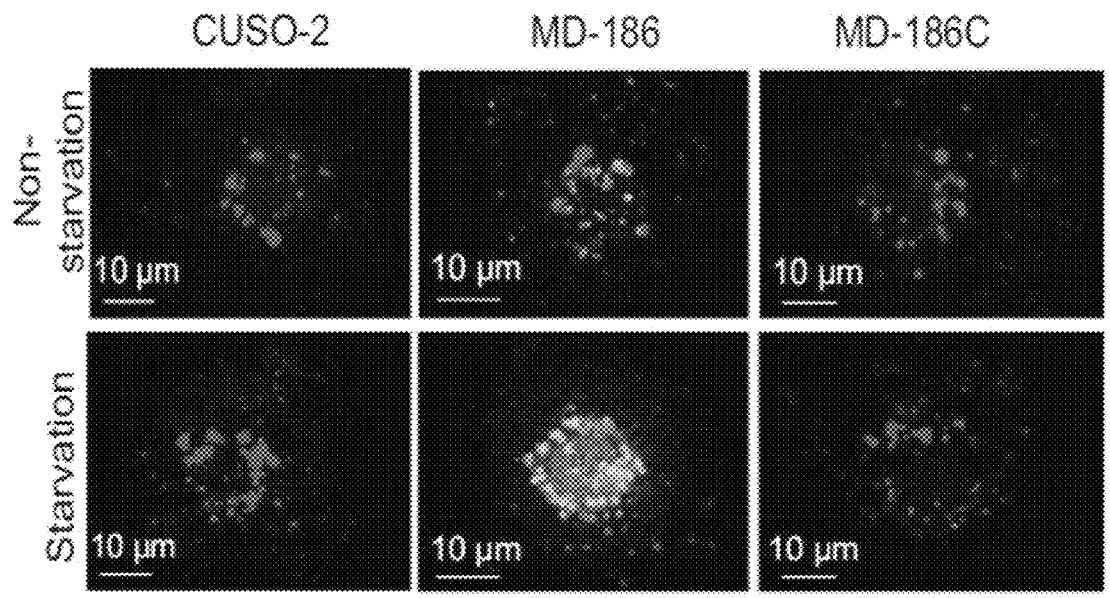
Figure 6D:
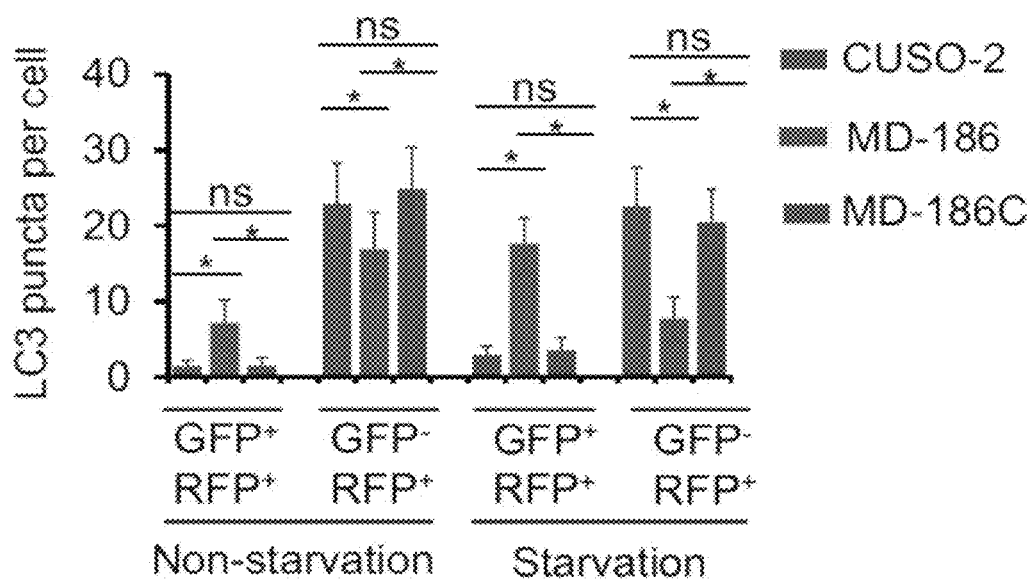
Figure 6E:
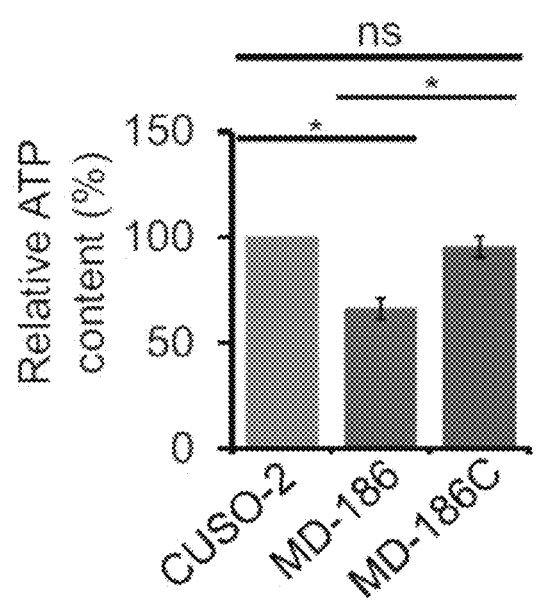
Figure 6F:
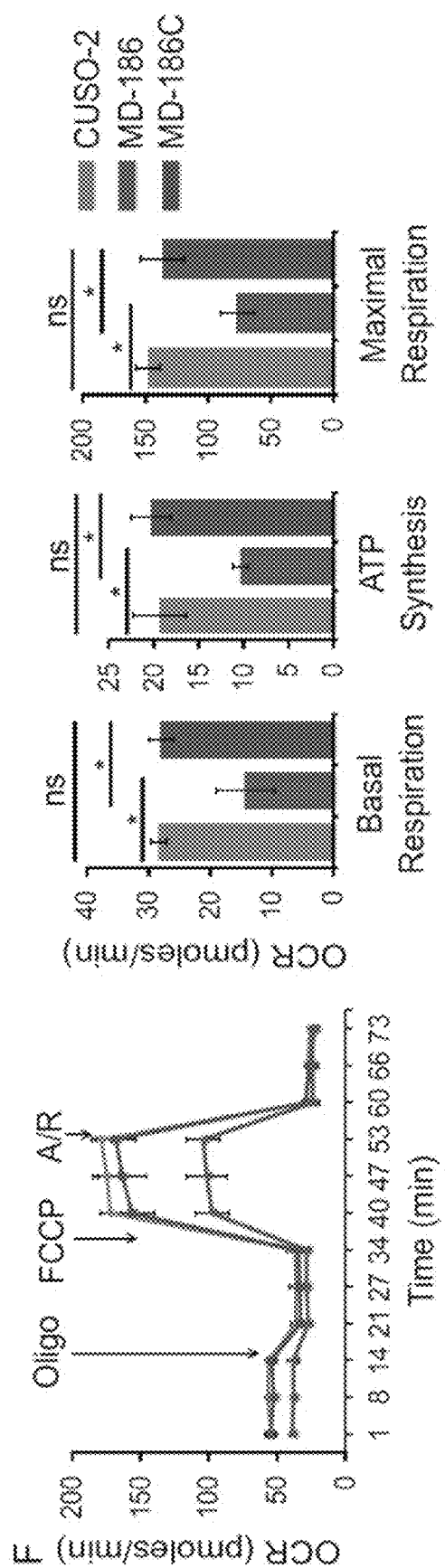
Figure 17C:
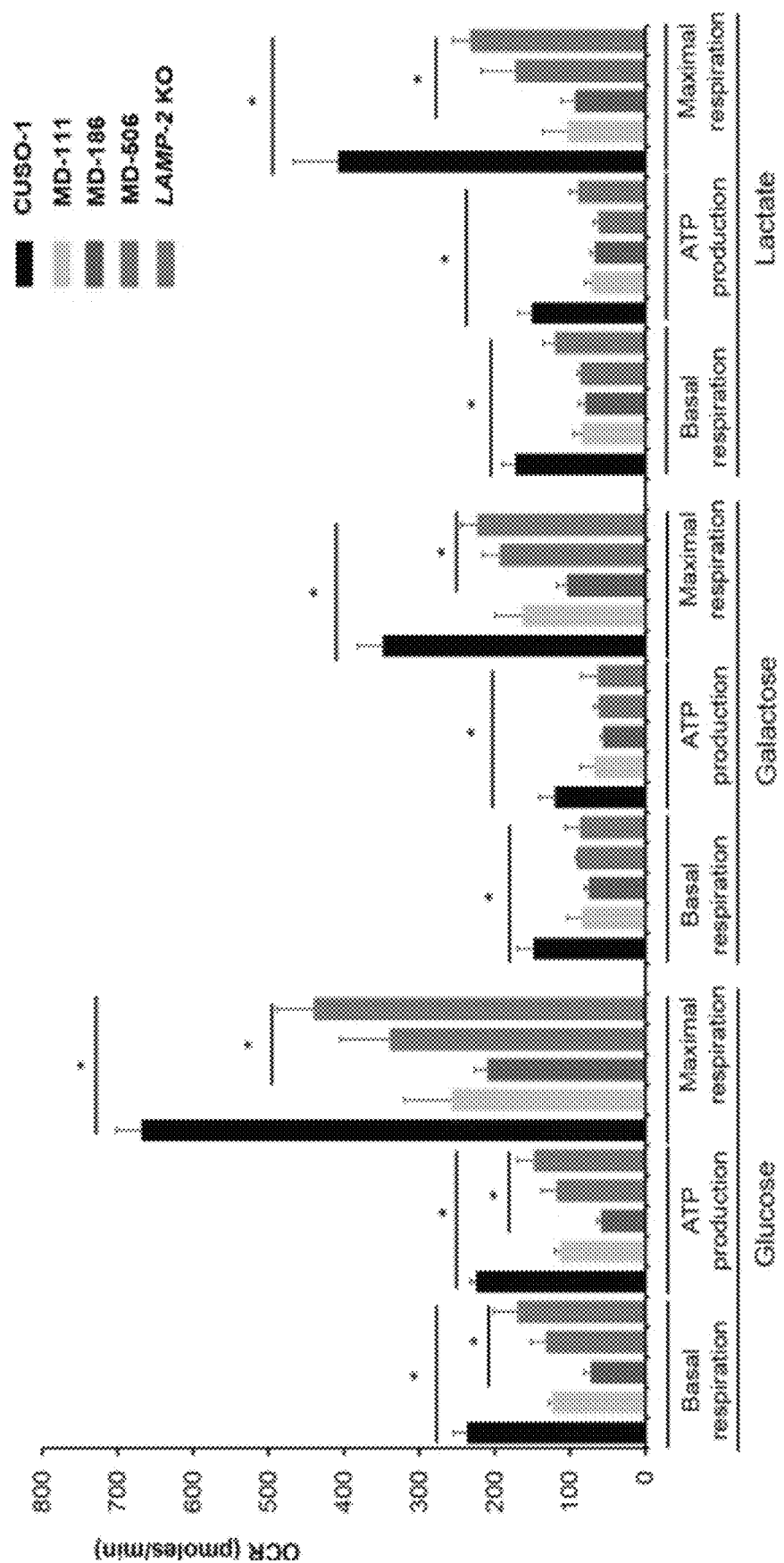

While LAMP-2-deficient hiPSC-CMs uniformly exhibited mitochondrial abnormalities, certain phenotypes observed in hiPSCCMs varied from patient to patient (See, FIG. 17C). This data is believed to be consistent with the clinical observation that Danon patients display variations in disease onset and severity. An individual patient's genetic background may contribute to the variations in clinical features. Patient-derived hiPSCs could potentially have numerous other genetic differences besides LAMP-2 mutations, which might also contribute to progression of Danon cardiomyopathy. To determine whether the LAMP-2 mutation causes Danon cardiomyopathy, the LAMP-2 mutation was corrected in MD-186 hiPSCs using a CRISPR-based approach. A single guide RNA was designed to target exon 3 near the mutation site (c.247C>T). The T base responsible for the point mutation was replaced with C through homology-directed repair between the mutated gene segment and a 100-mer single-strand DNA oligonucleotides containing normal LAMP-2 sequence (See, FIG. 18A). Corrected hiPSC (hereinafter referred to as MD-186C) clones were confirmed by sequencing and immunoblotting for LAMP-2 protein (See, FIGS. 18B and 18C). Immunoblotting is believed to have revealed similar LC3-II levels in mutation-corrected MD-186C hiPSC-CMs, compared with control (FIGS. 6 A and B). Autophagic flux assays by the mRFP-EGFP-LC3 construct are believed to have shown that correction of the LAMP-2 mutation restored autophagosome-lysosome fusion (FIGS. 6 C and D). Additionally, while Danon hiPSC-CMs produced lower levels of ATP than control hiPSCCMs, correction of the LAMP-2 mutation increased ATP content, reaching a similar level to control (FIG. 6E). OCR of basal respiration, ATP production, and MRC were increased in MD-186C hiPSC-CMs to levels comparable to control (FIG. 6F). This data is believed to indicate that correction of the LAMP-2 mutation (c.247C>T) is sufficient to completely rescue Danon phenotype. LAMP-2 deficiency may be involved in causing Danon cardiomyopathy.

Example 6—Role of LAMP-2B

Figure 7A:
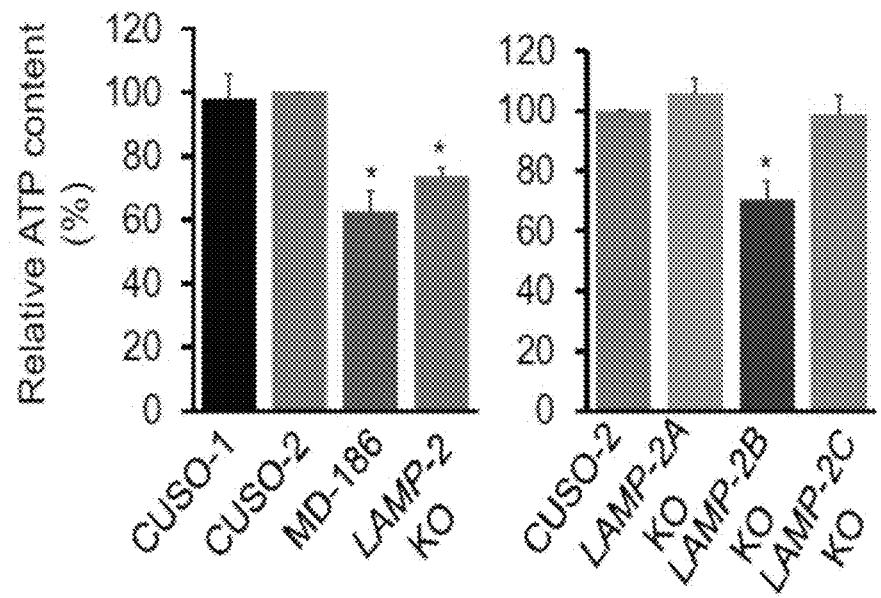
FIGS. 7A-7G depict that LAMP-2B deficiency causes mitochondrial and contractile abnormalities in human cardiomyocytes.
Figure 7B:
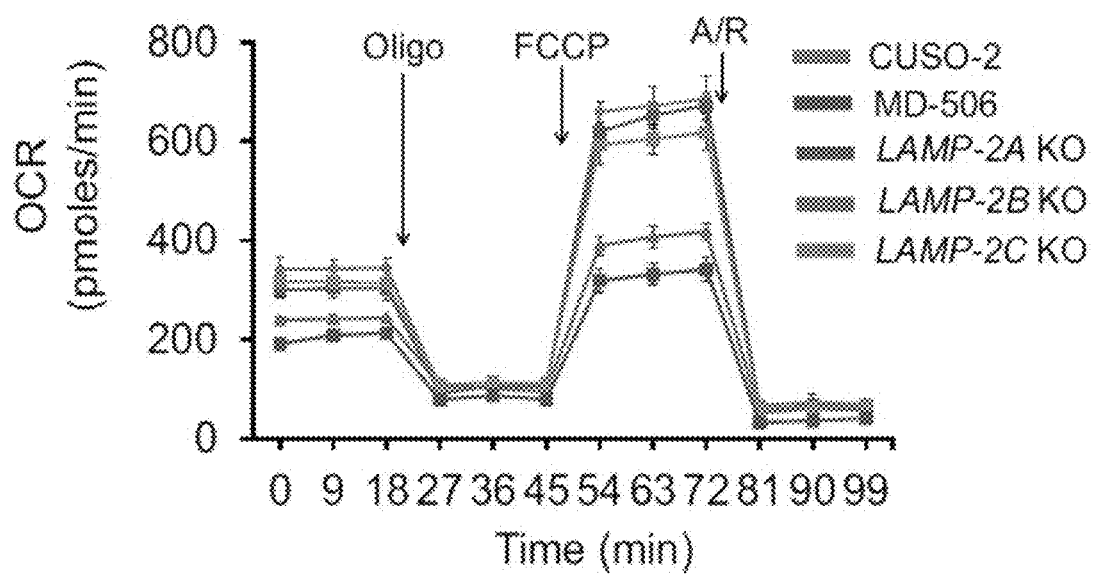
Figure 7C:
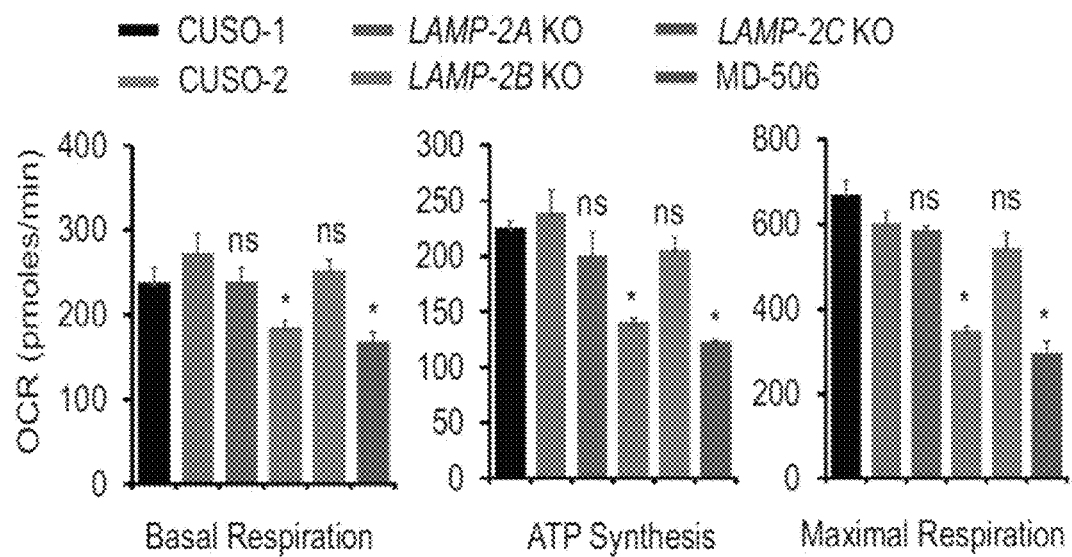

LAMP-2B deficiency in human cardiomyocytes is believed to cause mitochondrial and contractile abnormalities. To examine whether LAMP-2B is responsible for the mitochondrial defects of Danon disease, mitochondrial morphology and function was assessed in LAMP-2B KO hiPSC-CMs. LAMP-2B KO, LAMP-2 KO, or Danon hiPSC-CMs, which produced lower levels of ATP than control hiPSCCMs. However, knockout of LAMP-2A or LAMP-2C did not decrease ATP production (FIG. 7A). OCR of basal respiration, ATP production, and MRC were decreased in LAMP-2B KO hiPSC-CMs, reaching a similar level to Danon hiPSC-CMs. However, deletion of LAMP-2A or LAMP-2C in hiPSC-CMs was not believed to cause mitochondrial dysfunction (FIGS. 7 B and C). LAMP-2B may be specifically responsible for metabolic defects in Danon hiPSC-CMs.

Figure 7D:
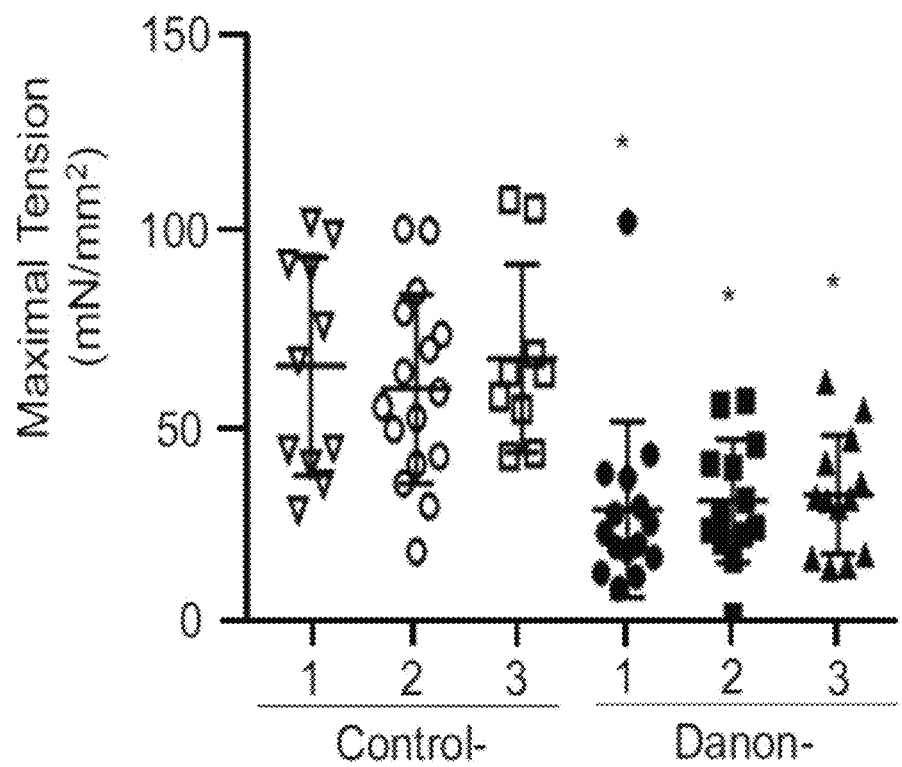
Figure 7E:
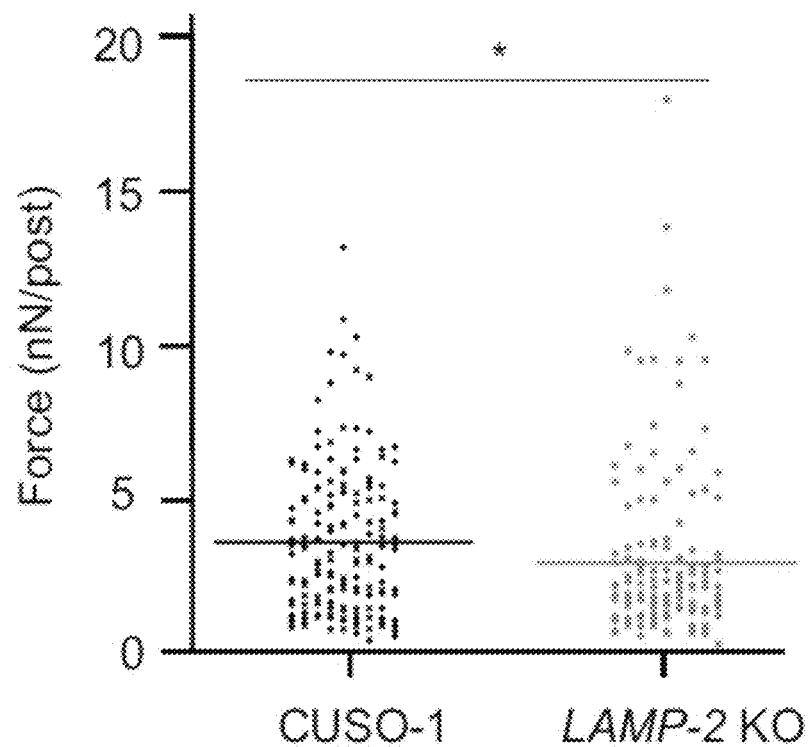
Figure 7F:
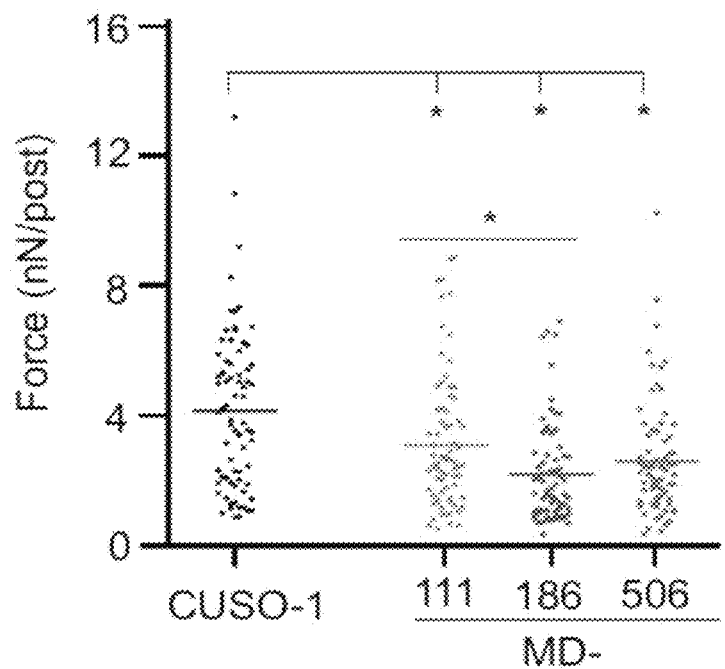
Figure 7G:
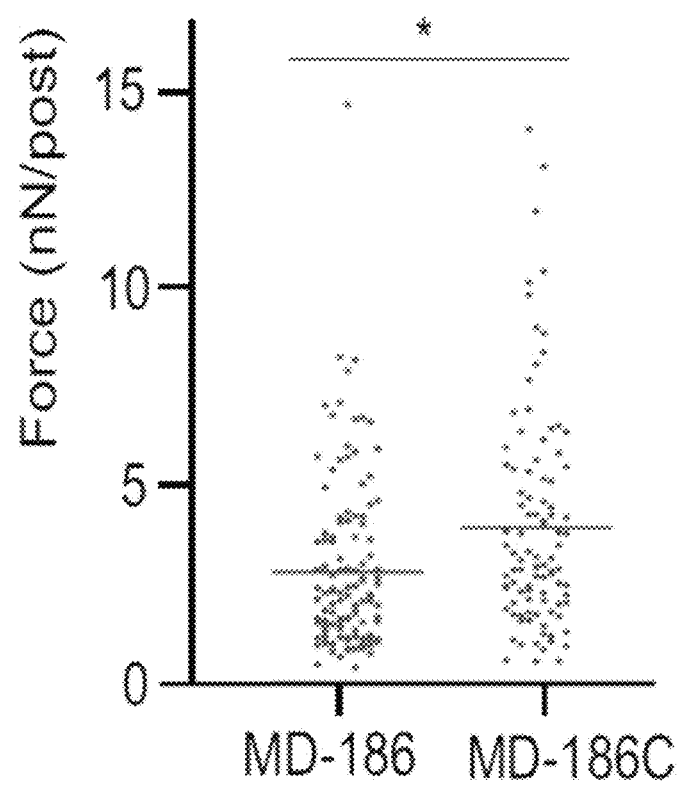
Figure 19A:
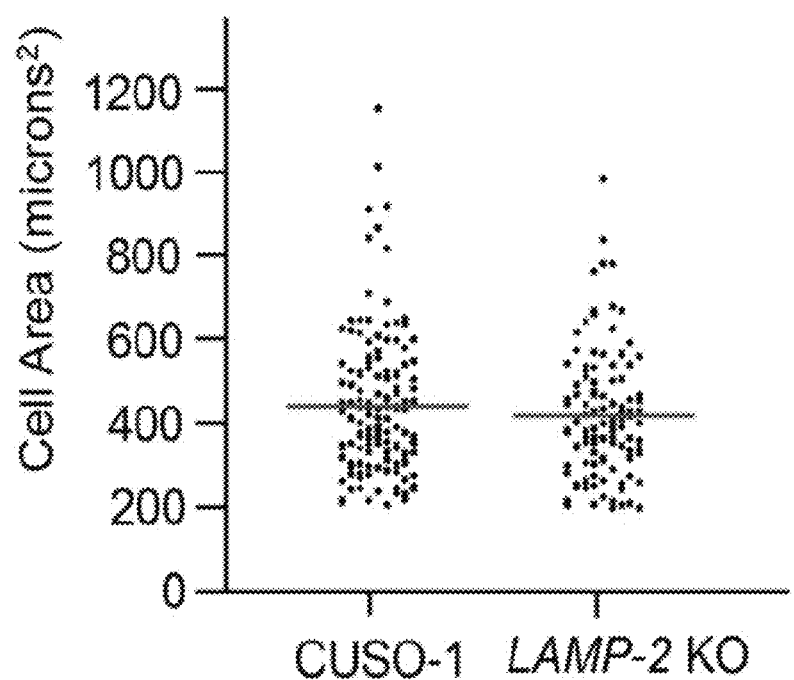
FIGS. 19A-B depict adhesion of hiPSC-CMs to microposts. Micropost-based contractile assays were performed under a blinded condition. More than 3 independent experiments (with ~25 cells each) were performed for each hiPSC-CM lines on day 60. The spread area of individual hiPSC-CMs on microposts were measured, which is shown in FIG. 19A for CUSO-1 and LAMP-2 KO hiPSC-CMs, in FIG. 19B for CUSO-1 and three Danon hiPSC-CM lines. Each data point represents an individual cell. Lines represent average force per post for each group. Statistical analysis was performed using a 1-way ANOVA with a Bonferroni posthoc test. P-values or statistically significant differences are specified, otherwise pairwise statistics are not significant.
Figure 19B:
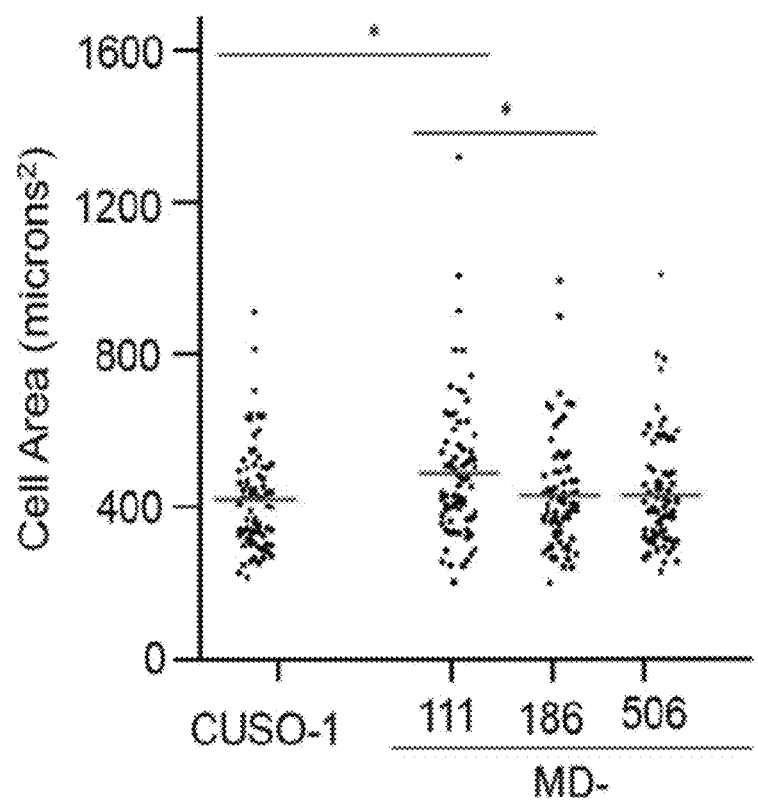

Having established the importance of the LAMP-2B isoform for Danon disease, it was investigated whether whole-heart phenotypes of Danon disease could be recapitulated using hiPSC-CMs. Danon patients develop cardiomyopathy, which is often accompanied by impaired contractile function. Myofibrils isolated from hearts of patients with Danon disease generated reduced maximal tension compared with myofibrils from control hearts (FIG. 7D). Therefore, whether LAMP-2 KO or Danon hiPSC-CMs could recapitulate the contractile abnormalities of Danon hearts was examined. To characterize contractile force produced by single hiPSC-CMs, a platform of micropost arrays was used. LAMP-2 KO or Danon hiPSC-CMs generated less contractile force per post than control hiPSC-CMs (See, FIGS. 7E and 7F and FIGS. 19A and 19B). Genetic correction of the LAMP-2 mutation (c.247C>T), which restored the LAMP-2 expression (See, FIGS. 18B and 19C), increased contractile force generation of hiPSC-CMs (FIG. 7G). LAMP-2B, accounting for >70% of LAMP-2 protein in cardiomyocytes, may be involved in cardiomyocytes as well as whole heart function.

Figure 20:
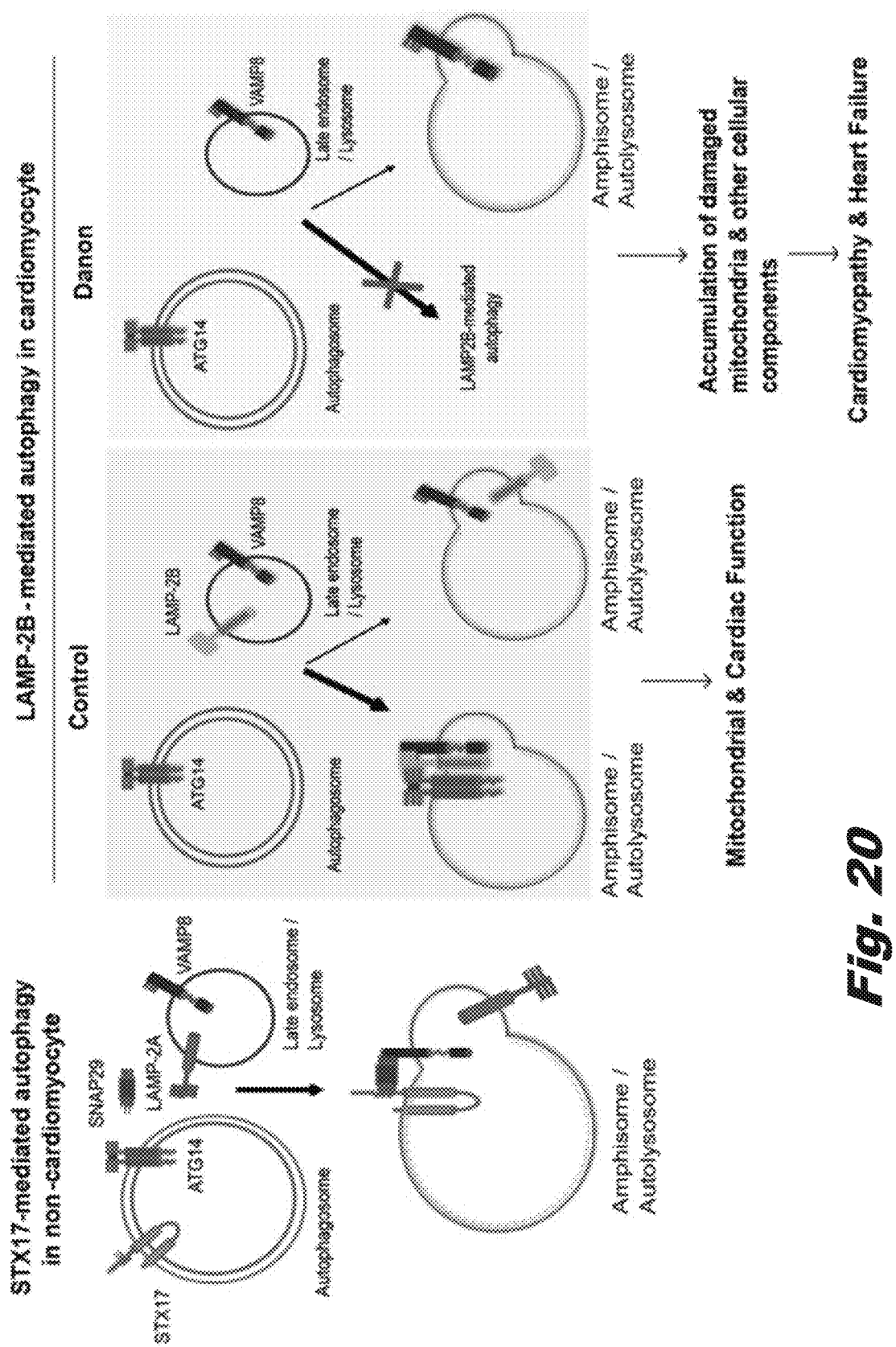
FIG. 20 depicts a LAMP-2B-mediated fusion between autophagosomes and late endosomes/lysosomes in human cardiomyocytes. In non-CMs in which LAMP-2A is the major isoform of LAMP-2, STX17 is involved in autophagic fusion by interacting with SNAP29 and VAMP8. ATG14 promotes STX17-mediated fusion. In cardiomyocytes where LAMP-2B is predominantly expressed, LAMP-2B promotes autophagic fusion by interacting with VAMP8 and ATG14 via its cytosolic CCD, in a STX17-independent manner. STX17 may not be essential for autophagy in cardiomyocytes. Mutations in the LAMP-2 gene cause LAMP-2B deficiency in patients with Danon disease. The LAMP-2B deficiency impairs autophagic fusion, leading to accumulation of damaged cellular components that causes cardiomyopathy and heart failure in patients with Danon disease.

Previously undefined biological and molecular roles for LAMP-2B were identified in the control of fusion between autophagosomes and endosomes/lysosomes via an interaction among ATG14, VAMP8, and LAMP-2B. LAMP-2B deficiency is believed to have caused defects in autophagy in hiPSC-CMs by disrupting this STX17-independent autophagosome-lysosome fusion in human cardiomyocytes, leading to Danon cardiomyopathy (See, FIG. 20). Gene correction of the LAMP-2 mutation rescued the Danon phenotype (See, FIGS. 6 and 7G), and may be a potential therapy for this disease.

Autophagic turnover occurs at a faster rate in cardiomyocytes than in non-cardiomyocytes (See, FIG. 12A) suggesting a role for autophagy in cardiac homeostasis. A distinct autophagic pathway in cardiomyocytes mediated was identified by LAMP-2B (See, FIG. 20). In non-CMs where LAMP-2A is predominant, STX17 mediates fusion by interacting with SNAP29 and VAMP8. In these cells, knockdown of STX17 caused accumulation of LC3-II. In cardiomyocytes, knockout of STX17 failed to do so (FIGS. 4 E and F), suggesting a unique mechanism in cardiomyocytes that is distinct from that mediated by STX17. These studies are believed to demonstrate that LAMP-2B mediates STX17-independent autophagic fusion by interacting with ATG14 and VAMP8 through its C-terminal CCD. However, LAMP-2B may promote autophagic fusion by interacting with other molecules. Knockout of LAMP-2B did not completely block fusion between autophagosomes and lysosomes (FIGS. 2 D and E), indicating that LAMP-2B-independent pathways are also involved in this process in cardiomyocytes. Deficiency of LAMP-2B rather than LAMP-2A or LAMP-2C is believed to cause metabolic and autophagic abnormalities in human cardiomyocytes. Although most Danon patients carry mutations that result in deficiency of all three LAMP-2 isoforms, some Danon patients carry mutations that only lead to LAMP-2B deficiency, supporting the notion that LAMP-2B deficiency is involved in Danon pathologenesis.

LAMP-2B interacts with ATG14 and VAMP8 through its CCD tail. The CCD of ATG14 interacts with the helix motif of STX17. This interaction may stabilize the STX17-SNAP29 complex, which is involved in fusion activity by further interacting with the helix domain of VAMP8. Both ATG14 and VAMP8 are believed to be involved for LAMP-2B to promote autophagy-specific fusion in cardiomyocytes. However, it is also likely that LAMP-2B regulates cardiac autophagy by interacting with other molecules besides ATG14 and VAMP8. In addition, the mechanism by which LAMP-2B is recruited to interact with VAMP8 and ATG4 is not known.

Example 7—LAMP-2A Mechanisms

Figure 2A:
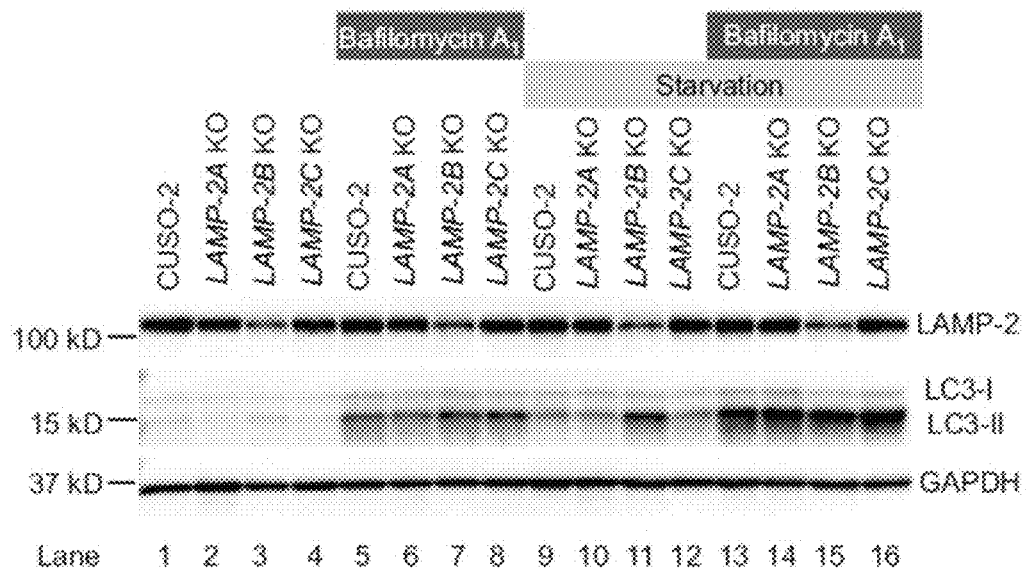
FIGS. 2A-G depicts that LAMP-2B deficiency is sufficient to cause defects in autophagosome-lysosome fusion.
Figure 2B:
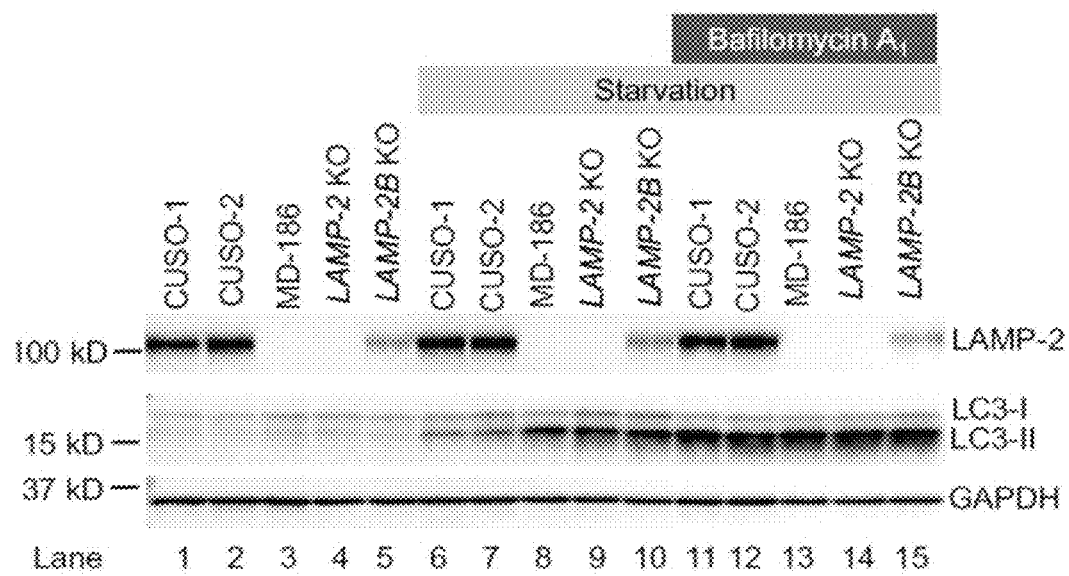
Figure 2C:
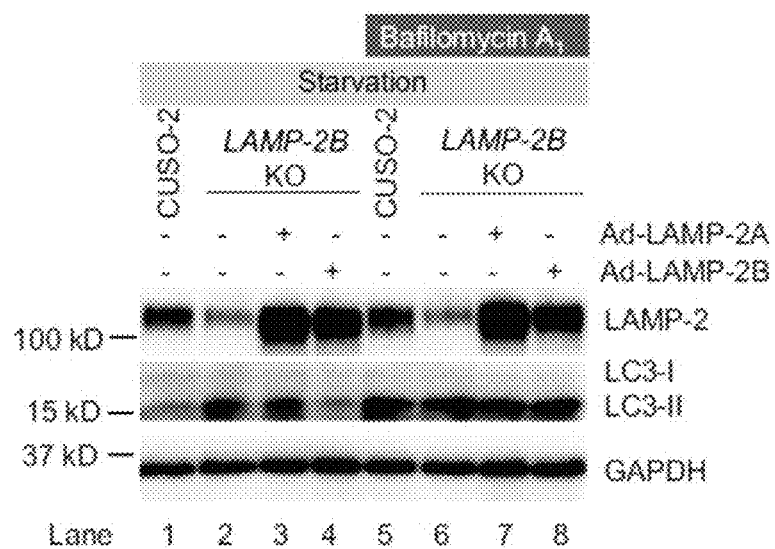
Figure 2D:
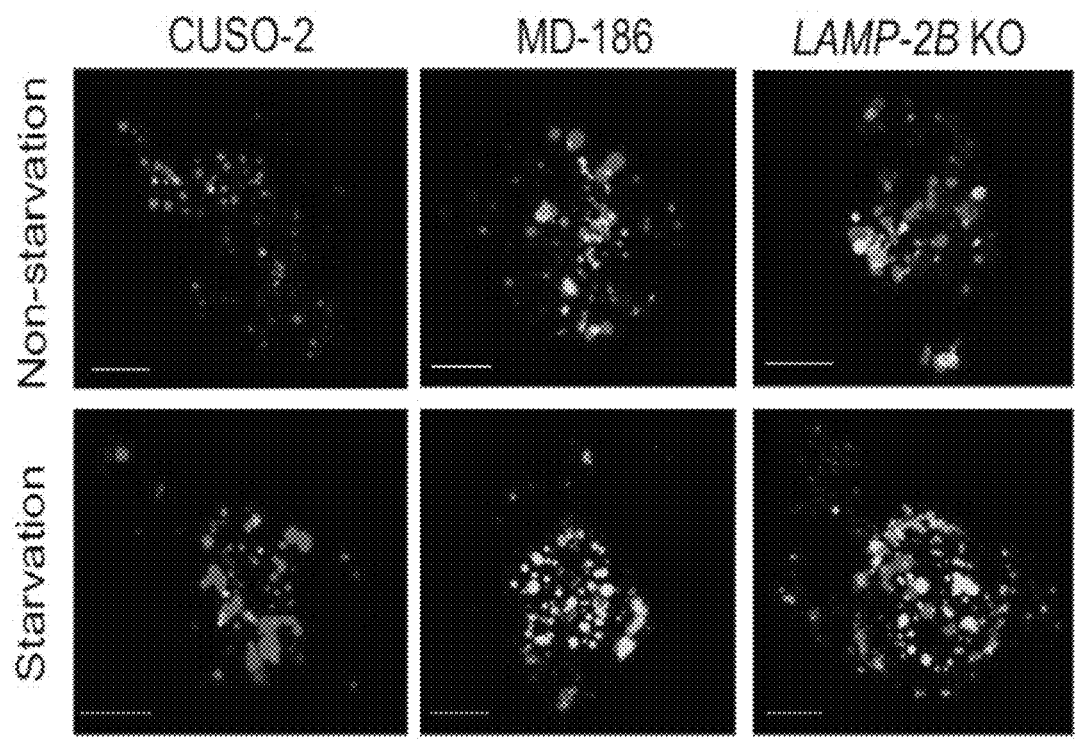
Figure 2E:
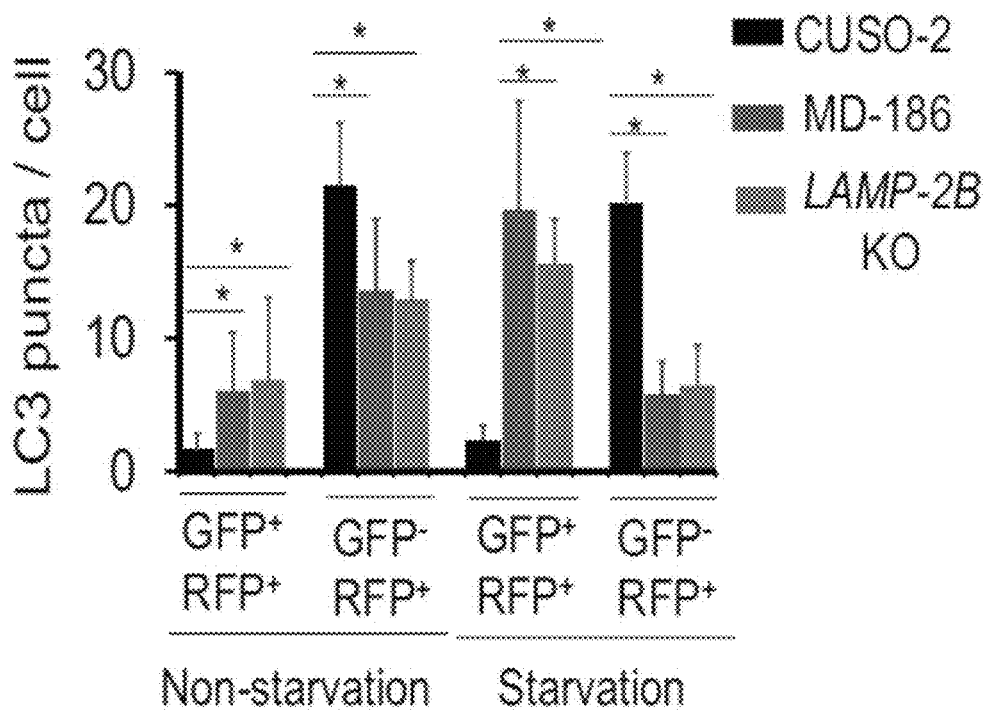
Figure 2F:
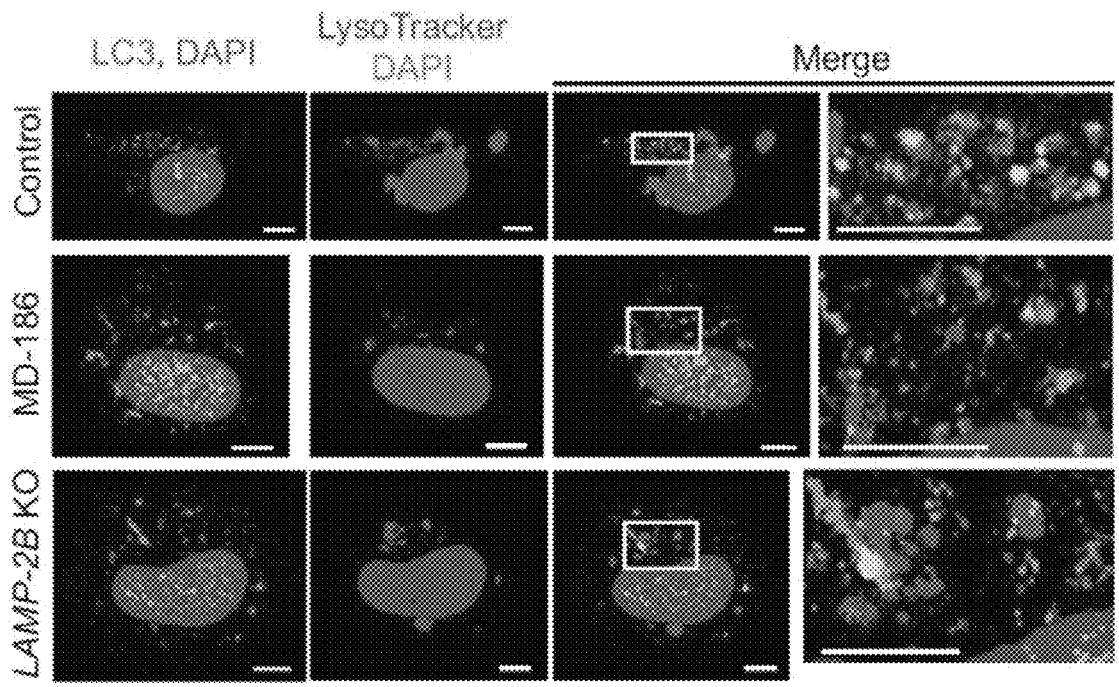
Figure 2G:
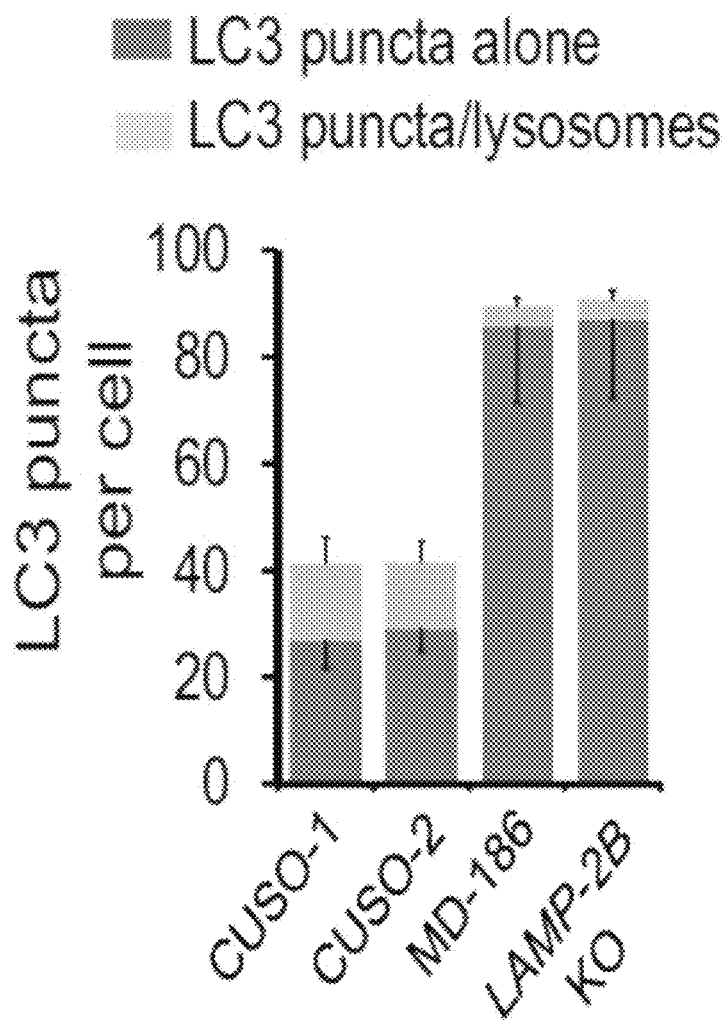
Figure 4A:
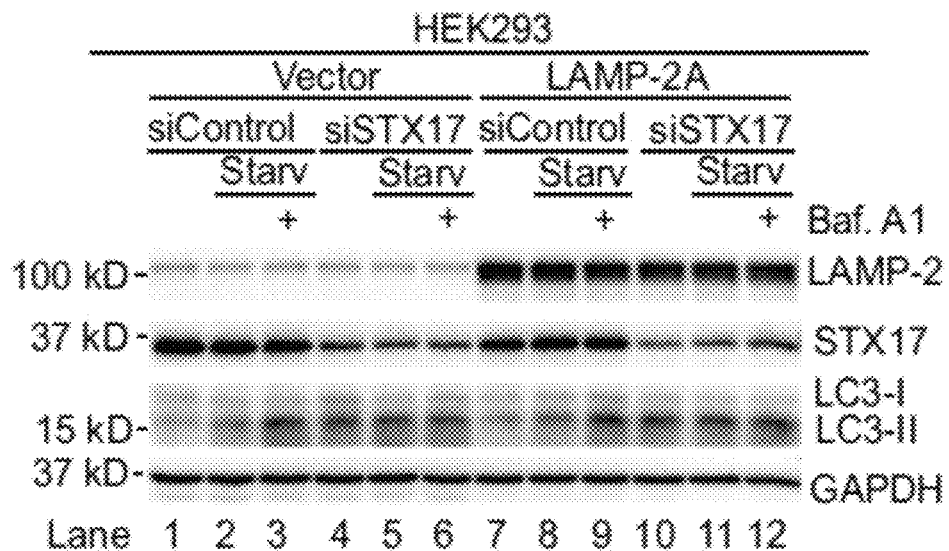
FIGS. 4A-F depict that the CCD is involved for LAMP-2B to promote autophagosome-lysosome fusion, independently of STX17. Starv, starvation.
Figure 4B:
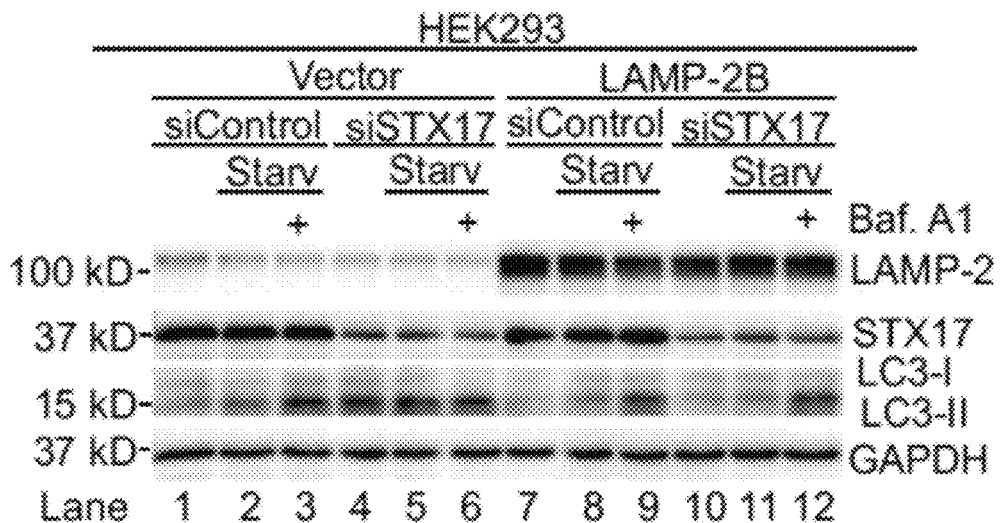
Figure 4C:
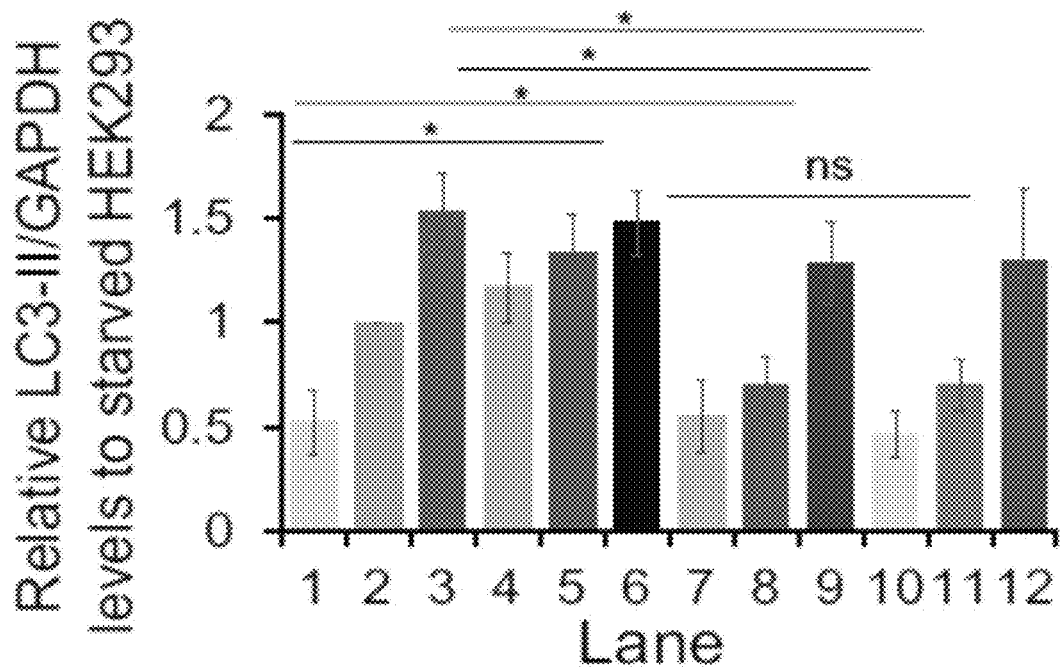
Figure 4D:
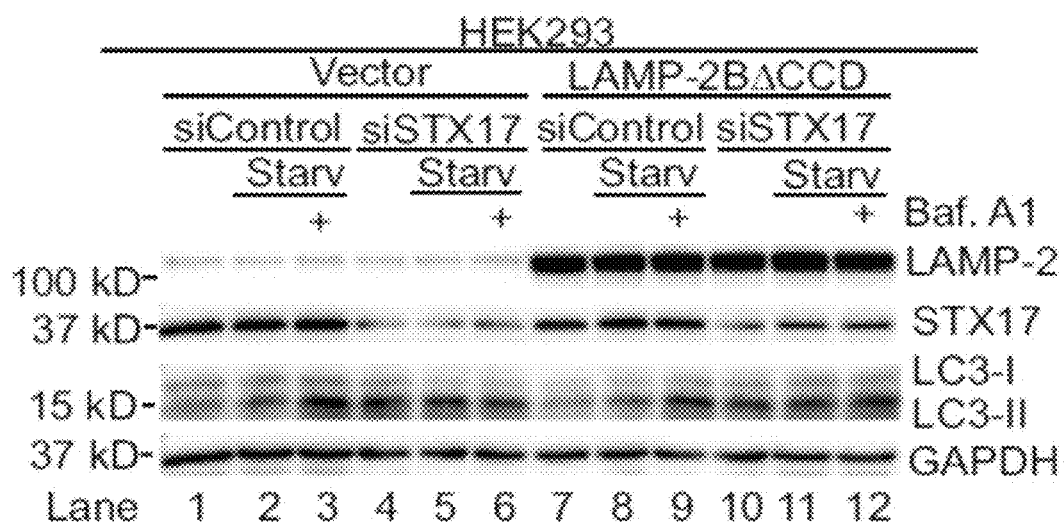
Figure 4E:
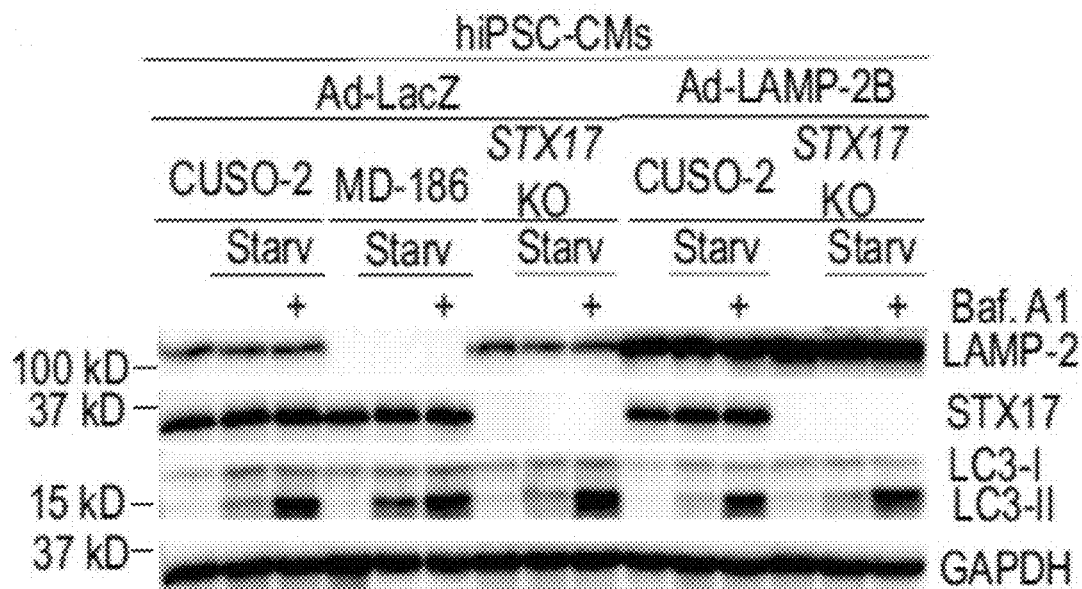
Figure 4F:
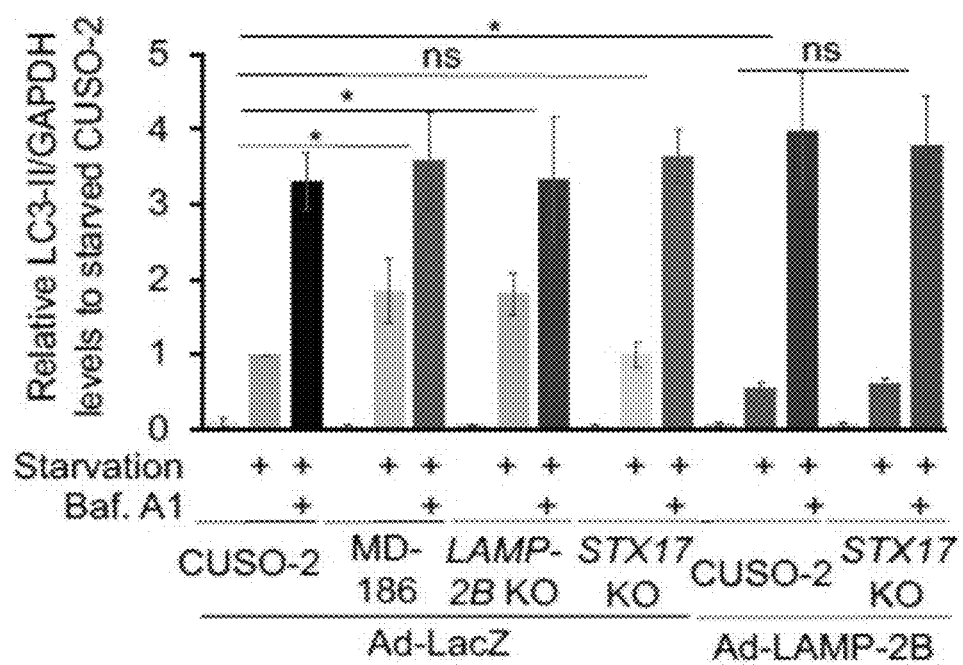
Figure 5A:
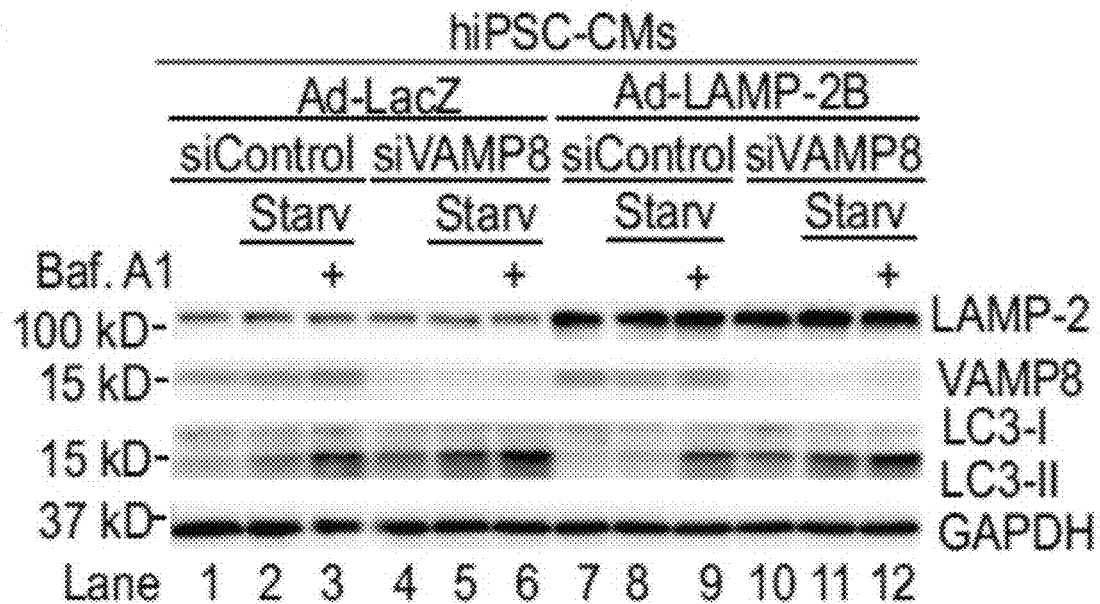
FIGS. 5A-D depict that both VAMP8 and ATG14 are involved for LAMP-2B to promote fusion between autophagosomes and endosomes/lysosomes for degradation. Immunoblotting analysis of indicated proteins in hiPSC-CMs. hiPSC-CMs infected with adenovirus carrying LacZ (Ad-LacZ) or LAMP-2B (Ad-LAMP-2B) were treated with siRNAs against luciferase, VAMP8 (in FIGS. 5A and 5B) or ATG14 (in FIGS. 5C and 5D). Three days later, cells were cultured in regular or starvation medium for 4 hours with or without 400 nM bafilomycin A1 (Baf. A1). Western blotting was performed with anti-LAMP-2, anti-LC3, anti-VAMP8 or anti-ATG14, and anti-GAPDH antibodies. Quantification of LC3-II/GAPDH from three independent experiments is shown in FIGS. 5B and 5D, with data being normalized to siControl-treated cells under starved conditions in each experiment. Data are presented as mean±SD. *P<0.05 as assessed by Student's t test.
Figure 5B:
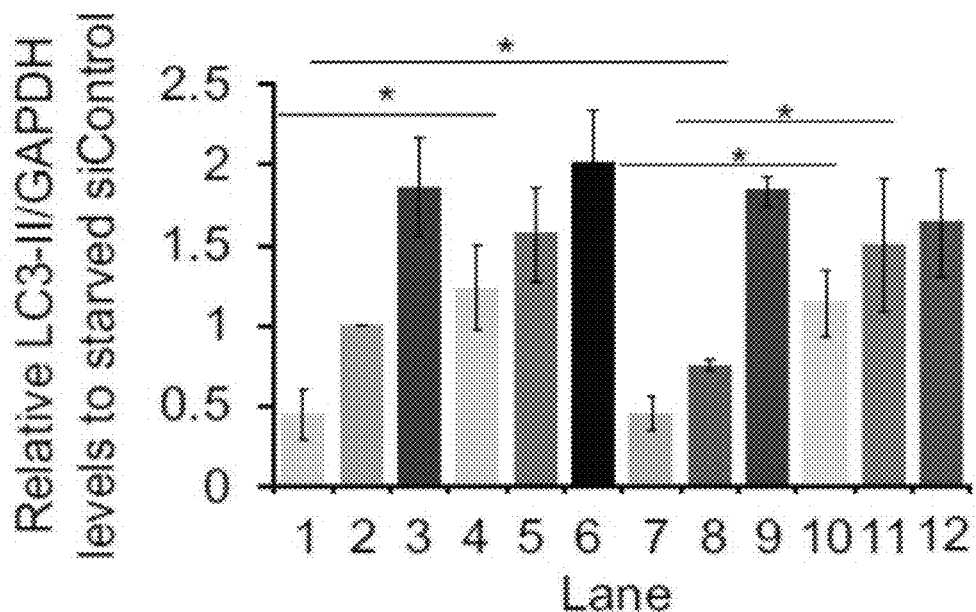
Figure 5C:
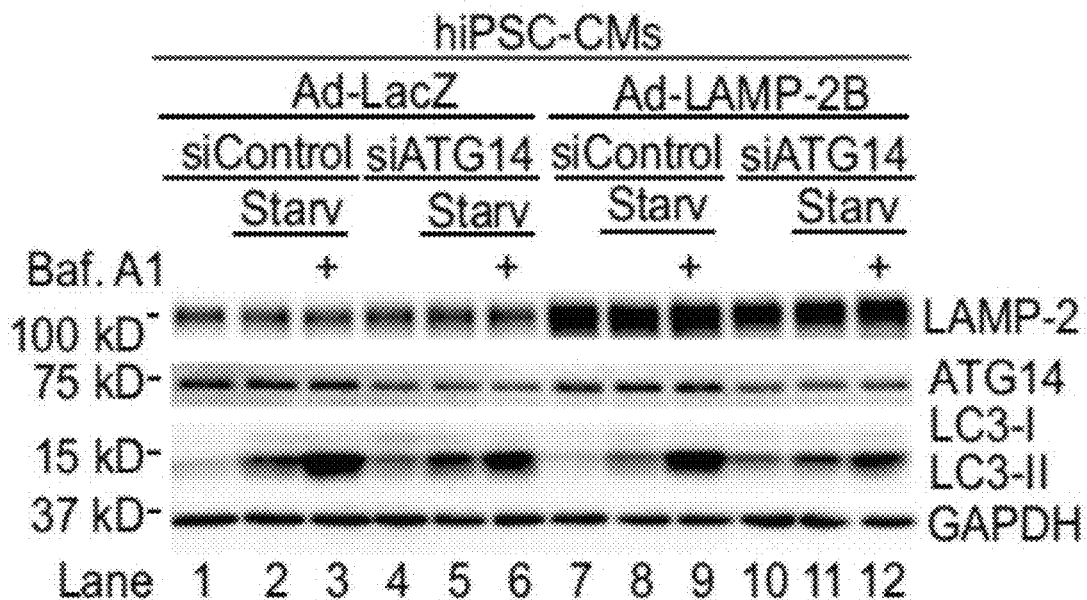
Figure 5D:
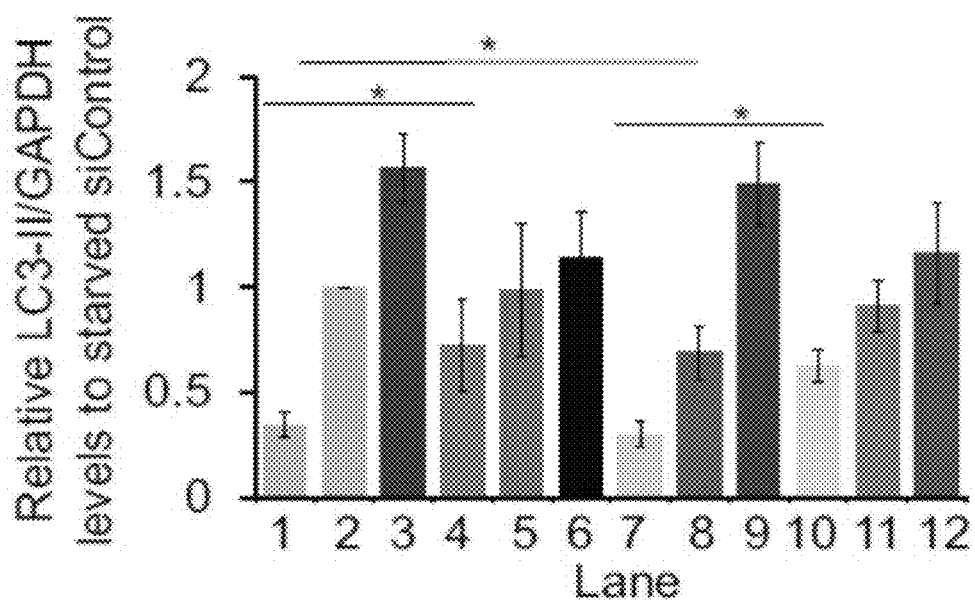

Intensive studies are believed to have demonstrated that LAMP-2A is involved for CMA by serving as a receptor for heat shock proteins. Previous studies concluded that LAMP-2A is involved for autophagy in MEFs. However, these studies, do not support that conclusion. First, overexpression of LAMP-2A in different types of cells did not change LC3-II levels (ref. 33; FIGS. 2C and 4A). Second, LAMP-2A deficiency in hiPSC-CMs did not cause accumulation of LC3-II under either regular or starvation conditions (FIG. 2A). Third, LAMP-2 deficiency in skin fibroblasts derived from Danon patients did not cause accumulation of LC3-II under either regular or starvation conditions, compared with control fibroblasts (See, FIG. 12B), despite LAMP-2A representing the dominant isoform in these cells. Therefore, LAMP-2A is dispensable for autophagosome-mediated autophagy.

Example 8—Apoptosis

Using Danon hiPSC-CMs, it was previously reported that 20-25% of Danon hiPSC-CMs underwent apoptosis. Subsequently, the same group used Danon hiPSC-CM lines to characterize mitochondrial function that was depressed. However, whether the observed decreased mitochondrial function is due to cardiomyocyte apoptosis in their Danon hiPSC-CM samples or due to some other mechanisms remains unclear. Controversially, significant apoptosis in Danon hiPSC-CMs was not detected in a more recent study. Consistent with these findings by Yoshida et al., these studies did not detect significant cardiomyocyte apoptosis in Danon or LAMP-2 KO hiPSC-CM lines cultured for 50 or 100 days (See, FIG. 9D). In addition, if 20-25% of cardiomyocytes were apoptotic in hearts of patients with Danon disease, the patients may survive beyond their teens. Therefore, cardiomyocyte apoptosis is unlikely to act as a primary contributor to Danon cardiomyopathy.

Aside from cardiomyopathy, muscle weakness, retinopathy, and intellectual disabilities have been observed in patients with Danon disease. LAMP-2B may promote autophagic fusion not only in cardiomyocytes, but also in HEK293 cells, suggesting a universal function for LAMP-2B in autophagy.

Example 9—Materials and Methods

Generation and Characterization of hiPSCs

Reprogramming of human skin fibroblast cells derived hiPSCs was performed following modification of a previous protocol. Human fibroblast cells were infected with retrovirus produced in L293 cells transfected with pMXs plasmid DNA (encoding Oct3/4, Sox2, Klf4, and c-Myc, respectively): pUMVC: pCMV-VSV-G (8:8:1) together with FuGENE6 (Promega) according to the manufacturer's protocol. After the infection, media was replaced by FP medium (DMEM/high glucose with 10% FBS, and 50 units and 50 mg/mL Penicillin and Streptomycin). Cells were replated to a 10 cm dish containing 2.4 million of mitomycin C-inactive SNL cells at day 5 and maintained with human ES medium. After 2 to 3 weeks, hiPSC colonies with ES-like morphology became visible and were picked at around day 30. After the hiPSC lines were established, cells were maintained in 12-well-plate coated with MatriGel (Corning) and fed with fresh mTeSR1 daily. When the cell confluence reached 70-85%, cells were dissociated with Gentle Cell Dissociation Reagent (STEMCELL Technologies) and split into a MatriGel coated dish with mTeSR1 (STEMCELL Technologies) supplemented with 10 µM Y-27632 (Enzo Life Sciences). After 24 h, media were replaced with mTeSR1.

To generate non-integrating iPSC lines, healthy male adult human dermal fibroblasts (Lonza, CC2511) were infected with CytoTune™-iPS 2.0 Sendai Reprogramming Kit (Thermo Fisher Scientifics) according to the manufacturer's instruction. Colonies were isolated 2 weeks after infection and passed in mTeSR1 for at least 10 passages until cells were clear of Sendai virus before used. hiPSC lines including CUSO-2, LAMP-2A KO, LAMP-2B KO and LAMP-2C KO were generated by the Sendai viral method.

To characterize the pluripotency of the generated hiPSCs, cells were replated to a 24-well-plate coated with MatriGel and fed with mTeSR1. After 3 days, cells were fixed with 4% PFA at room temperature for 20 min, and then blocked and permeabilized with PBS plus 10% horse serum (GEMINI) and 0.2% Triton at room temperature for 1 hour. Then, cells were stained with antibodies against SSEA-3 (Developmental Studies Hybridoma Bank, 1:10), SSEA-4 (Developmental Studies Hybridoma Bank, 1:10), TRA-2-49 (Developmental Studies Hybridoma Bank, 1:20), TRA-1-81 (Cell Signaling Technology; 1:20) or Nanog (Cell Signaling Technology, 1:100) at room temperature for 1 hour, followed by secondary antibody staining at room temperature for 1 hour.

To assess the differentiation potential of the generated hiPSC lines, the hiPSC colonies were detached via scratching with a cell lifter. The whole colonies were replated to a 60 mm non-tissue culture dish and cultured with Human ES medium without bFGF (STEMCELL Technologies) overnight. The embryoid bodies were harvested and replated to a 0.1% gelatin-coated tissue culture plate and maintained in Human ES medium without bFGF. Then, the cells were fixed and stained with ectoderm marker Tuj1 (Biolegend, 1:200), mesoderm marker SMA (Santa Cruz, 1:500) and endoderm al fetoprotein (R and D Systems, 1:100), respectively. Differentiation of hiPSCs into cardiomyocytes and culture of hiPSC-CMs.

At the time cells reached ~85% confluence, hiPSCs were dissociated as single cells with Accumax (STEMCELL Technologies) at 37° C. for 5 minutes and replated to a 24-well plate pre-coated with MatriGel. Cells were fed with 1 mL of mTeSR1 per well for 4 days before induction. At day 0, medium was changed to RPMI1640 (Life Technologies) with B27 supplement minus insulin (Life Technologies) plus 8 µM ChIR99021 (Cayman). On day 1 (24 h), medium was changed to RPMI1640 with B27 supplement minus insulin. On day 3 (72 h), media was replaced with combined medium (made by combining 0.5 mL of old medium with 0.5 mL fresh RPMI1640/B27 supplement minus insulin, supplemented with 5 µM IWP2 (Thermo Fisher Scientifics)). On day 5, media was replaced with fresh RPMI1640/B27 supplement minus insulin. On day 7, media was replaced with RPMI1640/B27 supplement (Life Technologies). Cells were then maintained in RPMI1640/B27 medium with medium changed every 3 days. Contracting cells were observed starting on day 7. On day 20, hiPSC-CMs were enriched by lactate selection, using glucose free DMEM supplemented with 4 mM lactate, for 5 days. To quantify the percentage of hiPSC-CMs in the total cell population, cells were fixed and stained with cTnT (Thermo Scientific, 1:400) followed by flow cytometry analysis.

CRISPR/Cas9-Mediated Genome Editing in hiPSCs

SgRNAs for gene specific targeting were designed using the online tool on http://crispr.mit.edu website. The targeting RNP complex, composed of synthetic Alt-R CRISPR-Cas9 crRNAs (IDT), Alt-R CRISPR-Cas9 tracrRNA (IDT), Alt-R Cas9 Electroporation Enhancer (IDT) and Alt-R S.p. Cas9 Nuclease 3NLS (IDT), was delivered into hiPSCs by electroporation with the Amaxa human stem cell nucleofector starter kit (Lonza). After electroporation, single cell clones were collected and cultured for genotyping by PCR to confirm the targeting event. The genomic sequence of positive clone of edited hiPSCs was determined by Sanger sequencing. The sequences for sgRNAs and genotyping PCR primers used in this study were listed in Tables 2 and 3.

TABLE 2

SgRNAs for CRISPR/Cas9-mediated genome editing.

| SgRNA ID | Target exon | Target region (PAM is underlined) | 20-nt sgRNA sequence |
|---|---|---|---|
| SgRNA1 | LAMP-2 exon2 | AGAAGTTTTACA CCCCTACCAGG | AGAAGUUUUA CACCCCUACC |
| SgRNA2 | LAMP-2 exon2 | ATGATCTGAAGA CGACTATATGG | AUGAUCUGAA GACGACUAUA |
| SgRNA-A1 | LAMP-2 exon 9A | ACTTCCTAACAC GCATATTTTGG | ACUUCCUACC ACGCAUAUUU |
| SgRNA-A2 | LAMP-2 exon 9A | TTGGGTCTGTAT CATCCCTAGGG | UUGGGUCUGU AUCAUCCCUA |
| SgRNA-B1 | LAMP-2 exon 9B | CAACTTCAAGTA ACTAAGACAGG | CAACUUCAAG UAACUAAGAC |
| SgRNA-B2 | LAMP-2 exon 9B | GGCCTCGATTGA TGCTAGGCAGG | GGCCUCGAUU GAUGCUAGGC |
| SgRNA-C1 | LAMP-2 exon 9C | GCAAGCGCAATT CTCTATTTTGG | GCAAGCGCAA UUCUCUAUUU |
| SgRNA-C2 | LAMP-2 exon 9C | TGGAACACCTGT ATGGGTTATGG | UGGAACACCU GUAUGGGUUA |
| SgRNA-S1 | STX17 exon 4 | ATATAGTGTAAC CATTGAGCAGG | AUAUAGUGUA ACCAUUGAGC |
| SgRNA-S2 | STX17 exon 4 | GTCCAAGGATTC AGCATATTGGG | GUCCAAGGAU UCAGCAUAUU |
| SgRNA-for correction | LAMP-2 exon 3 | TCCGAACTGCAC TGCTATTTTGG | UCCGAACUGC ACUGCUAUUU |
| Repair ssDNA for correction | LAMP-2 exon 3 | TTCAGACCATGG CACTGTGACATA TAATGGAAGCAT TTGTGGGGATGA TCAGAATGGTCC CAAAATAGCAGT GCAGTTCGGACC TGGCTTTTCCTG GATT | |

TABLE 3

PCR primers.

| Primer ID | Sequence | Note |
|---|---|---|
| hLAMP2A_qPRC_f | GTTCAGCCTTTCAATGTGACAC | |
| hLAMP2A_qPCR_r | CACTAGAATAAGTACTCCTGCCAAG | |
| hLAMP2B_qPCR_f | GGTTCAGCCTTTCAATGTGAC | |
| hLAMP2B_qPCR_r | TGAAAGACCAGCACCAACTAT | |

TABLE 3-continued

PCR primers.

| Primer ID | Sequence | Note |
|---|---|---|
| hLAMP2C_qPCR_f | CCCCTGGGAAGTTCTTATATGTG | |
| hLAMP2C_qPCR_r | AAAGTTGAGGTCAGAGTCAGC | |
| hGAPDH_qPCR_f | CTCTGGTAAGTGGATATTGTTGCC | |
| hGAPDH_qPCR_r | AGAGATGATGACCCTTTTGGCTCC | |
| Linker_sense | ATCAGACTCTGTAATCCGG | LAMP-2B |
| Linker_antisense | ATTACAGAGTCTGAT | |
| Q5_hLAMP2BΔCCD_f | TAATCCGGCCGCGGTCAT | LAMP-2BΔCCD |
| Q5_hLAMP2BΔCCD_r | GCCAATTACGTAAGCAATCACTAT AACG | |
| hLAMP-2A_Sgfl_f | GCGATCGCCATGGTGTGCTTCCGC CTCTTC | LAMP-2A |
| hLAMP-2A_Sacll_r | CCGCGGCTAAAATTGCTCATATCC AGCATGATG | |
| P-f | CGTTTGGGAAGACATCCGTG | Genotyping of LAMP-2 KO |
| P-r | CCAGTGTTGTAGGAAAATGAGACGC | |
| $P_A$-f | GCACTTTGTGTTGCCTACTCCTACC | Genotyping of LAMP-2A KO |
| $P_A$-r | ACTGCCTCCCTTCTGAGATTGC | |
| $P_B$-f | CCACTGAGAGGCTAATCTGGCTATG | Genotyping of LAMP-2B KO |
| $P_B$-r | TCACTGGTTCCCTAACTGACTAGC | |
| $P_C$-f | TGGTTCGGTGGAATGGACTG | Genotyping of LAMP-2C KO |
| $P_C$-r | TCACATAGGGAATGGGAGAGTGC | |
| $P_S$-f | GGCAGCATGTGAAGAAATAGGC | Genotyping of STX17 KO |
| $P_S$-r | TCCCTGAAGTCCCACTCCATAAGC | |
| $P_{MD-186}$-f | CCAGAGGAGTGGTATGTAGCAGAAG | Genotyping of MD-186C |
| $P_{MD-186}$-r | CCAGTGTTGTAGGAAAATGAGACGC | |

Analysis of Glycogen and Vacuole Accumulation

For glycogen accumulation, Periodic Acid-Schiff (PAS) staining was performed using the Periodic Acid-Schiff Kit (Sigma). Cells were fixed in 4% formaldehyde for 2 min, washed with 1×TBST, stained for 5 minutes with periodic acid, and washed 3 times with DPBS. Cells were then stained with Schiff's reagent for 15 min, washed 3 times with DPBS, counterstained with hematoxylin solution for 90 sec, and washed 3 times with DPBS before imaging.

For vacuole accumulation, cells were fixed in 2% Paraformaldehyde/2.5% Glutaraldehyde at room temperature for 1 hour. Fixation solution was then removed and replaced with 0.1 M Cacodylate buffer (Electron Microscopy Sciences). Further sample preparation and electron microscopy imaging was performed.

TUNEL Assay

To assess cell death, TUNEL staining was performed using the In Situ Cell Death Detection Kit TMR red (Roche) according to the manufacturer's manual. Cells were fixed with 4% PFA for 1 hour at room temperature and permeabilized using 0.1% Triton X-100 in 0.1% sodium citrate for 2 minutes on ice. Cells were then incubated in the labeling enzyme solution in a 37° C.-humidified chamber for 1 hour. This was followed by co-immunostaining with the cardiac marker cTnT (Thermo Scientific, 1:400) before imaging. Cells treated with DNase I (Sigma) or pretreated with 10 µM H2O2 (Sigma) for 24 hours were used as positive controls.

Starvation Assays

For starvation, cells were washed with DPBS (Dulbecco's phosphate-buffered saline) three times and incubated in starvation medium at 37° C. for 1, 2 or 4 hours. For cardiomyocytes, glucose-free DMEM (gibco) was used as starvation medium; for non-CMs, the composition of the starvation medium is as previously described. To block autophagy flux, 400 nM of bafilomycin A1 was added to the starvation medium.

Plasmids and Cloning

HA-ATG14, FLAG-STX17, FLAG-SNAP29 and FLAG-VAMP8 plasmids were purchased from Addgene. Human LAMP-2B cDNA clone was purchased from Origene. The C-terminus Myc-DDK tag was removed by digesting the plasmid with EcoRV and FseI, and then ligated with a DNA linker containing a stop codon. The resulting tag-free LAMP-2B cDNA plasmid was then used for this study. LAMP-2BΔCCD plasmid was generated by removing the cytosolic coiled coil domains (RRKSYAGYQTL) using the Q5 Site-Directed Mutagenesis Kit (NEB) according to manufacturer's instructions. LAMP-2A cDNA was PCR amplified from a reverse transcripted cDNA library from total RNA isolated from HEK293 cells and subcloned into the same backbone as the tag-free LAMP-2B cDNA plasmid by SgfI and SacII. The sequences for the DNA linker and cloning primers were listed in Table 3.

siRNA Treatments.

Negative control and gene-specific siRNAs were purchased from Dharmacon. siRNAs were delivered into the target cells with Lipofectamine RNAiMAX (Invitrogen, for non-CMs) or Lipofectamine 3000 (Invitrogen, for cardiomyocytes) reagents according to the manufacturer's protocols. Cells were incubated with siRNA for 48 hours before switching to regular culture medium for recovery. Cells were lysed at 72-hours post infection for downstream protein analysis.

Immunostaining and Microscopy Imaging

Cells were fixed in 2% paraformaldehyde for 30 minutes at room temperature and then washed 3 times with DPBS. The cells were permeabilized in 0.5% Triton X-100 for 20 minutes at room temperature. After blocking in DPBS containing 10% horse serum for 30 minutes at room temperature, cells were incubated with primary antibodies against α-actinin (Sigma, 1:500), cTnT (Thermo Scientific, 1:400), cTnI (PhosphoSolutions, 1:500), MYL2 (Proteintech, 1:200), HA (UBPBio, 1:500), FLAG (Gallus Immunotech, 1:500), and/or LC3B (Sigma, 1:250) in 10% horse serum in DPBS for 1 hour at room temperature. Cells were washed 3 times with DPBS and then incubated with secondary antibodies (Molecular Probes Alexa Fluor 488, 1:400 or Alexa Fluor 555, 1:1,000; Abcam Alexa Fluor 647, 1:400) and Hoechst (Molecular Probes, 1:5,000) for 30 minutes at room temperature. Cells were washed 3 times with DPBS before imaging by either EVOS FL Cell Imaging System (Life Technologies) or Olympus FV1000 FCS/RICS confocal microscope. For confocal microscopy, images were acquired using a 60× or 100× oil-immersion objective lens, and different fluorescent channels were captured individually and merged using Fluoview software (Olympus). For co-staining with LysoTracker, live hiPSC-CMs were incubated with 100 nM LysoTracker Red DND-99 (Molecular Probes) in culture medium for 30 minutes at 37° C. before fixation.

Immunoblotting and Gene Expression Analysis

For immunoblotting, cells were washed with ice-cold DPBS twice before lysing in ice-cold lysis buffer (150 mM NaCl, 50 mM Tris-Cl pH 7.4, 1 mM EDTA, 1% Triton, with Complete mini tablet (Roche), and 1 mM phenylmethylsulphonyl fluoride freshly added before use). 10 µg of lysate per sample was loaded for Western blot analysis. The primary antibodies used include the following: anti-OPA1 (BD Biosciences, 1:1,000), anti-Pink1 (Novus Biologicals, 1:1,000), anti-VDAC (Cell signaling, 1:1,000), anti-LC3B (Sigma, 1:1,000), anti-LAMP-1 (Santa Cruz, 1:500), anti-LAMP2 (Developmental Studies Hybridoma Bank, 1:1,000), anti-STX17 (Sigma, 1:500), anti-VAMP8 (Sigma, 1:1,000), anti-ATG14 (Cell signaling, 1:1,000), anti-HA (UBPBio, 1:1, 000), anti-HA (Rockland, 1:4,000), anti-FLAG (UBPBio, 1:1,000), anti-FLAG M2-Peroxidase (Sigma, 1:5000) and anti-GAPDH (Ambion, 1:5,000). The secondary antibodies used include the following: Goat Anti-Mouse IgG (Southern Biotech, 1:2,000) and Goat Anti-Rabbit IgG (Life Technologies, 1:2,000). For separation of MYH6 and MYH7, cell lysates were run on a modified 6% SDS-PAGE (separating acrylamide/bis ratio 1:100; resolving gel buffer pH 9.0; running gel buffer pH 8.2; β-mercaptoethanol 600 µl/L inner gel buffer). Gels were run overnight at 4° C. and stained with BioSafe Coomassie Blue protein stain (Bio-Rad).

For gene expression analysis, total RNA was extracted with TRizol reagent (Invitrogen) and the RNeasy Plus Universal Mini Kit (Qiagen). cDNA was synthesized with the Superscript III First-Strand Synthesis System (Invitrogen). qPCR was performed using the SYBR Green PCR Master Mix (Applied Biosystems). GAPDH was used as an internal control. The primers for qPCR are listed in Table 3.

Transcriptome Analysis

Total RNA from hiPSC-CMs was extracted with TRIzol reagent (Invitrogen) and purified with the RNeasy Plus Universal Mini Kit (Qiagen). The sequencing libraries preparation and RNA-seq were performed using a HiSeq 4000 sequencing system (Illumina). FastQC was used for the raw RNA-seq reads for the control of sequence quality, GC content, the presence of adaptor sequences and duplicated reads and ensure homogeneity of sequencing reads between samples. The reads passed quality control were aligned to NCBI GRCh38 human reference genome with Bowtie2. The read count per gene was generated from the aligned sequencing reads using HTSeq 0.9.1 with GTF file for NCBI GRCh38. DESeq2 was used perform normalization of read counts across samples and differential expression analysis between Danon and control samples. The differentially expressed genes with >1.5 fold expression change were used in the heatmap. Gene ontology analysis was performed using the web-based gene set analysis toolkit (http://webgestalt.org). For RNA-sequencing of adult mouse cardiomyocytes, ventricular cardiomyocytes were isolated from adult mouse hearts using a Langendorff perfusion system. Total RNA was isolated using Trizol reagent (Ambion) and genomic DNA was removed with the TURBO DNase I kit (Ambion). RNA concentration and quality were assessed with the Agilent Bioanalzyer (Agilent, Santa Clara, Calif.). Library construction was prepared using the TruSeq RNA sample Preparation Kit (Illumina) and sequenced using an Illumina HiSeq2500 (Illumina, Santa Clara, Calif.) with a read depth of 20-25 million reads at 1×100 bp. RNA-sequencing read densities (and sashimi plots) were generated using the Integrative Genomics Viewer (http://software.broadinstitute.org/software/igv/).

All RNA-seq data have been deposited in the Gene Expression Omnibus (GEO). Accession numbers for those experiments reported herein are GSE71405 for NMCMs, GSE102792 for adult mouse cardiomyocytes and GSE108429 for hiPSCCMs.

Generation of Adenovirus and Infection

Adenovirus including Ad-LacZ, Ad-GFP, Ad-LAMP-2A, Ad-LAMP-2B, Ad-HA-ATG14, Ad-FLAG-VAMP8 and Ad-mRFP-EGFP-LC3 were generated using the ViraPower Adenoviral Gateway Expression Kit (Invitrogen). Genes of interested in this study were cloned to pENTR 2B (Invitrogen) to create the expression clones in the pAd/CMV/V5-DEST plasmid using Gateway® Technology (Invitrogen). Then, PacI digested pAd-DEST expression plasmids were transfected to 293A cells using Lipofectamine 3000 (Invitrogen) reagent. Crude viral lysate was collected 7-10 days post-transfection. For virus amplification, a 10 cm plate of 293A cells was infected with 500 μL of crude viral stock, and the amplified virus was harvested 2 days after infection. Plaque assays were performed to determine the titer of an adenoviral stock using the Seaplaque Agarose (Lonza). MOI of 5 was used for cardiomyocyte infection.

Transfection

Cell transfection was performed using Polyethylenimine (PEI, Sigma) or Lipofectamine 3000 (Invitrogen) reagents according to protocols provided by manufacturers. Cells were harvested 48 hours post transfection for immunoblotting or immunoprecipitation.

Coimmunoprecipitation Assays

Cells were lysed in ice-cold lysis buffer (150 mM NaCl, 50 mM Tris-Cl pH 7.4, 1 mM EDTA, 1% Triton, with Complete mini tablet (Roche), and 1 mM phenylmethylsulphonyl fluoride freshly added before use). Whole-cell lysates (input) were collected after removal of cell debris by centrifugation. 500 μg of lysate per sample was then incubated with indicated antibody and Dynabeads Protein G (Invitrogen) overnight at 4° C. to pull down protein complexes. Normal mouse IgG (Santa Cruz) was used to replace antibody in negative control samples. Beads were washed 4 times with ice-cold lysis buffer and boiled in 1×SDS loading buffer for 15 minutes to elute proteins. Eluted proteins were subjected to immunoblotting as described in the sub-section titled Immunoblotting and gene expression analysis.

Analysis of Mitochondrial Morphology and Membrane Potential

Live hiPSC-CMs were incubated with 200 nM MitoTracker Orange (for abundance, Molecular Probes) or 100 nM Tetramethylrhodamine (TMRM) (for membrane potential, Molecular Probes) in culture medium for 20 minutes or 30 minutes at 37° C. respectively. Cells were washed with DPBS and counterstained with 1 μg/mL DAPI (EMD Millipore) before being analyzed by flow cytometry. Fluoresce intensities of DAPI negative cells were analyzed by the FACS Caliber (BD Sciences) and FlowJo software. Mitochondrial morphology was examined using Olympus FV1000 FCS/RICS confocal microscope.

Measurement of Mitochondrial Function

For mitochondrial function assays, Seahorse XF Cell Mito Stress tests were performed according to manufacturer's instructions. 60,000 hiPSC-CMs were seeded in 0.1% gelatin-coated Seahorse assay wells. Culture medium was changed to Seahorse XF Cell Mito Stress Test kit assay medium (Seahorses Biosciences) with indicated supplements on the day of assay and incubated for 1 hour in a 37° C. non-CO2 incubator. Oxygen consumption rate (OCR) was measured using a Seahorses Biosciences extracellular flux analyzer with the Cell Mito Stress Kit (Seahorses Biosciences) and normalized to total cell number. Mitochondrial function metrics were calculated based on changes of OCR after addition of oligomycin (2.5 μM), FCCP (1 μM), or antimycin (2.5 μM)/rotenone (2.5 μM) as directed in the Cell Mito Stress Kit manual.

Measurement of Cellular ATP

Cellular ATP levels were measured by the ATP Bioluminescence Assay Kit HS II (Roche) according to manufacturer's instructions. 200,000 cells per sample were collected and lysed in the cell lysis reagent provided with the assay kit. The luminescence generated by incubating cell lysates with luciferase reagent was detected by a GloMax Multi Detection System (Promega) and the readout was normalized to cell number. The ATP level of each sample was then calculated based on the comparison to an ATP standard curve.

Measurement of Reactive Oxygen Species (ROS)

Live hiPSC-CMs were stained with 5 μM MitoSox (Molecular Probes) in culture medium for 10 minutes at 37° C. Cells were washed with DPBS and counterstained with 1 μg/mL DAPI (EMD Millipore) before being analyzed by flow cytometry. Fluoresce intensities of DAPI negative cells were analyzed by the FACS Caliber (BD Sciences) and FlowJo software.

Measurement of Autophagic Flux in hiPSC-CMs Using mRFP-EGFP-LC3 hiPSC-CMs were infected with Ad-mRFP-EGFP-LC3 at MOI of 5. Four days later, half of cells were washed with DPBS 3 times and treated with starved medium for 4 hours. Cells were incubated in DPBS for confocal imaging using Olympus FV1000 FCS/RICS confocal microscope. Images were acquired using a 60× water-immersion objective lens, and different fluorescent channels were captured individually and merged using Fluoview software (Olympus).

Isolation of Mitochondrial

Mitochondrial isolation from hiPSC-CMs was performed as previously described (12). About 2 million cells per sample were lysed in an ice-cold mitochondrial isolation buffer (MIB) containing: 200 mM mannitol, 70 mM sucrose, 5 mM HEPES and 1 mM EGTA, pH 7.5, and Complete mini tablet (Roche). Cell lysate was passed through a 1 mL syringe with a 26½ G needle 20 times. Lysate was then centrifuged at 600 g for 10 minutes at 4° C. The supernatant was transferred to a new 1.5 ml tube and centrifuged again at 14,000 g for 15 minutes at 4° C. The supernatant was collected in a separate tube as cytosolic fraction. Then, the pellet containing the mitochondria fraction was resuspended in fresh MIB buffer and centrifuged again at 14,000 g for 15 minutes at 4° C. The washed mitochondrial pellet was resuspended in MIB and directly used for protein quantification and immunoblotting.

Measurement of Human Heart Myofibril Mechanics

Human hearts from patients with Danon Disease were obtained from a tissue bank. Hearts were collected at the time of orthotropic cardiac transplantation. Control hearts were obtained from unused donor hearts that could not be used for transplantation.

Myofibril mechanics were quantified using the fast solution switching technique as described previously. Frozen LV sections were skinned in 0.5% Triton-X in rigor solution (132 mM NaCl, 5 mM KCl, 1 mM MgCl2, 10 mM Tris, 5 mM EGTA, pH 7.1) containing protease inhibitors (10 μM leupeptin, 5 μM pepstatin, 200 μM PMSF and 10 μM E64), as well as 500 μM NaN3 and 500 μM DTT at 4° C. overnight. Skinned LVs were washed in fresh rigor solution and homogenized (Tissue-Tearor, Thomas Scientific) in relaxing solution (pCa 9.0) containing protease inhibitors. Myofibril suspensions were transferred to a temperature controlled chamber (15° C.) containing relaxing solution. Myofibril bundles were mounted between two micro-tools. One tool was connected to a motor that could produce rapid length changes (Mad City Labs). The second tool was a calibrated cantilevered force probe (6-8 µM/µN; frequency response 2-5 KHz). Myofibrils were set 5-10% above slack myofibril length. Average sarcomere lengths and myofibril diameters were measured using ImageJ software. Mounted myofibrils were activated and relaxed by translating the interface between two flowing streams of solutions of different pCa. Maximal tension generation was collected and analyzed using customized LabView software. Maximal tension (mN/mm2) represents maximal tension generated at full calcium activation (pCa 4.5).

Measurement of Cardiomyocyte Contractility by Micropost Arrays hiPSC-CMs on day 50 were shipped. One week later, cardiomyocytes were seeded on microposts for experiments. Micropost experiments were blindedly conducted in Sniadecki Lab. Arrays of microposts were used to calculate the twitch force of individual cells following previously established protocols. Arrays of polydimethylsiloxane (PDMS) microposts with bending stiffness kpost=56.5 nN/µm were fabricated on glass coverslides (25 mm circle no. 2, VWR) through a soft lithography process. The spacing between posts was 6 µM. The tips of the microposts were coated with mouse laminin (Life Technologies) via microcontact printing, and the hiPSC-CMs were seeded onto the microposts in Attoflour® viewing chambers (Life Technologies) at a density of approximately 75,000 cells per cm2 in RPMI medium with B27 supplement and 10% fetal bovine serum. The following day, the media was removed and replaced with serum-free RPMI medium, which was exchanged every other day. Once the cells resumed beating (typically 3 to 5 days after seeding), contractions of individual cells were imaged (at a minimum of 70 FPS) using a Hamamatsu ORCA-Flash2.8 Scientific CMOS camera fitted on a Nikon Eclipse Ti upright microscope using a 60× water immersion objective. Prior to imaging, the cell culture media was replaced with a tyrode buffer containing 1.8 mM Ca2+, and a live cell chamber was used to maintain the cells at 37° C. throughout the imaging process. A custom-written matlab code was used to track the deflection, Δpost, of each post underneath a cell, and to calculate force, Fpost=kpost× Δpost. The reported values of twitch force were normalized by cell size by summing the twitch force at each post and dividing by the number of posts underneath an individual cell. The spread area of individual cardiomyocytes on microposts were calculated using the NIS-Elements area tool by hand-tracing the cell outline from the first frame of a video involved with the experiment.

Quantification and Statistical Analysis

Statistical significance was calculated using paired Student's t tests. P<0.05 was considered a significant difference. For quantification of Western blotting, gel images were quantified using densitometry analysis in Image J (NIH), and normalized to GAPDH. Data was collected from three independent experiments, normalized to a single control condition for each experiment. Statistical analysis of quantified gels was conducted in Graphpad Prism (Graphpad Software Inc.), using Student's t-test. P-values<0.05 were considered significant. For the micropost experiments, statistical analysis was performed on data sets where the average twitch force of each cell was considered as an individual data point. The data sets consisted of 3 or more independent differentiations for each cell line, with 20-25 cells from each batch. Parametric statistics were performed using a one way ANOVA ("anova1" function in MATLAB) with a Bonferroni post-hoc test (using the "multcompare" function in MATLAB) to determine statistical difference between groups. When comparing the mean values of the maximal tension of myofibrils between control and patients with Danon disease, a one-way ANOVA function in GraphPad with Tukey's multiple comparison test was used. The resulting p-value<0.05 was considered a significant difference between group means.

In some cases, editing the mutated form of the LAMP-2 gene includes a CRISPR technique targeted to the mutated form of the LAMP-2 gene. The CRISPR technique may include using a guide RNA (SgRNA). The SgRNA may be selected from at least the group consisting of AGAAGUUUUACACCCCUACC (SEQ. NO:1), AUGAUCUGAAGACGACUAUA (SEQ. NO:2), ACUUC-CUAACACGCAUAUUU (SEQ. NO:3), UUGGGUCU-GUAUCAUCCCUA (SEQ. NO:4), CAACUUCA-AGUAACUAAGAC (SEQ. NO:5), GGCCUCGAUUGAUGCUAGGC (SEQ. NO:6), GCAAGCGCAAUUCUCUAUUU (SEQ. NO:7), UGGAACACCUGUAUGGGUUA (SEQ. NO:8), AUAUAGUGUAACCAUUGAGC (SEQ. NO:9), GUC-CAAGGAUUCAGCAUAUU (SEQ. NO:10), and UCCGAACUGCACUGCUAUUU (SEQ. NO:11). In some cases, editing the mutated form of the LAMP-2 gene may include administering a LAMP-2 editing protein to at least one cell with a mutated form of the LAMP-2 gene. The LAMP-2 editing gene may be a CRISPR protein. The LAMP-2 editing gene may be a zinc finger nuclease. While multiple embodiments are disclosed, still other embodiments of the present invention will become apparent to those skilled in the art from the above detailed description. As will be apparent, the invention is capable of modifications in various obvious aspects, all without departing from the spirit and scope of the present invention. Accordingly, the detailed description is to be regarded as illustrative in nature and not restrictive or limiting.

All references disclosed herein, whether patent or non-patent, are hereby incorporated by reference as if each was included at its citation, in its entirety. In case of conflict between reference and specification, the present specification, including definitions, will control.

Although the present disclosure has been described with a certain degree of particularity, it is understood the disclosure has been made by way of example, and changes in detail or structure may be made without departing from the spirit of the disclosure as defined in the appended claims.

We claim:

1. A method of making a modified cell comprising:
    introducing a nuclease molecule into a cell of a human subject, the nuclease molecule targeting a nucleic acid sequence within one or more of exon 3, exon 8, or IVS-1 of a genomic sequence of the LAMP-2 gene comprising at least one mutation, wherein the cell expresses a mutant LAMP-2 gene resulting in the subject suffering from Danon disease;
    reverting the at least one mutation in the LAMP-2 genomic locus to create an edited LAMP-2 gene; and
    allowing the cell to express the edited LAMP-2 gene.

2. The method of claim 1, wherein the nuclease molecule is selected from a Transcription activator-like effector nuclease (TALEN), a zinc finger nuclease (ZFN), or a Cas9 nuclease.

3. The method of claim 2, wherein the nuclease molecule is a Cas 9 nuclease;
    further comprising introducing a guide RNA comprising a nucleotide sequence complementary to the targeted nucleic acid sequence within the LAMP-2 genomic sequence, wherein the at least one mutation in the LAMP-2 genomic locus results in expression of a mutant LAMP-2B gene; and
    introducing a template nucleic acid into the cell, the template nucleic acid sequence comprising at least a portion of a non-mutant targeted nucleic acid sequence, wherein the guide RNA sequence binds to the target nucleic acid sequence and the Cas9 nuclease cleaves the target nucleic acid sequence, and wherein a portion of the genomic LAMP-2 sequence comprising one or more mutations is modified to produce an edited LAMP-2 gene in the modified cell.

4. The method of claim 3, wherein the guide RNA molecule, the Cas9 nuclease, and the template nucleic acid are introduced into the cell via adenovirus or adeno-associated virus.

5. The method of claim 1, wherein the genomic LAMP-2 sequence codes for a mutated LAMP-2B isoform, that is corrected upon editing of the genomic sequence.

6. The method of claim 3, wherein the guide RNA molecule comprises a targeting domain complementary to a target domain in the LAMP-2 gene.

7. The method of claim 3, wherein:
    the at least one mutation is selected from a T at position 247 of exon 3, a delA at position 1082 of exon 8, and an A at position c.64+1 of IVS-1; and
    wherein the mutation is substitution through homology-directed repair by a 100-mer single-strand DNA oligonucleotide containing a non-mutant LAMP-2 sequence.

8. The method of claim 3, wherein the guide RNA comprises a nucleotide sequence

```
                                        (SEQ. NO: 11)
UCCGAACUGCACUGCUAUUU.
```

9. The method of claim 1, wherein the introducing step includes administering to the subject a therapeutically effective amount of the nuclease molecule.

10. The method of claim 3, wherein the cell is a cardiomyocyte.

11. A composition for use in editing a genomic LAMP-2 gene, the composition comprising: an isolated nucleic acid sequence encoding a Clustered Regularly Interspaced Short Palindromic Repeat-associated endonuclease and at least one single guide RNA (SgRNA), the SgRNA being complementary to a target sequence in a genomic locus of a LAMP-2 gene selected from one of exon 3, exon 8, or IVS-1; and wherein the composition allows for correcting one or more mutations in the genomic LAMP-2 gene expression of which results in a mutant LAMP-2B protein and Danon disease in a subject.

12. The composition of claim 11, wherein the one or more mutations in the LAMP-2 genomic locus is a T in the genomic sequence of LAMP-2 gene, wherein the composition replaces the T with C through homology-directed repair between the genomic gene sequence and the SgRNAa.

13. A method of treating Danon disease in a subject comprising:
    introducing a nuclease molecule into a cell of the subject, the nuclease molecule targeting a nucleic acid sequence within a LAMP-2 genomic locus comprising at least one mutation within one or more of exon 3, exon 8, or IVS-1 of the genomic sequence of the LAMP-2 gene, wherein the cell expresses a mutant LAMP-2 gene;
    reverting the at least one mutation in the LAMP-2 genomic locus to create an edited LAMP-2 gene; and
    allowing the cell to express the edited LAMP-2 gene in the modified cell.

14. The method of claim 13, wherein the cell is a human cell, and the nuclease molecule is selected from a Transcription activator-like effector nuclease (TALEN), a zinc finger nuclease (ZFN), or a Cas 9 nuclease.

15. The method of claim 12, wherein the cell is a human cardiomyocyte, and the nuclease molecule is a Cas 9 nuclease;
    further comprising introducing a guide RNA comprising a nucleotide sequence complementary to the targeted nucleic acid sequence within a LAMP-2 genomic locus; and
    introducing a template nucleic acid into the cell, the template nucleic acid sequence comprising at least a portion of the non-mutant targeted nucleic acid sequence,
        wherein the guide RNA sequence binds to the target nucleic acid sequence and the Cas 9 nuclease cleaves the target nucleic acid sequence, and wherein a portion of the genomic LAMP-2 sequence comprising one or more mutations is modified to produce an edited LAMP-2 gene in the modified cell.

16. The method of claim 13, wherein the guide RNA molecule, the Cas9 nuclease, and the template nucleic acid are introduced into the cell via adenovirus or adeno-associated virus.

17. The method of claim 13, wherein the mutant LAMP-2 gene codes for a mutated LAMP-2B isoform, that is corrected upon reverting the at least one mutation in the genomic sequence.

18. The method of claim 15, wherein the guide RNA molecule comprises a nucleotide sequence complementary to a target nucleic acid sequence within exon 3, exon 8, or IVS-1 of the LAMP-2 gene.

19. The method of claim 18, wherein: the target nucleic acid sequence within exon 3 of the LAMP-2 gene and is near a mutation gene segment (c.247C>T); and the method includes replacing the T at position 247 with a C through homology-directed repair by a 100-mer single-strand DNA oligonucleotide containing a normal LAMP-2 sequence.

20. The method of claim 15, wherein the guide RNA comprises a nucleotide sequence (SEQ. NO: 11)
UCCGAACUGCACUGCUAUUU.

* * * * *

SEQUENCE LISTING

<160> NUMBER OF SEQ ID NOS: 76

<210> SEQ ID NO 1

```
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
agaaguuuua caccccuacc                                                  20

<210> SEQ ID NO 2
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
augaucugaa gacgacuaua                                                  20

<210> SEQ ID NO 3
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
acuuccuaac acgcauauuu                                                  20

<210> SEQ ID NO 4
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
uugggucugu aucauccccua                                                 20

<210> SEQ ID NO 5
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
caacuucaag uaacuaagac                                                  20

<210> SEQ ID NO 6
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
ggccucgauu gaugcuaggc                                                  20

<210> SEQ ID NO 7
<211> LENGTH: 20
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
gcaagcgcaa uucucuauuu                                              20

<210> SEQ ID NO 8
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
uggaacaccu guauggguua                                              20

<210> SEQ ID NO 9
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
auauagugua accauugagc                                              20

<210> SEQ ID NO 10
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
guccaaggau ucagcauauu                                              20

<210> SEQ ID NO 11
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
uccgaacugc acugcuauuu                                              20

<210> SEQ ID NO 12
<211> LENGTH: 23
<212> TYPE: DNA
<213> ORGANISM: Homo sapiens

<400> SEQUENCE: 12
agaagtttta caccctacc agg                                           23

<210> SEQ ID NO 13
<211> LENGTH: 23
<212> TYPE: DNA
<213> ORGANISM: Homo sapiens

<400> SEQUENCE: 13
```

```
atgatctgaa gacgactata tgg                                              23

<210> SEQ ID NO 14
<211> LENGTH: 23
<212> TYPE: DNA
<213> ORGANISM: Homo sapiens

<400> SEQUENCE: 14
acttcctaac acgcatattt tgg                                              23

<210> SEQ ID NO 15
<211> LENGTH: 23
<212> TYPE: DNA
<213> ORGANISM: Homo sapiens

<400> SEQUENCE: 15
ttgggtctgt atcatcccta ggg                                              23

<210> SEQ ID NO 16
<211> LENGTH: 23
<212> TYPE: DNA
<213> ORGANISM: Homo sapiens

<400> SEQUENCE: 16
caacttcaag taactaagac agg                                              23

<210> SEQ ID NO 17
<211> LENGTH: 23
<212> TYPE: DNA
<213> ORGANISM: Homo sapiens

<400> SEQUENCE: 17
ggcctcgatt gatgctaggc agg                                              23

<210> SEQ ID NO 18
<211> LENGTH: 23
<212> TYPE: DNA
<213> ORGANISM: Homo sapiens

<400> SEQUENCE: 18
gcaagcgcaa ttctctattt tgg                                              23

<210> SEQ ID NO 19
<211> LENGTH: 23
<212> TYPE: DNA
<213> ORGANISM: Homo sapiens

<400> SEQUENCE: 19
tggaacacct gtatgggtta tgg                                              23

<210> SEQ ID NO 20
<211> LENGTH: 23
<212> TYPE: DNA
<213> ORGANISM: Homo sapiens

<400> SEQUENCE: 20
atatagtgta accattgagc agg                                              23

<210> SEQ ID NO 21
<211> LENGTH: 23
<212> TYPE: DNA
<213> ORGANISM: Homo sapiens
```

<400> SEQUENCE: 21
gtccaaggat tcagcatatt ggg                                             23

<210> SEQ ID NO 22
<211> LENGTH: 23
<212> TYPE: DNA
<213> ORGANISM: Homo sapiens

<400> SEQUENCE: 22
tccgaactgc actgctattt tgg                                             23

<210> SEQ ID NO 23
<211> LENGTH: 100
<212> TYPE: DNA
<213> ORGANISM: Homo sapiens

<400> SEQUENCE: 23
ttcagaccat ggcactgtga catataatgg aagcatttgt ggggatgatc agaatggtcc     60
caaaatagca gtgcagttcg gacctggctt ttcctggatt                          100

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gttcagcctt tcaatgtgac ac                                              22

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cactagaata agtactcctg ccaag                                           25

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ggttcagcct ttcaatgtga c                                               21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tgaaagacca gcaccaacta t                                               21

```
<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cccctgggaa gttcttatat gtg                                           23

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
aaagttgagg tcagagtcag c                                             21

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ctctggtaag tggatattgt tgcc                                          24

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
agagatgatg acccttttgg ctcc                                          24

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
atcagactct gtaatccgg                                                19

<210> SEQ ID NO 33
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
attacagagt ctgat                                                    15

<210> SEQ ID NO 34
```

```
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
taatccggcc gcggtcat                                                    18

<210> SEQ ID NO 35
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gccaattacg taagcaatca ctataacg                                         28

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gcgatcgcca tggtgtgctt ccgcctcttc                                       30

<210> SEQ ID NO 37
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ccgcggctaa aattgctcat atccagcatg atg                                   33

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cgtttgggaa gacatccgtg                                                  20

<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ccagtgttgt aggaaaatga gacgc                                            25

<210> SEQ ID NO 40
<211> LENGTH: 25
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gcactttgtg ttgcctactc ctacc                                            25

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
actgcctccc ttctgagatt gc                                               22

<210> SEQ ID NO 42
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ccactgagag gctaatctgg ctatg                                            25

<210> SEQ ID NO 43
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tcactggttc cctaactgac tatgc                                            25

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tggttcggtg gaatggactg                                                  20

<210> SEQ ID NO 45
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
tcacataggg aatgggagag tgc                                              23

<210> SEQ ID NO 46
<211> LENGTH: 22
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 46
ggcagcatgt gaagaaatag gc                                          22

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
tccctgaagt cccactccat aagc                                        24

<210> SEQ ID NO 48
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ccagaggagt ggtatgtagc agaag                                       25

<210> SEQ ID NO 49
<211> LENGTH: 11
<212> TYPE: PRT
<213> ORGANISM: Homo sapiens

<400> SEQUENCE: 49

Arg Arg Lys Ser Tyr Ala Gly Tyr Gln Thr Leu
1               5                   10

<210> SEQ ID NO 50
<211> LENGTH: 20
<212> TYPE: RNA
<213> ORGANISM: Artificial Sequence
<220> FEATURE:
<223> OTHER INFORMATION: guide_RNA

<400> SEQUENCE: 50
ggcggacaga cuaaucggga                                             20

<210> SEQ ID NO 51
<211> LENGTH: 100
<212> TYPE: DNA
<213> ORGANISM: Artificial Sequence
<220> FEATURE:
<223> OTHER INFORMATION: Repair ssDNA

<400> SEQUENCE: 51
ctcttcccgg ttccgggctc agggctcgtt ctggtctgcc tagtcctggg tgagttgtcg    60
ggccctcccg attagtctgt ccgcctgggc ccggggcacc                         100

<210> SEQ ID NO 52
<211> LENGTH: 20
<212> TYPE: RNA
<213> ORGANISM: Artificial Sequence
<220> FEATURE:
<223> OTHER INFORMATION: guide_RNA

<400> SEQUENCE: 52
cagccuuuca augugacaca                                               20

<210> SEQ ID NO 53
<211> LENGTH: 100
<212> TYPE: DNA
<213> ORGANISM: Artificial Sequence
<220> FEATURE:
<223> OTHER INFORMATION: Repair ssDNA

<400> SEQUENCE: 53
aagaacataa attattaatg aagtttgctt gattcttacc tgtagaatac tttccttgtg    60
tcacattgaa aggctgaacc cttagatcaa aggtatttat                         100

<210> SEQ ID NO 54
<211> LENGTH: 20
<212> TYPE: RNA
<213> ORGANISM: Artificial Sequence
<220> FEATURE:
<223> OTHER INFORMATION: guide_RNA

<400> SEQUENCE: 54
cacagugcca uggucugaaa                                               20

<210> SEQ ID NO 55
<211> LENGTH: 100
<212> TYPE: DNA
<213> ORGANISM: Artificial Sequence
<220> FEATURE:
<223> OTHER INFORMATION: Repair ssDNA

<400> SEQUENCE: 55
gatgaatttc acagtacgct atgaaactac aaataaaact tataaaactg taaccatttc    60
agaccatggc actgtgacat ataatggaag catttgtggg                         100

<210> SEQ ID NO 56
<211> LENGTH: 20
<212> TYPE: RNA
<213> ORGANISM: Artificial Sequence
<220> FEATURE:
<223> OTHER INFORMATION: guide_RNA

<400> SEQUENCE: 56
cuggauugcg aauuuuacca                                               20

<210> SEQ ID NO 57
<211> LENGTH: 100
<212> TYPE: DNA
<213> ORGANISM: Artificial Sequence
<220> FEATURE:
<223> OTHER INFORMATION: Repair ssDNA

<400> SEQUENCE: 57
tgttatcacc agtgttgtag gaaaatgaga cgctgtcaat tgaataagta gatgctgcct    60
tggtaaaatt cgcaatccag gaaaagccag gtccgaactg                         100

<210> SEQ ID NO 58
<211> LENGTH: 20
<212> TYPE: RNA
<213> ORGANISM: Artificial Sequence
<220> FEATURE:
<223> OTHER INFORMATION: guide_RNA

<400> SEQUENCE: 58
gcugcagcug aacaucacuc                                               20

<210> SEQ ID NO 59
<211> LENGTH: 100
<212> TYPE: DNA
<213> ORGANISM: Artificial Sequence
<220> FEATURE:
<223> OTHER INFORMATION: Repair ssDNA

<400> SEQUENCE: 59
aaatgaaatg caaaaaggat gtattgataa agatagacac ctataccttta tcctgagtga    60 tgttcagctg cagccccatg gtagccagca gacaagtatc                          100

<210> SEQ ID NO 60
<211> LENGTH: 20
<212> TYPE: RNA
<213> ORGANISM: Artificial Sequence
<220> FEATURE:
<223> OTHER INFORMATION: guide_RNA

<400> SEQUENCE: 60
gcacauauaa gaacuuccca                                               20

<210> SEQ ID NO 61
<211> LENGTH: 100
<212> TYPE: DNA
<213> ORGANISM: Artificial Sequence
<220> FEATURE:
<223> OTHER INFORMATION: Repair ssDNA

<400> SEQUENCE: 61
gtttcttttc tttgaagttt tcagcattgc aaataacaat ctcagctact gggatgcccc    60
cctgggaagt tcttatatgt gcaacaaaga gcagactgtt                         100

<210> SEQ ID NO 62
<211> LENGTH: 20
<212> TYPE: RNA
<213> ORGANISM: Artificial Sequence
<220> FEATURE:
<223> OTHER INFORMATION: guide_RNA

<400> SEQUENCE: 62
auagugauug cuuacguaau                                               20

<210> SEQ ID NO 63
<211> LENGTH: 100
<212> TYPE: DNA
<213> ORGANISM: Artificial Sequence
<220> FEATURE:
<223> OTHER INFORMATION: Repair ssDNA

<400> SEQUENCE: 63
gagatcacgt attgattagt gttacagagt ctgatatcca gcataacttt ttcttctgcc    60
aattacgtaa gcaatcacta taacgataat caagcctgaa                         100

<210> SEQ ID NO 64
<211> LENGTH: 46
<212> TYPE: PRT
<213> ORGANISM: Artificial Sequence
<220> FEATURE:
<223> OTHER INFORMATION: LAMP-2A

<400> SEQUENCE: 64

Ala Gln Asp Cys Ser Ala Asp Asp Asn Phe Leu Val Pro Ile Ala
1               5                   10                  15

Val Gly Ala Ala Leu Ala Gly Val Leu Ile Leu Val Leu Leu Ala Tyr
            20                  25                  30

Phe Ile Gly Leu Lys His His His Ala Gly Tyr Glu Gln Phe
        35                  40                  45

<210> SEQ ID NO 65
<211> LENGTH: 46
<212> TYPE: PRT
<213> ORGANISM: Artificial Sequence
<220> FEATURE:
<223> OTHER INFORMATION: LAMP-2B

<400> SEQUENCE: 65

Ala Gln Glu Cys Ser Leu Asp Asp Thr Ile Leu Ile Pro Ile Ile
1               5                   10                  15

Val Gly Ala Gly Leu Ser Gly Leu Ile Ile Val Ile Val Ile Ala Tyr
            20                  25                  30

Val Ile Gly Arg Arg Lys Ser Tyr Ala Gly Tyr Gln Thr Leu
        35                  40                  45

<210> SEQ ID NO 66
<211> LENGTH: 47
<212> TYPE: PRT
<213> ORGANISM: Artificial Sequence
<220> FEATURE:
<223> OTHER INFORMATION: LAMP-2C

<400> SEQUENCE: 66

Ala Glu Glu Cys Ser Ala Asp Ser Asp Leu Asn Phe Leu Ile Pro Val
1               5                   10                  15

Ala Val Gly Val Ala Leu Gly Phe Leu Ile Ile Val Val Phe Ile Ser
            20                  25                  30

Tyr Met Ile Gly Arg Arg Lys Ser Arg Thr Gly Tyr Gln Ser Val
        35                  40                  45

<210> SEQ ID NO 67
<211> LENGTH: 42
<212> TYPE: DNA
<213> ORGANISM: Artificial Sequence
<220> FEATURE:
<223> OTHER INFORMATION: LAMP-2

<400> SEQUENCE: 67
gatgattaga atggtcccaa aatagcagtg cagttcggac ct                           42

<210> SEQ ID NO 68
<211> LENGTH: 42
<212> TYPE: DNA
<213> ORGANISM: Artificial Sequence
<220> FEATURE:
<223> OTHER INFORMATION: Repair ssDNA

<400> SEQUENCE: 68
gatgatcaga atggtcccaa aatagcagtg cagttcggac ct                           42

<210> SEQ ID NO 69
<211> LENGTH: 12
<212> TYPE: DNA
<213> ORGANISM: Artificial Sequence
<220> FEATURE:
<223> OTHER INFORMATION: nucleotide sequence

```
<400> SEQUENCE: 69
cctgggtgag tt                                                12

<210> SEQ ID NO 70
<211> LENGTH: 12
<212> TYPE: DNA
<213> ORGANISM: Artificial Sequence
<220> FEATURE:
<223> OTHER INFORMATION: nucleotide sequence

<400> SEQUENCE: 70
attctgatca tc                                                12

<210> SEQ ID NO 71
<211> LENGTH: 13
<212> TYPE: DNA
<213> ORGANISM: Artificial Sequence
<220> FEATURE:
<223> OTHER INFORMATION: nucleotide sequence

<400> SEQUENCE: 71
caaggaaagt att                                               13

<210> SEQ ID NO 72
<211> LENGTH: 12
<212> TYPE: DNA
<213> ORGANISM: Artificial Sequence
<220> FEATURE:
<223> OTHER INFORMATION: nucleotide sequence

<400> SEQUENCE: 72
cctggatgag tt                                                12

<210> SEQ ID NO 73
<211> LENGTH: 12
<212> TYPE: DNA
<213> ORGANISM: Artificial Sequence
<220> FEATURE:
<223> OTHER INFORMATION: nucleotie sequence

<400> SEQUENCE: 73
attctaatca tc                                                12

<210> SEQ ID NO 74
<211> LENGTH: 13
<212> TYPE: DNA
<213> ORGANISM: Artificial Sequence
<220> FEATURE:
<223> OTHER INFORMATION: nucleotide sequence

<400> SEQUENCE: 74
caaggaagta ttc                                               13

<210> SEQ ID NO 75
<211> LENGTH: 11
<212> TYPE: DNA
<213> ORGANISM: Artificial Sequence
<220> FEATURE:
<223> OTHER INFORMATION: nucleotide sequence

<400> SEQUENCE: 75
atgatcagaa t                                                 11

<210> SEQ ID NO 76
```

```
<211> LENGTH: 11
<212> TYPE: DNA
<213> ORGANISM: Artificial Sequence
<220> FEATURE:
<223> OTHER INFORMATION: nucleotide sequence

<400> SEQUENCE: 76
atgattagaa t                                                                11
```